(12) United States Patent
Popik et al.

(10) Patent No.: US 9,090,542 B2
(45) Date of Patent: Jul. 28, 2015

(54) METHODS FOR LABELING A SUBSTRATE USING A HETERO-DIELS-ALDER REACTION

(75) Inventors: Vladimir V. Popik, Watkinsville, GA (US); Selvanathan Arumugam, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 333 days.

(21) Appl. No.: 13/101,473

(22) Filed: May 5, 2011

(65) Prior Publication Data

US 2011/0257047 A1 Oct. 20, 2011

Related U.S. Application Data

(63) Continuation-in-part of application No. 12/945,328, filed on Nov. 12, 2010.

(60) Provisional application No. 61/260,102, filed on Nov. 11, 2009.

(51) Int. Cl.
| | |
|---|---|
| *B01J 19/12* | (2006.01) |
| *C07C 39/38* | (2006.01) |
| *C07C 45/52* | (2006.01) |
| *C07C 49/796* | (2006.01) |
| *C07D 311/92* | (2006.01) |
| *C07D 495/04* | (2006.01) |

(52) U.S. Cl.
CPC .............. *C07C 39/38* (2013.01); *B01J 19/123* (2013.01); *C07C 45/52* (2013.01); *C07C 49/796* (2013.01); *C07D 311/92* (2013.01); *C07D 495/04* (2013.01)

(58) Field of Classification Search
CPC ...... C07C 39/38; C07C 45/52; C07C 49/796; C07D 495/04; C07D 311/92; B01J 19/123
USPC ...................................... 204/157.69
See application file for complete search history.

(56) References Cited

U.S. PATENT DOCUMENTS

| | | | | |
|---|---|---|---|---|
| 4,224,225 | A | * | 9/1980 | Noguchi et al. ............... 549/460 |
| 4,700,010 | A | * | 10/1987 | Ibbotson ..................... 568/433 |
| 4,812,393 | A | * | 3/1989 | Goswami et al. ............. 436/800 |
| 5,037,762 | A | * | 8/1991 | Mura et al. .................. 436/164 |
| 5,466,589 | A | * | 11/1995 | Olinger et al. ................ 435/174 |

(Continued)

OTHER PUBLICATIONS van de Water et al, "o-Quinone methides: intermediates underdeveloped and underutilized in organic synthesis," Tetrahedron vol. 58 (2002), pp. 5367-5405.*

(Continued)

*Primary Examiner* — Keith Hendricks
*Assistant Examiner* — Colleen M Raphael
(74) *Attorney, Agent, or Firm* — Mueting, Raasch & Gebhardt, P.A.

(57) ABSTRACT

Methods for labeling a substrate using a hetero-Diels-Alder reaction are disclosed. The hetero-Diels-Alder reaction includes the reaction of an o-quinone methide (e.g., an o-naphthoquinone methide) with a polarized olefin to form a hetero-Diels-Alder adduct. The o-quinone methide or the polarized olefin can be attached to a surface of a substrate, and the other of the o-quinone methide or the polarized olefin can include a detectable label. The o-quinone methide can conveniently be generated by irradiation of a precursor compound, preferably in an aqueous solution, suspension, or dispersion.

11 Claims, 26 Drawing Sheets a: R=H
d: R= Biotin-NH-CH$_2$-CH$_2$-(O-CH$_2$CH$_2$)$_2$-O-
b: R= CH$_3$-(O-CH$_2$CH$_2$)$_3$-O-
c: R= -OH
e: R= H-(O-CH$_2$CH$_2$)$_3$-O-

X = Linker-Glass surface

(56) References Cited

U.S. PATENT DOCUMENTS

| | | | | |
|---|---|---|---|---|
| 5,939,268 | A * | 8/1999 | Boger | 436/518 |
| 6,657,052 | B1 | 12/2003 | Turnbull | 536/23.1 |
| 6,921,669 | B2 | 7/2005 | Klapproth | 436/527 |
| 8,058,435 | B2 * | 11/2011 | Zhu et al. | 544/342 |
| 8,216,446 | B1 | 7/2012 | Flechsig et al. | 205/777.5 |
| 8,236,949 | B2 * | 8/2012 | Fox et al. | 544/179 |
| 2001/0024798 | A1 * | 9/2001 | Shair et al. | 435/7.1 |
| 2006/0246460 | A1 | 11/2006 | Graham et al. | 435/6 |
| 2006/0263293 | A1 | 11/2006 | Kolb et al. | 424/1.49 |
| 2007/0172905 | A1 | 7/2007 | Taran et al. | 435/7.92 |
| 2007/0249014 | A1 * | 10/2007 | Agnew et al. | 436/106 |
| 2008/0246024 | A1 | 10/2008 | Touwslager et al. | 257/40 |
| 2009/0163741 | A1 * | 6/2009 | Meyer et al. | 568/303 |
| 2011/0108411 | A1 | 5/2011 | Popik et al. | |

OTHER PUBLICATIONS

Freccero, "Quinone Methides as Alkylating and Cross-Linking Agents," Mini-Reviews in Organic Chemistry, 2004, vol. 1, pp. 403-415.*

Pierres et al, "Polymer-supported electron-rich diene for hetero Diels-Alder reactions," Tetrahedron Let. 44 (2003), pp. 3645-3647.*

Bergeron et al, "Near-UV Photolysis of 2-methyl-1,4,-naphthoquinone-DNA duplexes: characterization of reversible and stable interstrand cross-links between quinone and adenine moieties," Chem. Res. Toxicol. (2007), vol. 20, pp. 745-756.*

Goerner, "Photoreactions of 1,4-naphthoquinones: effects of substituents and water on the intermediates and reactivity," Photochemistry and Photobiology (2005) vol. 81, p. 376-383.*

Bruce, "Light-induced reactions of quinones," Q. Rev. Chem. Soc., 1967, vol. 21, pp. 405-428.*

Pisova et al, "Oxidative rearrangement of o-fuchsone to 2,2,-diphenyl-1,3-benzodioxol," Collection Czechslovak Chem. Comm. vol. 47, 1982, pp. 3318-3327.*

Hamai et al, "Photochromism of 2-hydroxytriphenylmethanol and its derivatives," Bull. Chem. Soc. Japan, vol. 48, No. 3, pp. 798-802 (1975).*

Saito et al, "Highly Efficient Photochemical Generation of o-Quinone Methide from Mannich Bases of Phenol Derivatives," Tetrahedron Lett. vol. 38, No. 28, pp. 5005-5008, 1997.*

Graham et al, "Cycloadditions as a Method for Oligonucleotide Conjugation," Current Organic Synthesis, 2006, vol. 3, pp. 9-17.*

Sinnwell et al, "Access to Three-Arm Star Block Copolymers by a Consecutive Combination of the Copper(I)-Catalyzed Azide-Alkyne Cycloaddition and the RAFT Hetero Diels-Alder Concept," Macromolecular Rapid Communications 2008, vol. 29, pp. 1090-1096.*

Hamai et al, "Photochromism of 2-Hydroxytriphenylmethanol and Its Derivatives," Bull. Chem. Soc. Japan vol. 48 (3), pp. 7980802 (1975).*

Adzima et al. Spatial and temporal control of the alkyne-azide cycloadditin by photoinitiated Cu(II) reduction. 2011. *Nature Chem.* 3:258.

Afroz et al. "Photo-removable protecting groups for in situ DNA microarray synthesis", Clin. Chem. 2004. 50:1936-1939.

Arumugam et al. "Photochemical Generation, Reactivity and Application of O-Naphthoquinone Methides". 60th Southeastern Regional Meeting (SERMACS). Nov. 12-15, 2008. Nashville, TN.

Arumugam et al. "Photochemical Generation and the Reactivity of o-Naphthoquinone Methides in Aqueous Solutions". 2009. *J. Am. Chem. Soc.* 131:11892-11899.

Arumugan et al. Light-Indiced Hetero Diels-Alder Cycloaddition: A Facile and Selective Photo-Click Reaction. 2011. *J. Am. Chem. Soc.* 133:5573-5579.

Baskin et al. "Copper-free click chemistry for dynamic in vivo imaging" 2007. *Proc. Natl. Acad. Sci. USA.* 104:16793-16797.

Bates. Determination of pH Theory and Practice; Wiley: NY, 1973. Second Edition. Title Page, Copyright Page, Table of Contents, and p. 49. 8 pages total.

Becer et al. "Click Chemistry beyond Metal-Catalyzed Cycloaddition", 2009. *Angew. Chem. Int. Ed.* 48:4900-4908.

Berlman, I.B., Handbook of Fluorescence Spectra of Aromatic Molecules. Academic Press, NY. 1971. Second Edition. Title Page, Copyright Page, Table of Contents, and p. 473. 7 pages total.

Birks, J.B. Photophysics of Aromatic Molecules. Wiley Interscience, NY. 1970. Title Page, Copyright Page, Table of Contents, and p. 703. 8 pages total.

Blawas et al. "Protein Patterning", *Biomaterials*. 1998. 19:595-609.

Campos et al. Development of thermal and photochemical strategies for thiol-ene click polymer functionalization. 2008. *Macromolecules.* 41:7063.

Carroll et al. "Photons to illuminate the universe of sugar diversity through bioarrays", 2008. *Glycoconj J.* 25:5-10.

Chan et al. "Convergent synthesis of 3-arm star polymers from RAFT-prepared poly(N,N-diethylacrylamide) via a thiol-ene click reaction" 2008. *Chem. Commun.* 4959-4961.

Chen et al. "Shape provides global control of focal adhesion assembly", *Biochem. Biophys. Res. Commun.* 2003. 307:355.

Chen et al. "Antibody microarrays for protein and glycan detection", *Clin. Proteomics.* 2008. 101-111.

Chiellini et al. "Patterning of polymeric hydrogels for biomedical applications", *Macromol. Rapid Commum.*2001. 22:1284.

Choi et al. "Micropatterning of biomolecules on glass surfaces modified with various functional groups using photoactivatable biotin", *Anal. Biochem.* 2005. 347:60-66.

Choi et al. "Patterned immobilization of biomolecules by using ion irradiation-induced graft polymerization", *J. Polym. Sci. A.* 2009. 47:6124-6134.

Codelli et al. "Second-Generation Difluorinated Cyclooctynes for Copper-Free Click Chemistry" 2008. *J. Am. Chem. Soc.* 130:11486-11493.

Colloredo-Mels et al. "Photogenerated Quinone Methides as Useful Intermediates in the Synthesis of Chiral BINOL Ligands", 2006. *J. Org. Chem.* 71:3889-3895.

Crawford et al. "Antibody array technology: screening and profiling protein expression in human cancer serum using antibody array technologies", *Life Sc. Innov.* 2008. 10-13.

Dag et al. "Preparation of 3-Arm Star Polymers ($A_3$) Via Diels-Alder Click Reaction" 2008. *Journ. of Poly. Sci.: Part A: Polymer Chemistry.* 46:302-313.

Datta et al. "Stability and conformation of the complexes of riboflavin with aromatic hydroxyl compounds in an aqueous medium" 2006. *Spec. Acta A.* 64:116-126.

Debets et al. Aza-dibenzocyclooctynes for fast and efficient enzyme PEGylation via copper-free (3+2) cycloaddition. 2010. *Chem. Commun.* 46:97-99.

De Forest et al. Sequential click reactions for synthesizing and patterning three-dimensional cell microenvironments. 2009. *Nature Materials.* 8:659.

Delehanty et al. "A microarray immunoassay for simultaneous detection of proteins and bacteria", *Anal. Chem.* 2002. 74:5681.

Delgado et al. "Microwave-assisted sidewall functionalization of a single-wall carbon nanotubes by Diels-Alder cycloaddition" 2004. *Chem. Commun.* pp. 1734-1735.

Dillmore et al. "A Photochemical Method for Patterning the Immobilization of Ligands and Cells to Self-Assembled Monolayers" 2004. *Langmuir.* 20:7223-7231.

Durmaz et al. "Preparation of block Copolymers Via Diels Alder Reaction of Maleimide- and Anthracene-End Functionalized Polymers" 2006. *J Polym. Sci. Part A: Polymer Chemistry.* 44:1667-1675.

Fiore et al. Photoinduced Thiol-Ene Coupling as a Click Ligation Tool for Thiodisaccharide Synthesis. 2009. *J Org. Chem.* 74:4422-4425.

Fiore et al. Single and dual glycoside clustering around calix[4]arene scaffolds via click thiol-ene coupling and azide-alkyne cycloaddition. 2009. *Org. Biomol. Chem.* 7:3910-3913.

Fleischmann et al. Modification of Polymer Surfaces by Click Chemistry. Macromol. 2008. *Rapid. Commun.* 29:1177-1185.

Fournier et al. Clicking polymers: a straightforward approach to novel macromolecular architectures. 2007. *Chem. Rev. Soc.* 36:1369-1380.

(56) References Cited

OTHER PUBLICATIONS

Gacal et al. "Anthracene—Maleimide-Based Diels-Alder "Click Chemistry" as a Novel Route to Graft Copolymers" 2006. *Macromolecules*. 39:5330-5336.
Ganesan et al. "Simple micropatterning of biomolecules on a diazoketo-functionalized photoresist", *J Mater. Chem*. 2008. 18:703-709.
Ghribi et al. "Reactivity of RCu, $BF_3$ and $R_2$Culi, $BF_3$ Towards Allylic Acetals and Ethers" 1984. *Tetrahedron Lett*. 25:3079-3082.
Graham et al. "Cycloadditions as a Method for Oligonucleotide Conjugation" 2006. *Curr. Org. Synth*. 3:9-17.
Graham et al. "Internal labeling of oligonucleotide probes by Diels-Alder cycloaddition" 2002. *Tetrahedron Lett*. 43:4785-4788.
Graham et al. "Detection of DNA probes using Diels Alder cycloaddition and SERRS" 2003. *Analyst*. 128:692-699.
Greco et al. "Polymer-drug conjugates: current status and future trends", *Frontiers in Bioscience*, 2008. 13:2744-2756.
Grobelny et al. "Decomosition of vinyl ethers by alkalide $K^-$, $K+$ (15-crown-5)$_2$ via organopotassium intermediates" 2004. *J. Organomet Chem*. 689:1580-1585.
Hein et al., Copper-catalyzed azide-alkyne cycloaddition (CuAAC) and beyond: newreactivity of copper (I) acetylides. 2010. *Chem. Soc. Rev*. 39:1302-1315.
Hensarling et al. "Clicking" Polymer Brushes with Thiol-yne Chemistry: Indoors and Out. 2009. *J. Am. Chem. Soc*. 131(41):14673-14675.
Hill et al. "Diels-Alder Bioconjugation of Diene-Modified Oligonucleotides" 2001. *J. Org. Chem*. 66:5352-5358.
Husar et al. 2001. "Covalent Modification and Surface Immobilization of Nucleic Acids via the Diels-Alder Bioconjugation Method" *Nucleosides Nucleotides Nucleic Acids*. 20(4-7):559-566.
Iha et al., Applications of Orthogonal "Click" Chemistries in the Synthesis of Functional Soft Materials. 2009. *Chem. Rev*. 109:5620-5686.
Im et al. Patterning Nanodomains with Orthogonal Functionalities: Solventless Synthesis of Self-Sorting Surfaces. 2008. *J. Am. Chem. Soc*. 130:14424-14425.
Jiang et al. "Photogenerated Quinone Methides as Protein Affinity Labeling Reagents" 2009. *ChemBioChem*. 10:635-638.
Johnson et al. "Synthesis of Degradable Model Networks via ATRP and Click Chemistry" 2006. *J. Am. Chem. Soc*. 128(20):6564-6565.
Joralemon et al. "Shell Click-Crosslinked (SCC) Nanoparticles: A New Methodology for Synthesis and Orthogonal Functionalization" 2005. *J. Am. Chem. Soc*. 127(48):16892-16899.
Killops et al. "Robust, Efficient, and Orthogonal Synthesis of Dendrimers via Thiol-ene "Click" Chemistry" 2008. *J Am. Chem. Soc*. 130:5062-5064.
Kim et al. "Polymer-bound Boronate via the Solid Phase Coupling Reaction of Resin-bound Aryl Triflate with Diboron Pinacol Ester" 2000. *Korean Chem. Soc*. 21(8):757-758.
Klima et al. "Photoinduced C—N Bond Cleavage in 2-Azido-1,3-diphenyl-propan-1-one Derivatives: Photorelease of Hydrazoic Acid" 2007. *J Org. Chem*. 72(17):6372-6381.
Kolb et al. "Click Chemistry: Diverse Chemical Function from a Few Good Reactions" 2001. *Angew. Chem. Int. Ed*. 40:2004-2021.
Kolb et al. "The growing impact of click chemistry on drug discovery" 2003. *Drug. Discov*. 8(24):1128-1137.
Ku et al. "Surface Patterning with Fluorescent Molecules Using Click Chemistry Directed by Scanning Electrochemical Microscopy" *J Am. Chem. Soc*. 2008. 130(8):2392-2393.
Kulikov et al. "Photolabile Protection of Alcohols, Phenols, and Carboxylic Acids with 3-Hydroxy-2-Naphthalenemethanol" 2008. *J Org. Chem*. 73:7611-7615.
Kuzmin et al. "Surface Functionalization Using Catalyst-Free Azide-Alkyne Cycloaddition" *Bioconjugate Chem*. 2010.21(11):2076-2085.
Latham-Timmons et al. "Novel Method for the Covalent Immobilization of Oligonucleotides via Diels-Alder Bioconjugation" Abstract. 2003. *Nucleic Acids*. 22(5-8):1495-1497; Proceedings of the XV International Round Table. Leuven, Belgium, Sep. 10-14, 2002.
Lee et al. In Neoglycoconjugates. Preparation and Applications; Eds.; Academic Press: New York, 1994. Title Page, Copyright Page, Table of Contents, and pp. 325-371.
Lee et al. Methods in Enzymology; Neoglycoconjugates. Part A—Synthesis. Academic Press: San Diego, 1994. vol. 242. Title Page, Copyright Page and Table of Contents. 6 pages total.
MacBeath et al. "Printing proteins as microarrays for high-throughput function determination", *Science*. 2000. 289:1760.
Malkoch et al. "Orthogonal Approaches to the Simultaneous and Cascade Functionalization of Macromolecules Using Click Chemistry" 2005. *J Am. Chem. Soc*. 127:14942-14949.
Mamidyala et al. In situ click chemistr-y: probing the binding landscapes of biological molecules. 2010. *Chem. Soc. Rev*. 39:1252-1261.
Martin et al. Organic Preparations and Procedures International; The New Journal for Organic Synthesis. 1991. *Org. Prep. Proc. Int*. Title Page, Copyright Page, Table of Contents and pp. 237-272.
McGlennen. "Miniaturization technologies for molecular diagnostics", *Clin. Chem*. 2001. 47:393-402.
Michel et al. "Carbohydrate Microarrays by Microcontact "Click" Chemistry" 2008. *Langmuir*. 24:12116-12118.
Morais et al. "DNA microarraying on compact disc surfaces. Application to the analysis of single nucleotide polymorphisms in Plum pox virus", *Chem. Commun*. 2006. 2368-2370.
Moses et al. "The growing applications of Click Chemistry" 2007. *Chem. Soc. Rev*. 36:1249-1262.
Murov et al. in: Handbook of Photochemistry, Second Edition, Revised and Expanded. Title Page, Copyright Page, Table of Contents, and p. 299. Marcel Dekker; New York. 1993.
Nakajima. "Patterning of protein on the microchannel wall", *J. Flow Inj. Anal*. 2006. 23:123.
Nandivada et al. "Click Chemistry: Versatility and Control in the Hands of Materials Scientists" 2007. *Adv. Mater*. 19:2197-2208.
Nebhani et al., "Orthogonal Transformations on Solid Substrates: Efficient Avenues to Surface Modification" 2009. *Adv. Mat*. 21:3442-3468.
Ning et al. "Visualizing Metabolically Labeled Glycoconjugates of Living Cells by Copper-Free and Fast Huisgen Cycloadditions" 2008. *Angew. Chem. Int. Ed*. 47:2253-2255.
Oppolzer. "Intramolecular Cycloaddition Reactions of ortho-Quinodimethanes in Organic Synthesis" 1978. *Synthesis*. p. 793-802.
Orski et al. "High Density Orthogonal Surface Immobilization via Photoactivated Copper-Free Click Chemistry" 2010. *J. Am. Chem. Soc*. 132:11024-11026.
Panda et al. "An array of insights: application of DNA chip technology in the study of cell biology", *Trends Cell Biol*. 2003. 13:151.
Peeters et al. "Polysaccharide-Conjugate Vaccines" In Vaccine Protocols: A. Robinson, G. Farrar, C. Wiblin, Eds.; Humana Press Inc: Totowa, NJ. 1996. pp. 111-133.
Pei et al. "Photoderivatized Polymer Thin Films at Quartz Crystal Microbalance Surfaces: Sensors for Carbohydrate-Protein Interactions", *Anal. Chem*. 2007. 79(18):6897-6902.
Popper et al. "Proteomics-tissue and protein microarrays and antibody array: what information is provided?", *Arch. Path. & Lab*. 2008. 132:1570-1572.
Pozsgay et al. "A Method for Bioconjugation of Carbohydrates Using Diels-Alder Cycloaddition" 2002. *Org. Lett*. 4(19):3191-3194.
Proupin-Perez et al. "Studies on the Attachment of DNA to Silica-Coated Nanoparticles Through a Diels-Alder Reaction" 2005. *Nucleotides Nucleic Acids*.24(5-7):1075-1079.
Punna et al. "Clickable Agarose for Affinity Chromatography" 2005. *Bioconjugate Chem*. 16:1536-1541.
Punna et al. "Head-to-Tail Peptide Cyclodimerization by Copper-Catalyzed Azide-Alkyne Cycloaddition" 2005. *Angew. Chem. Int. Ed*. 44:2215-2220.
Ramachary et al. "Towards Organo-Click Chemistry: Development of Organocatalytic Multicomponent Reactions Through Combinations of Aldol, Wittig, Knoevenagel, Michael, Diels-Alder and Huisgen Cycloaddition Reactions" 2004. *Chem. Eur. J*. 10(21):5323-5331.

(56) References Cited

OTHER PUBLICATIONS

Ratner et al., Biomaterials Science: An introduction to materials in medicine. 2nd Edition. Academic Press, San Diego, CA. 2004. Title page, Copyright Page, and Table of Contents. 6 pages total.
Robbins et al. The 1996 Albert Lasker Medical Research Awards. "Prevention of systemic infections, especially meningitis, caused by *Haemophilus influenzae* type b:Impact on public health and implications for other polysaccharide-based vaccines" 1996. *J. Am. Med. Assoc.* 276(14):1181-1185.
Rostovtsev et al., "A Stepwise Huisgen Cycloaddition Process: Copper(I)-Catalyzed Regioselective "Ligation" of Azides and Terminal Alkynes" 2002. *Angew. Chem. Int. Ed.* 41(14):2596-2599.
Rusmini et al. "Protein Immobilization Strategies for Protein Biochips" 2007. *Biomacromolecules.* 8:1775-1789.
Seelig et al. "Site-Specific Modification of Enzymatically Synthesized RNA: Transcription Initiation and Diels-Alder Reaction" 1997. *Tetrahedron Lett.* 38(44):7729-7732.
Seelig et al. "A Small catalytic RNA motif with Diels-Alderase activity" 1999. *Chem. & Biol.* 6(3):167-176.
Segura et al. "*o*-Quinodimethanes: Efficient Intermediates in Organic Synthesis" 1999. *Chem. Rev.* 99:3199-3246.
Sharpless et al. "In situ click chemistry: a powerful means for lead discovery" *Exp. Opin. Drug. Discov.* 2006. 1(6):525-538.
Sletten et al. "A Hydrophilic Azacyclooctyne for Cu-Free Click Chemistry" 2008. *Org. Lett.* 10(14):3097-3099.
Song et al. "Selective Functionalization of a Genetically Encoded Alkene-Containing Protein via "Photoclick Chemistry" in Bacterial Cells", *J. Am. Chem. Soc.* 2008. 130(30):9654-9655.
Song et al. "Photoinducible 1,3-Dipolar Cycloaddition Reaction for Rapid, Selective Modification of Tetrazole-Containing Proteins" 2008. *Angew. Chem. Int. Ed. Engl.* 47:2832-2835.
Strable et al. "Unnatural Amino Acid Incorporation into Virus-Like Particles" 2008. *Bioconjugate Chem.* 19:866-875.
Sun et al. "Carbohydrate and Protein Immobilization onto Solid Surfaces by Sequential Diels-Alder and Azide-Alkyne Cycloadditions" 2006. *Bioconjugate Chem.* 17:52-57.
Tarasow et al. "RNA-catalysed carbon—carbon bond formation" 1997. *Nature.* 389:54-57.
Thibault et al. "A Versatile New Monomer Family: Functionalized 4-Vinyl-1,2,3-Triazoles via Click Chemistry" 2006. *J. Am. Chem. Soc.* 128:12084-12085.
Tornoe et al. "Peptidotriazoles on Solid Phase: [1,2,3]-Triazoles by Regiospecific Copper(I)-Catalyzed 1,3-Dipolar Cycloadditions of Terminal Alkynes to Azides" *J. Org. Chem.* 2002. 67(9):3057-3064.
Van den Berg et al. "Approach Toward a Generic Treatment of Gram-Negative Infections: Synthesis of Haptens for Catalytic Antibody Mediated Cleavage of the Interglycosidic Bond in Lipid A" 1999. *Eur. J. Org. Chem.* pp. 2593-2600.
Von Maltzahn et al. "In Vivo Tumor Cell Targeting with "Click" Nanoparticles" 2008. *Bioconjugate Chem.* 19:1570-1578.
Wang et al. "Bioconjugation by Copper(I)-Catalyzed Azide-Alkyne [3+2] Cycloaddition" 2003. *J. Am. Chem. Soc.* 125:3192-3193.
Wang et al. "Photoinduced Electron Transfer in a Supramolecular Species Building of Mono-6-p-nitrobenzoyl-β-cyclodextrin with Naphthalene Derivatives" 2002. *J Org. Chem.* 67:2429-2434.
Wang et al. "Fast Alkene Functionalization In Vivo by Photoclick Chemistry: HOMO Lifting of Nitrile Imine Dipoles" 2009. *Angew. Chem. Int. Ed. Engl.* 48:5330-5333.
Wong et al., "Selective Covalent Protein Immobilization: Strategies and Applications" 2009. *Chem. Rev.* 109:4025-4053.
Wu et al. "Efficiency and Fidelity in a Click-Chemistry Route to Triazole Dendrimers by the Copper(I)-Catalyzed Ligation of Azides and Alkynes" 2004. *Angew. Chem. Int. Ed.* 43:3928-3932.
Yousaf et al. "Using electroactive substrates to pattern the attachment of two different cell populations" 2001. *Proc. Natl. Acad. Sci. USA.* 98(11):5992-5996.

Batsomboon et al. "Generation of ortho-quinone methides by p-TsOH on silica and their hetero-Diels-Alder reactions with styrene," 2009. *J. Org. Chem.* 74:4009-4012.
Bray. "Generation and hetero-Diels-Alder reactions of an o-quinone methide under miki, anionic conditions: rapid synthesis of monobenzannelated spiroketals," 2008. *Org. & Biol. Chem.* 6:2815-2819.
Stokes et al. "Formation of o-Quinone Methides from η2-Coordinated Phenols and their Controlled Release from a Transition Metal to Generate Chromans," Organometallics. 2003. 22:4170-4171.
Tang et al. "Strategies and approaches for constructing 1-oxadecalins," Tetrahedron 62 (2006), pp. 10785-10813.
Wan et al. "Quinone methides; relevant intermediates in organic chemistry," Can. J. Chem. vol. 74, 1996. pp. 465-475.
Wang et al. "A DFT study of Diels-Alder reactions of o-quinone methides and various substituted ethenes: selectivity and reaction mechanism," J. Org. Chem. 70:4910-4917. 2005.
Stokes at al, "Formation of o-Quinone Methides from η2-Coordinated Phenols and their Controlled Release from a Transition Metal to Generate Chromans," Organometallics 2003, vol. 22, pp. 4170-4171.
van de Water at al, "o-Quinone methides: Intermediates underdeveloped and underutilized in organic synthesis," Tetrahedron vol. 58 (2002), pp. 5367-5405.
Jorgensen, "Catalytic Asymmetric Hetero-Diels-Alder Reactions of Carbonyl Compounds and Imines," Angewandte Chemie Int'l Ed. 2000, vol. 39, pp, 3558-3588.
Callie et al. Ortho-quinone methide imine generation and Diels-Alder reactions and room temperature, Synlett. Jul. 1996. pp. 669-671.
Chauhan et al. "Synthesis of some new tetracyclic heteroaromatie chromans via quinone methide intermediates" Can. J. Chem. 59:2223-2227, 1981.
Chiang et al. "Flash photolytic generation of o-quinone alpha-phenylmethide and o-quinone alpha-(p-anisyl)methide in aqueous solution and investigation of their reacitons in that medium. Saturation of acid-catalyzed hydration," J. Am. Chem. Soc. vol. 124, No. 4, 2002, pp. 717-722.
Chiang et al. "Flash photolytic generation of o-quinone methide in aqueous solution and study of its chemistry in that medium," J. Am. Chem. Soc. vol. 123, No. 33, 2001, pp. 8089-8094.
Desmoni et al., Heterodiene syntheses with alpha,beta-unsaturated carbonyl compounds, 75(6):6S1-692. 1975.
Diao et al., "Quinone methide intermediates from the photolysis of hydroxybenzyl alcohols in aqueous solution" J. Am. Chem. Soc. 1995. 117:5369-5370.
Gharpure et al. "o-Quinone methide based approach to isoflavans: application to the total synthesis of equol, 3'-hydroxyequol, and vestitol," Tetrahedron Letters. 49:2974-2978. 2008.
Jorgensen, "Catalytic Asymmetric Hetero-Diels-Alder Reactions of Carbonyl Compounds and Imines," Angewandte Chemie Int'l Ed, 2000. vol. 39. pp. 3558-3588.
Modica et al., "Alkylation of amino acids and glutathione in water by o-quinone methide. Reactivity and selectivity" J. Org. Chem. 2001. 66:41-52.
Nakatani et al. "Highly efficient photochemical generation of o-quinone methide from Maannich bases of phenol derivatives". Tetrahedron lett. 38(28):5005-5008. 1997.
Rodriguez et al. "A new and efficient method for o-quinone methide intermediate generation: application to the biomimetic synthesis of (+/−)-alboatrin," Org. Lett. 2006, 6(20):3617-3619.
Antonin et al. "2- and 6-Methyl-1,4-naphthoquinone Derivatives as Potential Bioreductive Alkylating Agents". *Journal of Medicninal Chemistry.* 1982. 25(6):731-735.
Chatterjee et al. "Inducible Alkylation of DNA Using an Oligonucleotide-Quinone Conjugate". *J. Am. Chem. Soc.* 1990. 112(17):6397-6399.

* cited by examiner a: R=H
d: R= Biotin-NH-CH$_2$-CH$_2$-(O-CH$_2$CH$_2$)$_2$-O-
b: R= CH$_3$-(O-CH$_2$CH$_2$)$_3$-O-
c: R= -OH
e: R= H-(O-CH$_2$CH$_2$)$_3$-O- a)

b2)

b1)

METHODS FOR LABELING A SUBSTRATE USING A HETERO-DIELS-ALDER REACTION

The present application is a continuation-in-part application of U.S. patent application Ser. No. 12/945,328, filed Nov. 12, 2010, which claims the benefit of U.S. Provisional Application No. 61/260,102, filed Nov. 11, 2009; both of which are incorporated herein by reference in their entireties.

GOVERNMENT FUNDING

The present invention was made with government support under Grant No. CHE 0842590, awarded by the National Science Foundation. The Government has certain rights in this invention.

BACKGROUND

Connection (or ligation in biochemistry) of two or more substrates or immobilization of various compounds are often achieved with the help of "click chemistry," which describes a set of bimolecular reactions that are modular, wide in scope, high yielding, create only inoffensive by-products, are stereospecific, simple to perform and that require benign or easily removed solvent. Although meeting all of the above requirements is difficult to achieve, several processes have been identified as coming very close to the ideal "click reaction." Among them are 1,3 dipolar and Diels-Alder cycloadditions, nucleophilic ring opening, non-aldol carbonyl chemistry, and additions to carbon-carbon multiple bonds. Cu(I) catalyzed versions of the Huisgen acetylene-azide cycloaddition, also known as azide click reaction, became the gold standard of click chemistry and have been applied in fields ranging from material science to chemical biology and drug development. However, the use of cytotoxic Cu (I) catalysts has largely precluded application of this click reaction in living systems. Recently discovered catalyst-free 1,3-dipolar cycloaddition of azides to cyclooctynes and dibenzocyclooctynes offers a bio-compatible version of the azide click reaction.

"Click" methods based on a Diels-Alder cycloaddition are also gaining popularity due to the fact that this reaction does not require catalysts, can proceed in high yield under physiological conditions, and does not produce any by-products. However, Diels-Alder cycloaddition reactions are often slow and require either thermal activation or the use of chemical promoters for the in situ generation of highly reactive dienes.

Thus, there remains a need for catalyst-free ligation methods for connection or immobilization of various compounds.

SUMMARY

The present disclosure provides methods for labeling a substrate.

In one embodiment, the method includes: generating an o-quinone methide attached to a surface of a substrate and having the formula:

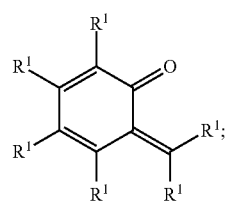

Formula IV and contacting the o-quinone methide with a polarized olefin having the formula:

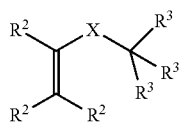

Formula III under conditions effective to form a hetero-Diels-Alder adduct, wherein: each $R^1$ is independently H, halogen, or an organic group, with the proviso that at least one $R^1$ includes a linker group attached to the surface of the substrate; each $R^2$ is independently H or an organic group; each $R^3$ is independently H, halogen, or an organic group; and X is O or $NR^4$, wherein $R^4$ is H or an organic group, with the proviso that at least one $R^2$, $R^3$, or $R^4$ includes a detectable label. Optionally, $R^3$ or $R^4$ includes the detectable label, and the method can further include removing the detectable label from the surface of the substrate by hydrolyzing the C—X bond. Optionally, two or more $R^1$ groups may be combined to form one or more rings (e.g. to form an o-naphthoquinone methide or an o-anthraquinone methide). Optionally, two or more $R^2$ groups may be combined to form one or more rings. Optionally, two or more $R^3$ and/or $R^4$ groups may be combined to form one or more rings. In certain preferred embodiments, the o-quinone methide is an o-naphthoquinone methide having one of the formulas:

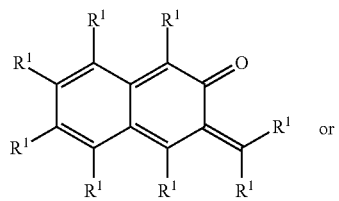

Formula Va or

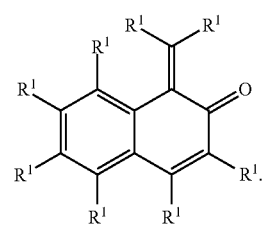

Formula Vb

In another embodiment, the method includes: providing a precursor compound attached to a surface of a substrate and having the formula:

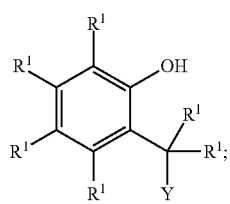

Formula I irradiating the precursor compound under conditions effective to form an o-quinone methide having the formula:

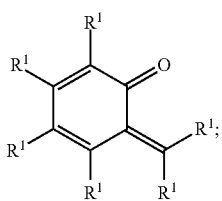

Formula IV and contacting the o-quinone methide with a compound having the formula

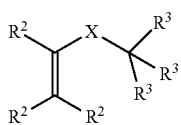

Formula III under conditions effective to form a hetero-Diels-Alder adduct, wherein: each $R^1$ is independently H, halogen, or an organic group, with the proviso that at least one $R^1$ includes a linker group attached to the surface of the substrate; each $R^2$ is independently H or an organic group; each $R^3$ is independently H, halogen, or an organic group; X is O or $NR^4$; Y is $OR^5$, $NR^5_2$, $NR^5_3{}^+(Z_{1/q})^-$ wherein Z is an anion having a negative charge of q; and each $R^4$ and $R^5$ is independently H or an organic group, with the proviso that at least one $R^2$, $R^3$, or $R^4$ includes a detectable label. Optionally, two or more $R^1$ groups may be combined to form one or more rings (e.g. to form a naphthalene ring in a precursor of an o-naphthoquinone methide; or to form an anthracene ring in a precursor of an o-anthraquinone methide). Optionally, two or more $R^2$ groups may be combined to form one or more rings. Optionally, two or more $R^3$ and/or $R^4$ groups may be combined to form one or more rings. Optionally, two or more $R^5$ groups may be combined to form one or more rings. Optionally, the precursor compound can be irradiated in the presence of the polarized olefin. In certain embodiments, irradiating the precursor compound can include pattern-wise irradiating the substrate to provide a pattern-wise labeled surface of the substrate. In certain preferred embodiments, the precursor compound has one of the formulas:

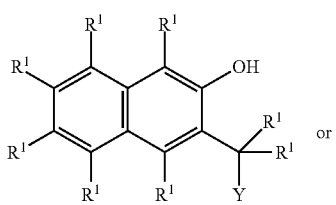

Formula IIa

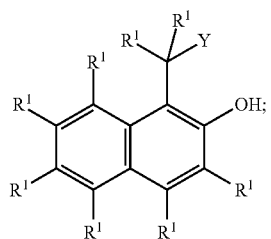

Formula IIb and irradiating the precursor compound under conditions effective to form an o-quinone methide forms an o-naphthoquinone methide having one of the formulas:

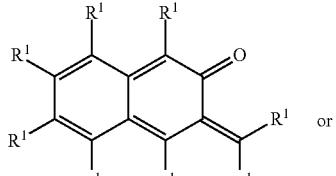

Formula Va or

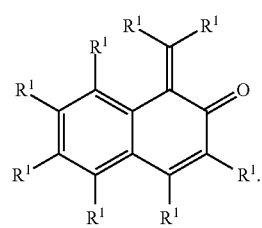

Formula Vb

In another embodiment, the method includes: generating an o-quinone methide having the formula:

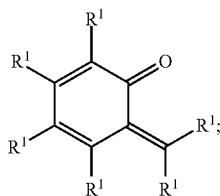

Formula IV and contacting the o-quinone methide with a polarized olefin attached to a surface of a substrate and having the formula:

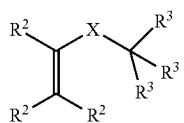

Formula III under conditions effective to form a hetero-Diels-Alder adduct, wherein: each $R^1$ is independently H, halogen, or an organic group, with the proviso that at least one $R^1$ includes a detectable label; each $R^2$ is independently H or an organic group; each $R^3$ is independently H, halogen, or an organic group; and X is O or $NR^4$, wherein $R^4$ is H or an organic group, with the proviso that at least one $R^2$, $R^3$, or $R^4$ includes a linker group attached to the surface of the substrate. Optionally, two or more $R^1$ groups may be combined to form one or more rings (e.g. to form an o-naphthoquinone methide or an o-anthraquinone methide). Optionally, two or more $R^2$ groups may be combined to form one or more rings. Optionally, two or more $R^3$ and/or $R^4$ groups may be combined to form one or more rings. Optionally, the method can further include removing the detectable label from the surface of the substrate by hydrolyzing the C—X bond. In certain preferred embodiments, the o-quinone methide is an o-naphthoquinone methide having one of the formulas:

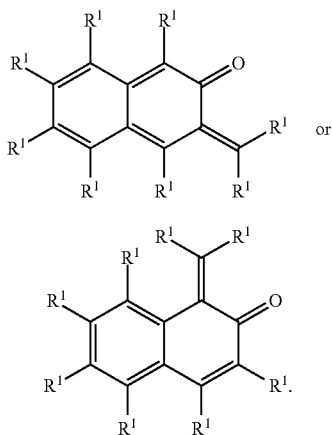

Formula Va

Formula Vb

In another embodiment, the method includes: providing a precursor compound having the formula:

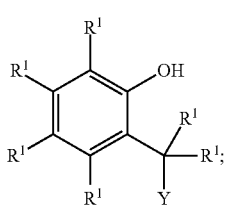

Formula I irradiating the precursor compound under conditions effective to form an o-quinone methide having the formula:

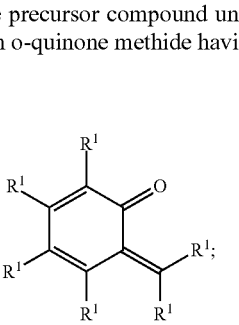

Formula IV and contacting the o-quinone methide with a polarized olefin attached to a surface of a substrate and having the formula:

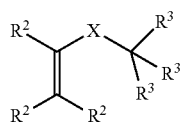

Formula III under conditions effective to form a hetero-Diels-Alder adduct, wherein: each $R^1$ is independently H, halogen, or an organic group, with the proviso that at least one $R^1$ includes a detectable label; each $R^2$ is independently H or an organic group; each $R^3$ is independently H, halogen, or an organic group; X is O or $NR^4$; Y is $OR^5$, $NR^5_2$, $NR^5_3{}^+(Z_{1/q})^-$ wherein Z is an anion having a negative charge of q; and each $R^4$ and $R^5$ is independently H or an organic group, with the proviso that at least one $R^2$, $R^3$, or $R^4$ includes a linker group attached to the surface of the substrate. Optionally, two or more $R^1$ groups may be combined to form one or more rings (e.g. to form a naphthalene ring in a precursor of an o-naphthoquinone methide; or to form an anthracene ring in a precursor of an o-anthraquinone methide). Optionally, two or more $R^2$ groups may be combined to form one or more rings. Optionally, two or more $R^3$ and/or $R^4$ groups may be combined to form one or more rings. Optionally, two or more $R^5$ groups may be combined to form one or more rings. Optionally, the precursor compound can be irradiated in the presence of the polarized olefin. Optionally, irradiating the precursor compound can include pattern-wise irradiating the substrate to provide a pattern-wise labeled surface of the substrate. In certain preferred embodiments, the precursor compound has one of the formulas:

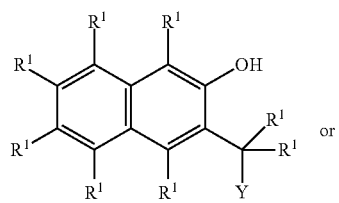

Formula IIa

Formula IIb and irradiating the precursor compound under conditions effective to form an o-quinone methide forms an o-naphthoquinone methide having one of the formulas:

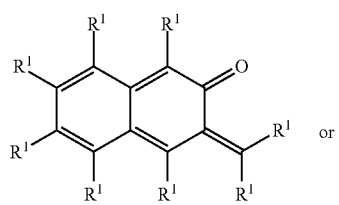

Formula Va

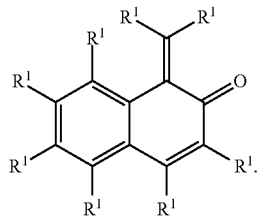

Formula Vb

In another aspect, the present disclosure provides a precursor compound having the formula:

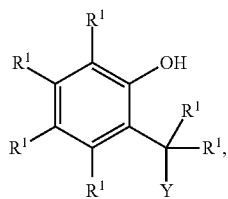

Formula I wherein: each $R^1$ is independently H, halogen, or an organic group; Y is $OR^5$, $NR^5_2$, $NR^5_3{}^+(Z_{1/q})^-$ wherein Z is an anion having a negative charge of q; and each $R^4$ and $R^5$ is independently H or an organic group, with the proviso that at least one $R^1$ includes a detectable label or a linker group attached to a surface of a substrate. Optionally, two or more $R^1$ groups may be combined to form one or more rings (e.g. to form a naphthalene ring or an anthracene ring). Optionally, two or more $R^5$ groups may be combined to form one or more rings. In certain preferred embodiments, the precursor compound has one of the formulas:

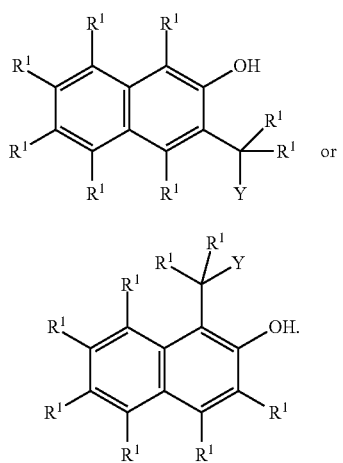

Formula IIa

Formula IIb

In another aspect, the present disclosure provides an o-quinone methide having the formula:

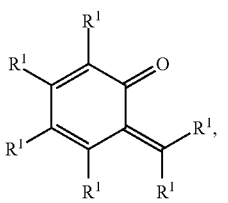

Formula IV wherein each $R^1$ is independently H, halogen, or an organic group, with the proviso that at least one $R^1$ includes a detectable label or a linker group attached to a surface of a substrate. Optionally, two or more $R^1$ groups may be combined to form one or more rings (e.g. to form an o-naphthoquinone methide or an o-anthraquinone methide). In certain preferred embodiments, the o-quinone methide is an o-naphthoquinone methide of one of the formulas:

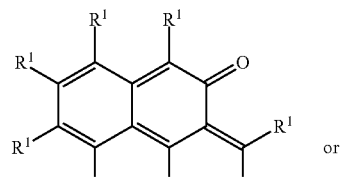

Formula Va or

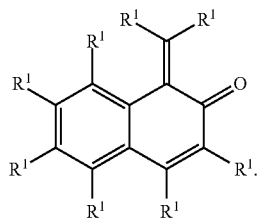

Formula Vb

The reactions recited in the present disclosure can allow for the development of reagentless and catalyst-free ligation methods. In some embodiments, these methods are based on the in situ photochemical generation of the reactive component of a cycloaddition reaction. This approach can also expand the utility of "click" techniques by permitting temporal and spatial (potentially even 3-D) control over the process. Photogenerated click-substrates are expected to cover a broad range of reactivities from 0.1 to $10^4$ $M^{-1}s^{-1}$. The advantages of photo-triggered click approaches to ligation and immobilization are well recognized.

Photochemical immobilization of carbohydrates, proteins, DNA fragments, antibodies, and other substrates allows for the formation of patterned or gradient arrays on various surfaces. These techniques can be used in the development of novel high throughput analytical methods.

The photo-triggered click reactions disclosed herein can expand the utility of this technique. First, the photoreactions employed can produce reactive components that have higher quantum and quantitative chemical yields. As a result, methods described herein typically require only short irradiation with a low intensity lamp, thus exhibiting much less light-induced toxicity in cells. Second, photochemical hetero-Diels-Alder reactions are very fast and allow for high spatial resolution of labeling or ligation. In addition, they provide a ligation method orthogonal to the azide click reaction. The o-quinone methides do react with water, but this reaction can actually be beneficial, because it regenerates the precursor compound. Thus, photo-ligation methods disclosed herein can be compatible with biological media.

DEFINITIONS

As used herein, "a," "an," "the," and "at least one" are used interchangeably and mean one or more than one.

As used herein, the term "comprising," which is synonymous with "including" or "containing," is inclusive, open-ended, and does not exclude additional unrecited elements or method steps.

The above brief description of various embodiments of the present invention is not intended to describe each embodiment or every implementation of the present invention. Rather, a more complete understanding of the invention will become apparent and appreciated by reference to the following description and claims in view of the accompanying drawings. Further, it is to be understood that other embodiments may be utilized and structural changes may be made without departing from the scope of the present invention.

DETAILED DESCRIPTION OF ILLUSTRATIVE EMBODIMENTS

Figure 1:
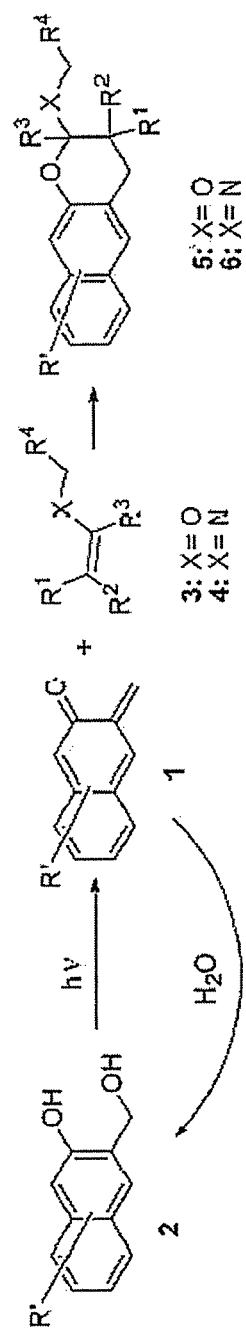
FIGS. 1 and 2 are schematic illustrations of embodiments of the generation of an o-naphthoquinone methide by irradiation of a precursor compound, followed by a hetero-Diels-Alder reaction with a polarized olefin to form a hetero-Diels-Alder adduct.

The present disclosure provides methods for labeling a substrate using a hetero-Diels-Alder reaction. The hetero-Diels-Alder reaction includes the reaction of an o-quinone methide (e.g., an o-naphthoquinone methide) with a polarized olefin to form a hetero-Diels-Alder adduct. The o-quinone methide or the polarized olefin can be attached to a surface of a substrate, and the other of the o-quinone methide or the polarized olefin can include a detectable label. The o-quinone methide can conveniently be generated by irradiation of a precursor compound, preferably in an aqueous solution, suspension, or dispersion.

Precursor Compounds.

In one embodiment, an o-quinone methide is generated from a precursor compound having the formula:

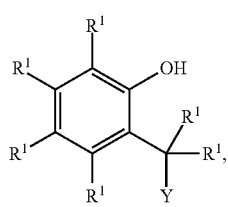

Formula I wherein: each $R^1$ is independently H, halogen, or an organic group; Y is $OR^5$, $NR^5_2$, $NR^5_3{}^+(Z_{1/q})^-$ wherein Z is an anion having a negative charge of q; and each $R^4$ and $R^5$ is independently H or an organic group, with the proviso that at least one $R^1$ includes a detectable label or a linker group attached to a surface of a substrate. Optionally, two or more $R^1$ groups may be combined to form one or more rings (e.g. to form a naphthalene ring or an anthracene ring). Optionally, two or more $R^5$ groups may be combined to form one or more rings. In certain preferred embodiments, an o-naphthoquinone methide is generated from a precursor compound having one of the formulas:

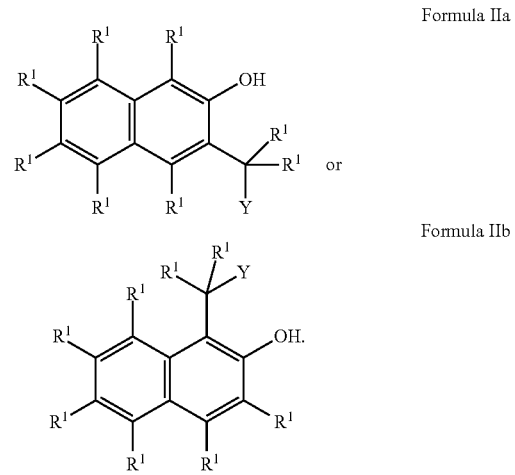

When $R^1$ and/or $R^5$ represent an organic group, preferably the organic group is a carbon-bound (i.e., the bond to the group is to a carbon atom of the organic group) organic group. In certain embodiments, the organic group is an aliphatic group such as a C1-C20 aliphatic group, in some embodiments a C1-C10 aliphatic group, and in some embodiments a C1-C10 hydrocarbon moiety.

As used herein, the term "organic group" is used for the purpose of this disclosure to mean a hydrocarbon group that is classified as an aliphatic group, cyclic group, or combination of aliphatic and cyclic groups (e.g., alkaryl and aralkyl groups). In the context of the present disclosure, suitable organic groups for hetero-Diels-Alder reactants or precursors thereof, as described herein, are those that do not interfere with a light-induced photodehydration reaction and/or a [4+2] cycloaddition reaction. In the context of the present disclosure, the term "aliphatic group" means a saturated or unsaturated linear or branched hydrocarbon group. This term is used to encompass alkyl, alkenyl, and alkynyl groups, for example. The term "alkyl group" means a saturated linear or branched monovalent hydrocarbon group including, for example, methyl, ethyl, n-propyl, isopropyl, tert-butyl, amyl, heptyl, and the like. The term "alkenyl group" means an unsaturated, linear or branched monovalent hydrocarbon group with one or more olefinically unsaturated groups (i.e., carbon-carbon double bonds), such as a vinyl group. The term "alkynyl group" means an unsaturated, linear or branched monovalent hydrocarbon group with one or more carbon-carbon triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

As a means of simplifying the discussion and the recitation of certain terminology used throughout this application, the terms "group" and "moiety" are used to differentiate between chemical species that allow for substitution or that may be substituted and those that do not allow for substitution or may not be so substituted. Thus, when the term "group" is used to describe a chemical substituent, the described chemical material includes the unsubstituted group and that group with nonperoxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

Substrates.

In some embodiments, the precursor compound, the o-quinone methide (e.g., an o-naphthoquinone methide), the polarized olefin, and/or the hetero-Diels-Alder adduct are attached to the surface of a substrate. A substrate can be of any suitable size and/or shape. For example, useful substrates include planar surfaces and beads (e.g., particles such a microbeads having an average size less than 0.1 mm). Substrates including a wide variety of materials can be used. For example, suitable substrates can include glass, quartz, silica, metal, semi-conductor, polymer, membrane, liposome, micelle, macromolecule, a biomaterial, or a combination thereof. As used herein, the term "biomaterial" is meant to include any biological material or material that can be used in a biological method or application. Such materials include, but are not limited to cells, viruses, small multicellular organisms, DNA, RNA, peptides, polypeptides, proteins, carbohydrates, lipids, tissues, or combinations thereof.

Linkers

For embodiments in which the precursor compound, the o-quinone methide (e.g., an o-naphthoquinone methide), the polarized olefin, and/or the hetero-Diels-Alder adduct are attached to the surface of a substrate, the attachment may include a linker. A wide variety of linkers known to those of skill in the art can be used to attach the substrate. For example, useful linkers can include, but are not limited to, aliphatic chains and alkylene glycol oligomers (e.g., ethylene glycol oligomers).

Detectable Labels

In some embodiments, a detectable label is attached to the precursor compound, the o-quinone methide (e.g., an o-naphthoquinone methide), the polarized olefin, and/or the hetero-Diels-Alder adduct. As used herein, a detectable label is meant to include any group or functionality desired that can be detected before and/or after attachment to the surface of a substrate. The labels can be detected by a wide variety of convenient methods including, but not limited to, fluorescence, phosphorescence, radiation detection, optical and electrochemical methods, surface plasmon resonance imaging (SPRi), or combinations thereof.

In some embodiments, the detectable label can include a probe molecule. A wide variety of probe molecules can be used including, for example, DNA, peptides, polypeptides, proteins, and combinations thereof.

Generation of o-Quinone Methide.

Precursor compounds as disclosed herein can be irradiated to generate o-quinone methides (e.g., o-naphthoquinone methides). Typically, the precursor compound is irradiated in an aqueous solution, suspension, or dispersion. As used herein, an aqueous solution, suspension, or dispersion is intended to include liquids that include, but are not limited to, water. Thus, aqueous liquids can also include, for example, organic solvents such as acetonitrile.

Typically, the aqueous solution, suspension, or dispersion of the precursor compound is irradiated at a wavelength of 250 nm to 350 nm. Convenient wavelengths include, for example, 350 nm such as those available from a fluorescent UV lamp. Other convenient wavelengths include, for example, 266 nm and 355 nm. Typically, the aqueous solution, suspension, or dispersion of the precursor compound is irradiated under ambient conditions for a time sufficient for the desired reactions to occur. It would be clear to one of skill in the art that suitable irradiation times can be varied depending on a number of factors such as intensity of the irradiation and the area or volume being irradiated. An exemplary suitable time for the irradiation can be 0.5 minutes to 5 minutes.

Conveniently, the precursor compound can be irradiated in the presence of a polarized olefin, which can react with generated o-quinone methide (e.g., an o-naphthoquinone methide) in a hetero-Diels-Alder reaction. For embodiments in which the precursor compound is irradiated in the presence of the polarized olefin, the substrate (i.e., the surface of which is attached to the precursor compound or the polarized olefin) can be pattern-wise irradiated to provide a pattern-wise labeled surface of the substrate.

o-Quinone Methide.

Irradiation of the precursor compound can generate an o-quinone methide having the formula:

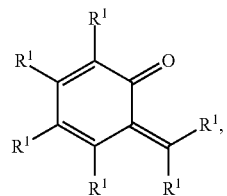

Formula IV wherein each $R^1$ is independently H, halogen, or an organic group, with the proviso that at least one $R^1$ includes a detectable label or a linker group attached to a surface of a substrate. Optionally, two or more $R^1$ groups may be combined to form one or more rings (e.g. to form an o-naphthoquinone methide or an o-anthraquinone methide). In certain preferred embodiments, the o-quinone methide is an o-naphthoquinone having one of the formulas:

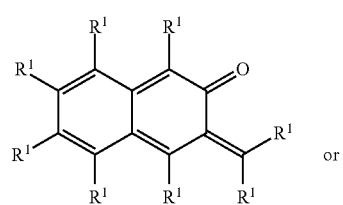

Formula Va or

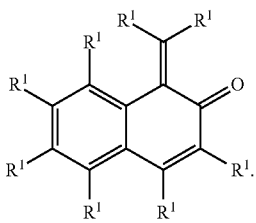

Formula Vb

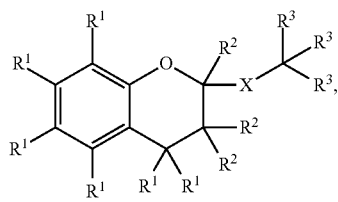

Formula VI

When $R^1$ represents an organic group, preferably the organic group is a carbon-bound (i.e., the bond to the group is to a carbon atom of the organic group) organic group. In certain embodiments, the organic group is an aliphatic group such as a C1-C20 aliphatic group, in some embodiments a C1-C10 aliphatic group, and in some embodiments a C1-C10 hydrocarbon moiety.

Polarized Olefin

The o-naphthoquinone methide can react with a polarized olefin in a hetero-Diels-Alder reaction. Suitable polarized olefins are, for example, of the formula:

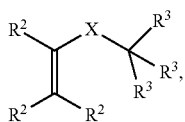

Formula III wherein each $R^2$ is independently H or an organic group; each $R^3$ is independently H, halogen, or an organic group; and X is O or $NR^4$, wherein $R^4$ is H or an organic group. In some embodiments, at least one $R^2$, $R^3$, or $R^4$ includes a linker group attached to the surface of the substrate. In some other embodiments, at least one $R^2$, $R^3$, or $R^4$ includes a detectable label.

When $R^2$, $R^3$, or $R^4$ represents an organic group, preferably the organic group is a carbon-bound (i.e., the bond to the group is to a carbon atom of the organic group) organic group. In certain embodiments, the organic group is an aliphatic group such as a C1-C20 aliphatic group, in some embodiments a C1-C10 aliphatic group, and in some embodiments a C1-C10 hydrocarbon moiety.

Hetero-Diels-Alder Adduct

The o-quinone methide disclosed herein can react with a polarized olefin in a hetero-Diels-Alder reaction. Conditions effective for the hetero-Diels-Alder reaction include contacting the o-quinone methide (e.g., an o-naphthoquinone methide) and the polarized olefin in an aqueous solution, suspension, or dispersion, typically under ambient conditions. As used herein, an aqueous solution, suspension, or dispersion is intended to include liquids that include, but are not limited to, water. Thus, aqueous liquids can also include, for example, organic solvents such as acetonitrile.

A hetero-Diels-Alder reaction of the o-quinone methide disclosed herein with a polarized olefin can form an adduct having the formula:

wherein each $R^1$ is independently H, halogen, or an organic group; each $R^2$ is independently H or an organic group; each $R^3$ is independently H, halogen, or an organic group; and X is O or $NR^4$, wherein $R^4$ is H or an organic group. Optionally, two or more $R^1$ groups may be combined to form one or more rings. Optionally, two or more $R^2$ groups may be combined to form one or more rings. Optionally, two or more $R^3$ and/or $R^4$ groups may be combined to form one or more rings. In certain preferred embodiments, the hetero-Diels-Alder reaction of an o-naphthoquinone methide disclosed herein with a polarized olefin can form an adduct of one of the formulas:

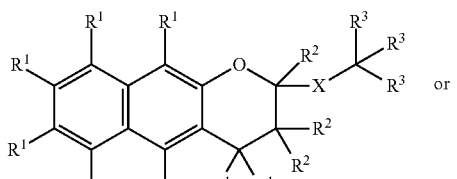

Formula VIIa or

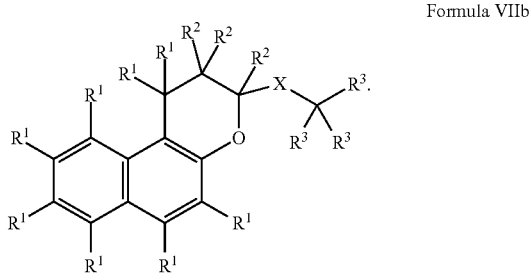

Formula VIIb

When $R^1$, $R^2$, $R^3$, or $R^4$ represents an organic group, preferably the organic group is a carbon-bound (i.e., the bond to the group is to a carbon atom of the organic group) organic group. In certain embodiments, the organic group is an aliphatic group such as a C1-C20 aliphatic group, in some embodiments a C1-C10 aliphatic group, and in some embodiments a C1-C10 hydrocarbon moiety.

In some embodiments, at least one $R^1$ includes a linker group attached to the surface of the substrate, and at least one $R^2$, $R^3$, or $R^4$ includes a detectable label, thus providing a label attached to the surface of the substrate. For embodiments in which $R^3$ or $R^4$ includes the detectable label, the detectable label can optionally be removed from the surface of the substrate by hydrolyzing the C—X bond.

In some other embodiments, at least one $R^1$ includes a detectable label and at least one $R^2$, $R^3$, or $R^4$ includes a linker group attached to the surface of the substrate, thus providing a label attached to the surface of the substrate. The detectable label can optionally be removed from the surface of the substrate by hydrolyzing the C—X bond.

The following examples are offered to further illustrate various specific embodiments and techniques of the present disclosure. It should be understood, however, that many variations and modifications understood by those of ordinary skill in the art may be made while remaining within the scope of the present disclosure. Therefore, the scope of the disclosure is not intended to be limited by the following examples.

Example 1

The light-induced click reaction for ligation of various molecules is based on the photochemical generation of o-napthoquinone methides in aqueous solution from 3-hydroxy-2-naphthalenemethanol precursor. The naphthyl chromophore allows for the activation using longer wavelength light (300-350 nm) and holds advantage over o-benzoquinone methide precursors such as o-hydroxybenzyl alcohol. Irradiation of 3-hydroxy-2-naphthalenemethanol chromophore (2) results in efficient dehydration of the substrate and the formation of o-naphthoquinone methide (oNQM) 1 (FIG. 1). In the presence of vinyl ethers (3) or enamines (4), oNQMs undergo very rapid Diels-Alder cycloaddition to yield substituted 2-alkoxy-3,4-dihydro-2H-naphtho[2,3-b]pyran (5) or 2-alkylamino-3,4-dihydro-2H-naphtho[2,3-b]pyran (6) as shown in FIG. 1. Various substituents can be introduced in aromatic rings of 2 and in vinyl component (3, 4) to serve as linker to substrates of interest (FIG. 1). In the absence of vinyl ethers, enamines, or other trapping agents o-quinone methides add water to regenerate the starting material.

Figure 2:
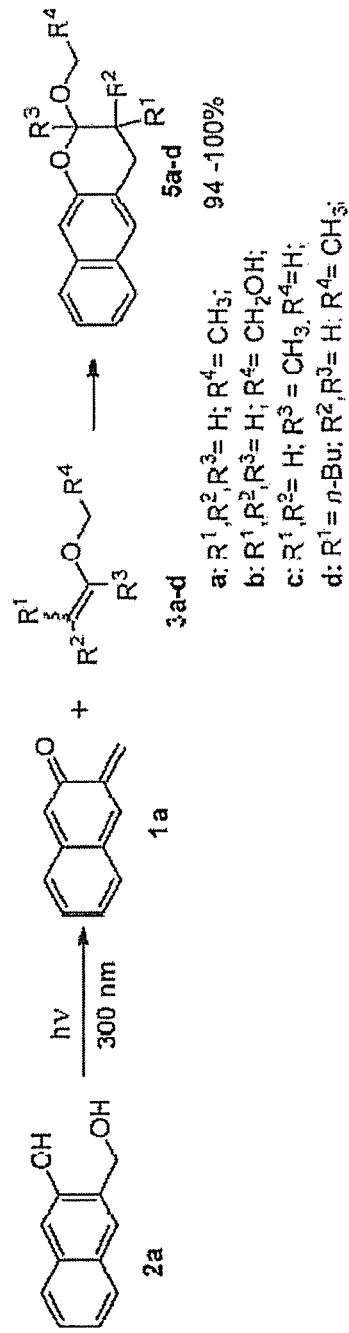
Figure 3:
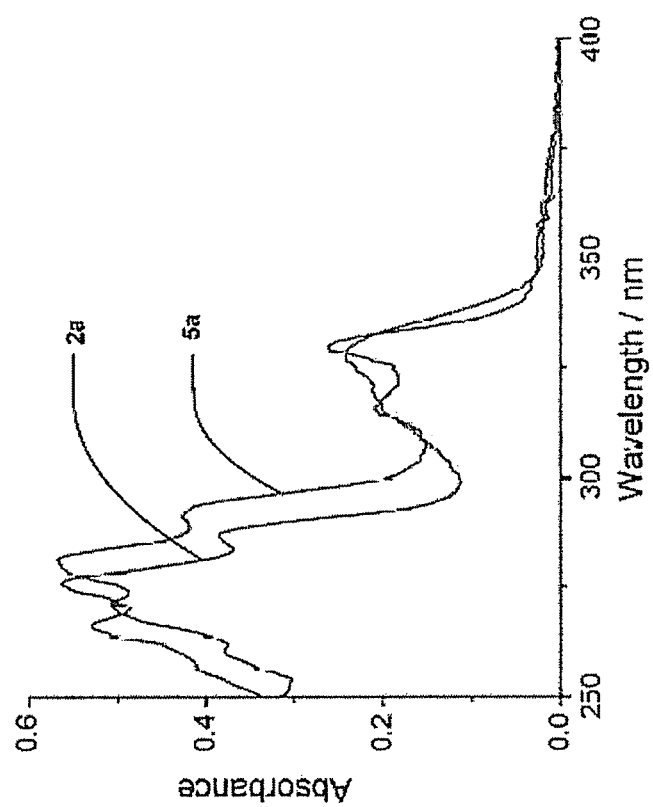
FIG. 3 illustrates the ultraviolet (UV)-spectra of approximately $10^{-4}$ M solutions of 3-hydroxy-2-naphthalenemethanol (2a) and adduct 5a in (1:1) acetonitrile-water mixture.

Photophysical properties, generation, and reactivity of oNQMs are discussed on the example of 3-hydroxy-2-naphthalenemethanol 2a (R'=H, FIG. 2). UV spectra of 3-hydroxy-2-naphthalenemethanol (2a) resemble the spectrum of 2-naphthol and contains two major absorption bands above 210 nm: at $\lambda_{max}$=275 nm (log ϵ=4.06 and at $\lambda_{max}$=324 nm (log ϵ=3.70, FIG. 3). Both bands show pronounced vibrational structure. 2a also show strong fluorescence with quantum yield of $\Phi_{F1}$=0.230±0.002 and generates the quinine methide with quantum yield 0.20±0.2. The emission spectra of 2a in aqueous solutions contain two major bands at 360 nm and 423 nm. The fluorescence life-time is $\tau_{FL}$~7 ns. While the emission spectra and fluorescent quantum yields of 2a resemble that of 2-naphthol ($\Phi_{F1}$=0.27) (J. B. Birks, Photophysics of Aromatic Molecules. Wiley Interscience, New York, 1970, 703 p; Datta et al., Spec. Acta A, 2006, 64, 11), the fluorescence life-time is somewhat shorter than for 2-naphthol ($\tau_{FL}$~11 ns) (Wang et al., J. Org. Chem. 2002, 67, pp 2429; Berlman, I. B. Handbook of Fluorescence Spectra of Aromatic Molecules. Academic Press, New York, 1971, 473 p). This observation apparently indicates that a new pathway for the excited state decay is opened for 2a.

Irradiation at 300 nm of 3-hydroxy-2-naphthalenemethanol (2a) results in the generation of oNQM 1a, which undergoes rapid hetero-Diels-Alder addition to ethyl vinyl ether (3a) to produce quantitative yield of 2-ethoxynaphthochroman 5a. The bimolecular rate of this reaction in aqueous solution was measured to be $4.07 \times 10^4 M^{-1}s^{-1}$. (Arumugam et al, J. Am. Chem Soc. 2009, 131, 11892). In the absence of vinyl ether moieties, oNQM undergoes very efficient re-hydration ($\tau Z_{H2O}$ (1a)=7.4 ms) to generate the starting material and no detectable new products are observed. It is important to note that high yield of hetero-Diels-Alder adducts is achieved despite the presence of more than a thousand-fold excess of a nucleophilic solvent. This observation indicates that addition of ethyl vinyl ether to oNQMs is at least two orders of magnitude faster than a hydration reaction. The hetero-Diels-Alder adducts are formed almost quantitatively even at the low conversion. In order to check the utility of the photo click for the biological application, the photochemistry was also investigated using 350 nm wavelength light. The reaction is clean at 350 nm as observed in the case of 300 nm photolysis. The only difference is the extinction coefficient of the chromophore at 350 nm is relatively less than that at 300 nm and therefore it either requires higher concentration of the oNQM precursor or longer irradiation time to obtain similar chemical yields.

Figure 4:
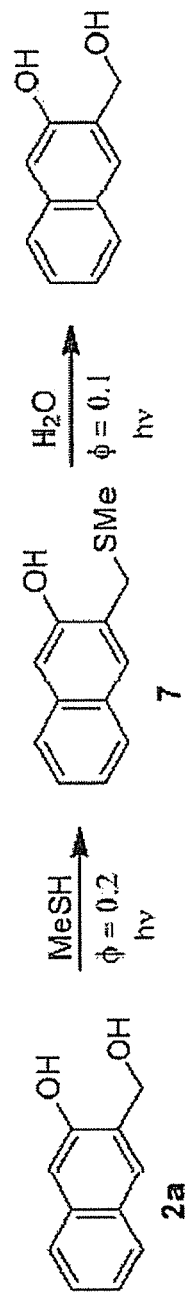
FIG. 4 is a schematic illustration of embodiments of the generation of an o-naphthoquinone methide by irradiation of a precursor compound, followed by trapping of the o-naphthoquinone methide by methyl thiol.

The oNQMs can also be can be intercepted by reactive nucleophiles such as azide anion and thiols. Our previous report on the kinetics of oNQM clearly demonstrates that the second order rate constant of thiol addition with oNQM is $\sim 1 \times 10^5 M^{-1}s^{-1}$ (Arumugam et al., J. Am. Chem. Soc. 2009, 131, 11892), which is twice as that of hetero-Diels-Alder reaction with vinyl ethers. The thiol ether thus formed is equally stable in both acidic and basic condition. Recently, this property had been utilized for quinone methide based protein affinity labeling. (Jiang et al., ChemBioChem. 2009, 10, 635). However, the thiol ether is photo active and regenerates the oNQM that can undergo hydration to yield the diol as shown in FIG. 4. Though our quantum yield experiments on methyl thio ether analogue of 3-hydroxy-2-naphthalenemethanol indicates that the efficiency of oNQM generation is relatively less compared to the photo-dehydration from the diol 2a, the yield of ligation will depend on the time of irradiation. Besides, the high nucleophilicty of thiols makes it less orthogonal in the presence of other electron deficient carbons.

On other hand, 2-ethoxynaphthochroman 5a is photochemically stable and shows no decomposition even after prolonged irradiation at 254, 300 nm or 350 nm. The stability of 5a was measured in aqueous solution at pH~7, 0.1N aqueous sodium hydroxide solution, and 0.1N aqueous perchioric acid for the 24 h period. HPLC analysis indicates that there are no changes in the concentration of 5a in aqueous solution of neutral pH and 0.1N aqueous sodium hydroxide solution. This observation clearly demonstrates that 5a is stable under neutral or basic conditions. 5a undergoes slow hydrolysis (life time τ~9.5 h) in aqueous solution of perchloric acid of pH 1 to produce 2-hydroxynapthochroman (5e, FIG. 5). Besides, vinyl ethers are stable at ambient conditions and do not react in the dark.

TABLE 1

Chemical yields of hetero-Diels-Alder adducts and the hydration product (2a) upon photolysis of 3-(ethoxymethyl)-2-naphthalenol 2c in the presence of various olefins 8-12.[a, b]

| Olefins | Chemical yield of 2a (% conversion) | Chemical yield of the hetero-Diels-Alder adduct (% Conversion) |
|---|---|---|
| 3a | 0 (15) | 97 ± 2 (15) |
|  | 0 (>99) | 96 ± 2 (>99) |
| 3a + 8-12 | 0 (>99) | 97 ± 2 (>99) |
| 8 | 97 ± 2 (14) | 0 (14) |
|  | 71 ± 3 (89) | 0 (89) |
| 9 | 93 ± 2 (14) | 0 (14) |
|  | 69 ± 3 (87) | 0 (87) |
| 10 | 94 ± 2 (14) | 0 (14) |
|  | 73 ± 2 (90) | 0 (89) |
| 11 | 96 ± 2 (14) | 0 (14) |
|  | 71 ± 2 (92) | 0 (89) |
| 12 | 95 ± 2 (14) | 0 (14) |
|  | 71 ± 2 (85) | 0 (89) |

[a][Olefin] = 100 mM; [oNQM precursor] = 1 mM.
[b]Irradiation wavelength = 300 nm.

To examine the selectivity of the reaction of oNQM with various olefins, two set of experiments were carried out. First, 1 mM solution of oNQM precursor 2c was irradiated in the presence 0.1 M of ethyl vinyl ether (3a) and equal amounts (0.1 M each) of olefins 8-12 in 50% aqueous acetonitrile. HPLC analysis showed that only adduct 5a has been formed in excellent yields (FIG. 6) and the result are presented in Table 1. Among vinyl ethers, oNQM reacts only with aliphatic ether but does not form cycloaddition product with aromatic vinyl ether, such as 12.

Figure 6:
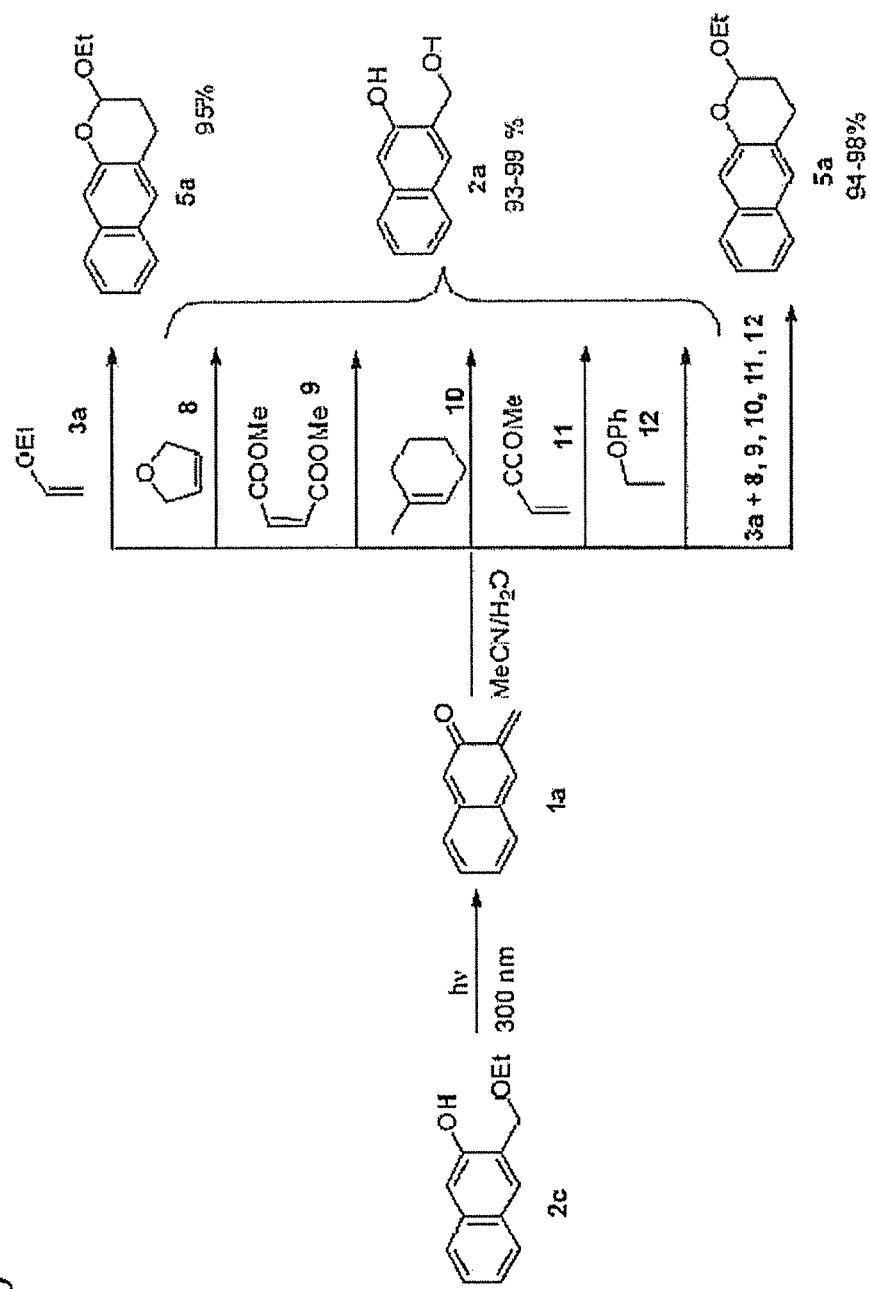
FIGS. 6 and 7 are schematic illustrations of embodiments of the generation of an o-naphthoquinone methide by irradiation of a precursor compound, followed by a selective hetero-Diels-Alder reaction with polarized olefins to form hetero-Diels-Alder adducts.

Next, oNQM 1a was generated by 300 nm photolysis of 1 mM solutions of 3-(ethoxymethyl)-2-naphthalenol (2c) in 50% aqueous acetonitrile in the presence of 0.1 M of various olefins. The following olefins have been tested: ethyl vinyl ether (3a), 2,5-dihydrofuran (8), dimethyl maleate (9), 1-methylcyclohexene (10), methyl acrylate (11), and phenyl vinyl ether (12). Only in the presence of 3a, the formation of the quantitative yields of the hetero-Diels-Alder adduct 5a was observed both at lower and higher conversion. In all other cases, the only product of reaction was 3-hydroxy-2-naphthalenemethanol (2a), and no adducts of 1a to alkenes 8-12 were detected (FIG. 6). HPLC analysis reveals the quantitative formation of hydration product 2a in the latter cases (Table 1) at lower conversion. At higher conversion the yield of hydration product is some what reduced due to possible oligomerization of oNQM. However no cyclo-addition product is observed, which suggests that the hydration of 1a is much faster than reaction of 1a with olefins 8-12. Whereas, the hetero-Diels-Alder reaction adduct formation is the major reaction in the presence of 3a. These set of experiments clearly show that o-quinone methides are selective towards electron rich polarized alkenes, such as vinyl ether 3a.

TABLE 2

Rate of decay of 2, 3 NQM in the presence of various olefins (0.04M) in 50% phosphate buffer + 50% MeCN aqueous solution.

| Olefin | Pseudo first order rate constant of 2, 3 NQM ($s^{-1}$) |
|---|---|
| 50% Phosphate Buffer + 50% | 119 ± 6 |
| 3a | 2703 ± 55 |
| 8 | 125 ± 9 |
| 9 | 118 ± 4 |
| 10 | 123 ± 7 |
| 11 | 121 ± 8 |

Also, The rate of disappearance of 1a in wholly aqueous solutions in the presence of 0.04 M of the following olefins: ethyl vinyl ether (3a), 2,5-dihydrofuran (8), dimethyl maleate (9), 1-methylcyclohexene (10) and methyl acrylate (11) were examined. It was found that only in the presence of 3a, the rate of decay was significantly enhanced (Table 2). In all other cases, the rate of decay was equal to the rate observed in neat water. This observation clearly indicates that only the reaction of oNQM with ethyl vinyl ether is able to compete with the hydration of oNQM. Whereas, in the case of non-polarized olefins and electron poor polarized olefins, the hydration reaction is the only reaction observed. This observation further confirms that o-quinone methides are very selective towards electron rich polarized olefin. Kinetic studies with olefin 12 can not be followed as it has substantial absorption at the excitation wavelength (266 nm). Also, oNQM readily reacts with the wide range of aliphatic vinyl ethers carrying various substituents at oxygen, α-carbon, and β-carbon atoms. For example, oNQM 1a was photochemically generated from 2a in the presence or 2-hydroxy ethyl vinyl ether (3b), isopropenyl methyl ether (3c), or 1-ethoxyhept-1-ene (3d). The corresponding photoproducts 5b-d were isolated in high yield and fully characterized. HPLC analysis of reaction mixtures confirmed nearly quantitative yields of adducts 5b-d in all three cases (Table 3).

TABLE 3

Chemical yield of the DA adduct upon photolysis 2a in the presence of various vinyl ethers in 50% MeCN in 0.01N aqueous phosphate buffer solution.[a, b]

| Olefin | Chemical yield of the DA adduct (% conversion) |
|---|---|
| 3a | 96 ± 2 (>99) |
| 3b | 94 ± 2 (>99) |
| 3c | 95 ± 3 (>99) |
| 3d | 97 ± 2 (>99) |

[a] [Olefin] = 1.5 mM; [oNQM precursor] = 1 mM.
[b] Irradiation wavelength = 300 nm.

TABLE 4

Rate of decay of 2, 3 NQM in the presence of various vinyl ethers (0.05M) in 50% MeCN in 0.01N aqueous phosphate buffer solution.

| Olefin | Pseudo first order rate constant of 2, 3 NQM ($s^{-1}$) |
|---|---|
| 3a | 3100 ± 121 |
| 3b | 3050 ± 75 |
| 3c | 3080 ± 101 |
| 3d | 3090 ± 66 |

The rate of reaction of oNQM 1a with vinyl ethers 3b-d was determined using laser flash photolysis and was found to be very similar to that of ethyl vinyl ether 3a (Table 4). This observation indicates that variation of substitution at oxygen, α-carbon, and β-carbon atoms does not significantly affect the rate of the cycloaddition reaction.

Figure 7:
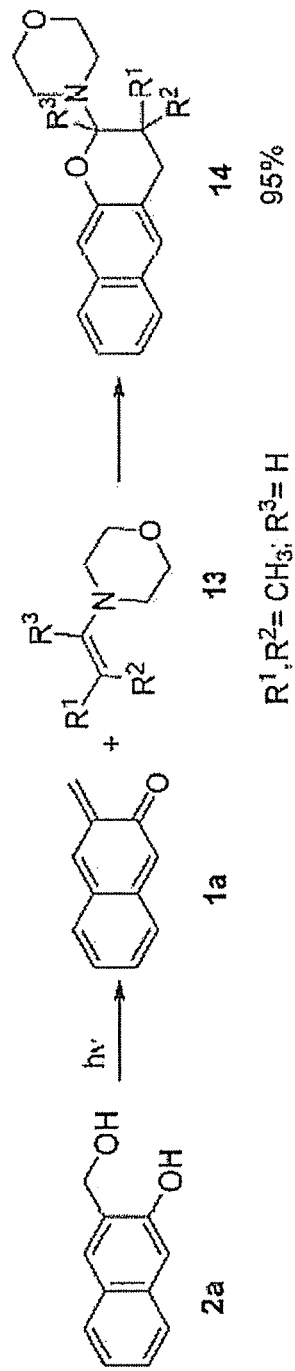
Figure 8:
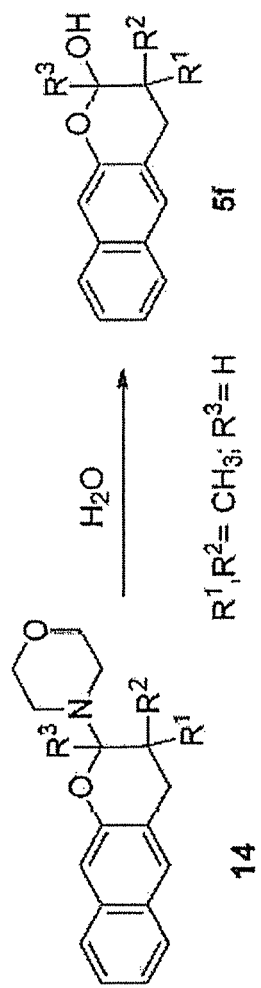
FIG. 8 is a schematic illustration of the hydrolysis of an exemplary hetero-Diels-Alder adduct.

Photochemically-generated oNQM 1a also rapidly reacts with enamine 13 also results in quantitative formation of the adduct 14 (FIG. 7). In aqueous solutions adduct 14 undergoes rapid hydrolysis of the amino substituent to produce 3,4-dihydro-2-hydroxy-3,3-dimethyl-2H-Naphtho[2,3-b]pyran (5f, FIG. 8). The life-time of 14 at pH ~7 in wholly aqueous solution is τ=21.2±0.6 minutes.

Figure 9:
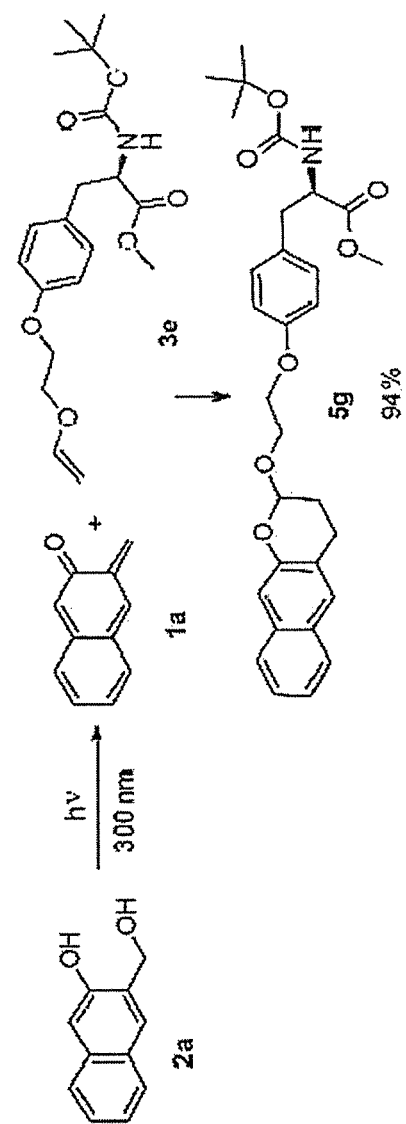
FIGS. 9, 10, and 11 are schematic illustrations of embodiments of the generation of an o-naphthoquinone methide by irradiation of a precursor compound, followed by a hetero-Diels-Alder reaction with polarized olefins to form hetero-Diels-Alder adducts.

For the photo-ligation purposes the payload can be attached to the oxygen, α-carbon, and β-carbon atoms of the vinyl ether 3 (FIG. 2). For example, we have prepared vinyl ether 3e, which is conjugated to a protected amino acid tyrosine via ethylene glycol linker (FIG. 9). Irradiation of the precursor 2a in the presence of 3e resulted in the rapid and quantitative formation of the ligation product 5g (FIG. 9). The adduct 5g was isolated in 94% yield and fully characterized.

Figure 10:
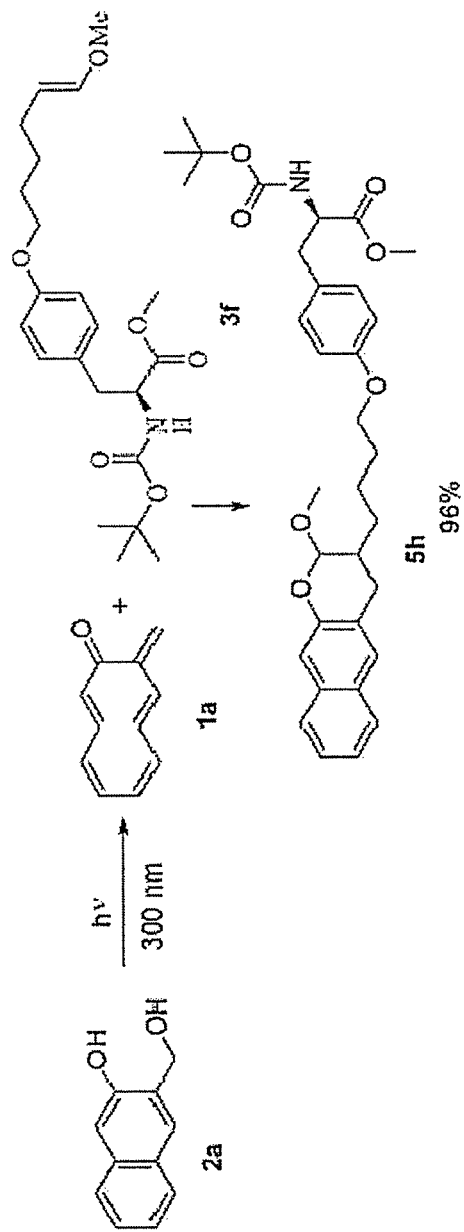

The strategy described above allows ligation of payloads through oxygen atom of vinyl ethers, which can be detached by acid hydrolysis at pH 1. For the application that requires permanent conjugation, the pay load is attached through β-carbon of vinyl ethers. For illustrative purpose, tyrosine was attached to β-carbon of the vinyl ether 3f through a short linker as shown in FIG. 10. As observed in the first approach, irradiation of the precursor 2a in the presence of the 1.5 equivalents of vinyl ether 3f resulted in the quantitative formation of the ligation product (FIG. 10). Thus it has been clearly demonstrated that vinyl ether system provides dual mode of ligation, one mode allows conjugation via acid labile C—O bond and another mode allows ligation via permanent C—C bond.

Figure 11:
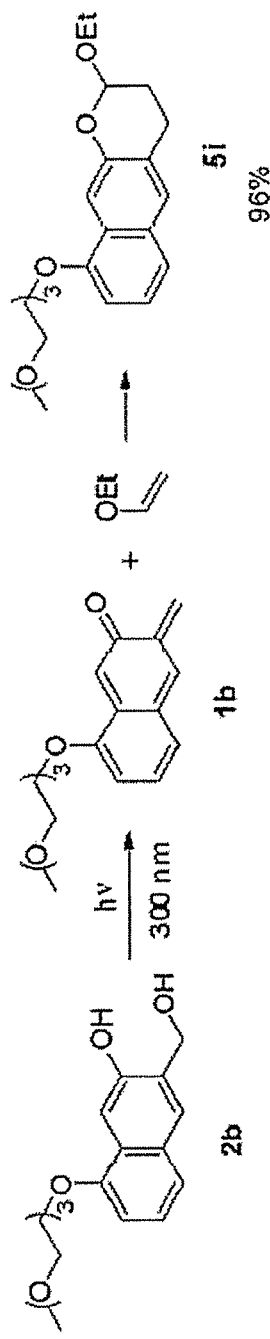

The second component for the ligation can be attached to the naphthalene ring of the precursor 2 via an appropriate linker (FIG. 1). For example, we have prepared 3-hydroxy- 2-naphthalenemethanol modified at 8-position of a naphthalene ring with a tri-ethylene glycol linker (2b, FIG. 11). Upon irradiation of this precursor in the presence of ethyl vinyl ether (3a) in aqueous solution, the adduct 5h of the corresponding oNQM 1b to 3a is Ruined quantitatively (Table 5). This product was isolated in 96% yield and fully characterized.

TABLE 5

Chemical yields of ligation products upon photolysis of oNQM precursors 2a-b in the presence of various vinyl ethers in 50% MeCN in 0.01N aqueous phosphate buffer solution.[a, b]

| Olefin | oNQM Precursor | Ligation Product | Chemical yield of the ligation product (% conversion) |
|---|---|---|---|
| 3e | 2a | 5g | 94 ± 4 (>99) |
| 3f | 2a | 5h | 96 ± 2 (>99) |
| 3a | 2b | 5i | 96 ± 2 (>99) |

[a][Olefin] = 1.5 mM; [oNQM precursor] = 1 mM.
[b]Irradiation wavelength = 300 nm.

Figure 14:
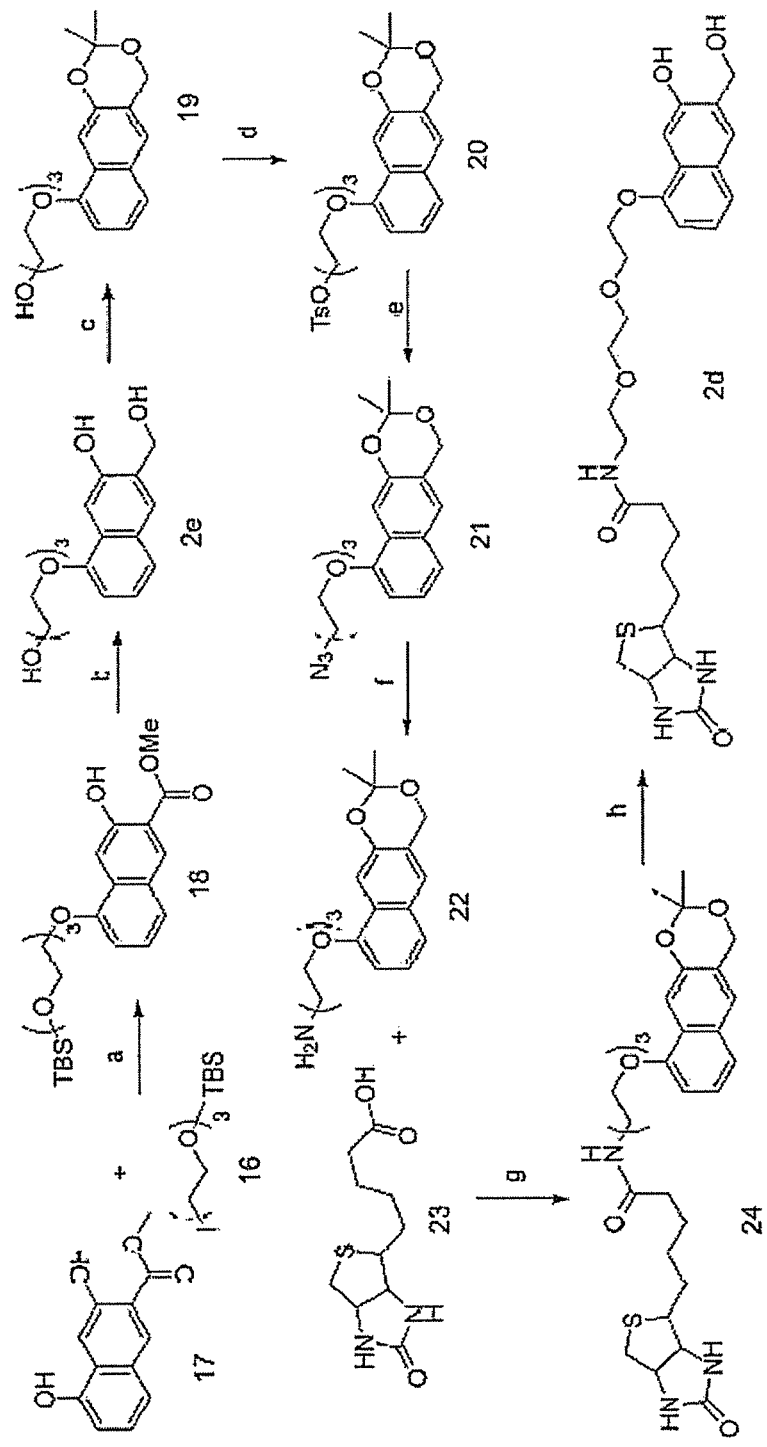
FIG. 14 is a schematic illustration for an exemplary method for preparing an embodiment of a precursor compound. Reagents and conditions: (a) $K_2CO_3$, acetone, reflux, 65%; (b) $LiAlH_4$, THF, 92%; then aqueous $HF/CH_3CN$, 85% over 2 steps; (c) TsOH, 2,2-dimethoxypropane, acetone, 90%; (d) TsCl, pyridine, DCM, 82%; (e) $NaN_3$, DMF, 60° C., 80%; (f) $LiAlH_4$, $Et_2O$, 85%; (g) EDC, DMAP, DMF, 83%; (h) Amberlyst-15, methanol, room temperature, 95%.
Figure 15:
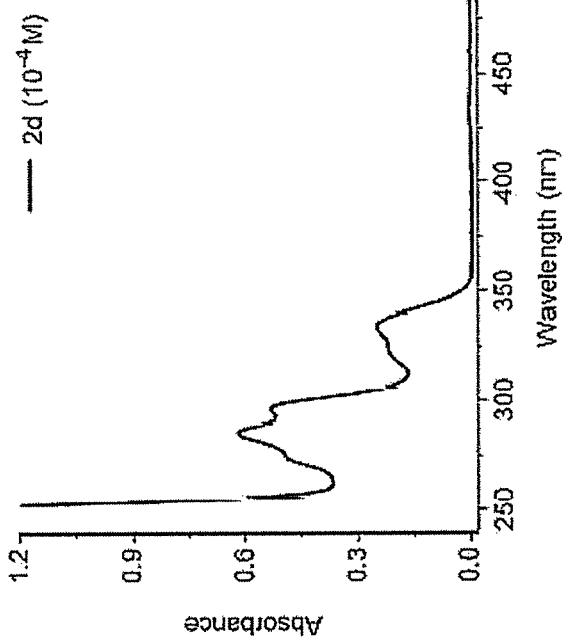
FIG. 15 illustrates the ultraviolet (UV)-spectra of the biotin—3-hydroxy-2-naphthalenemethanol conjugate 2d.

We have also shown that triethyleneglycol-derivatized 3-hydroxy-2-naphthalenemethanol can be further linked to biotin, producing the biotin—3-hydroxy-2-naphthalenemethanol conjugate 2d illustrated in FIG. 14. The UV Spectra of the biotin—3-hydroxy-2-naphthalenemethanol conjugate 2d is illustrated in FIG. 15.

In summary, we have demonstrated a very facile and selective photo-activatable click reaction that has high potential utility for light-triggered bioconjugation. The reaction is very selective towards electron rich polarized alkenes and demonstrates wide scope of reactivity that provides dual mode of ligation. The click tool compromising o-napthoquinone methides and vinyl ether system can be tailor made for a desired application depending on whether it requires ligation via labile C—O bond or permanent C—C bond. The selectivity of the click reaction can be useful in site specific labeling of biological system such as cell surface, proteins etc. Most importantly, the ligation can be achieved with very high spatial and temporal resolution due to the high rate of the reaction. The oNQM precursors and vinyl ethers are stable and do not react in the dark. High photostabilty of the hetero-Diels-Alder adduct completely allows for the elimination of secondary photochemistry after the click reaction. Currently in our lab, we have been investigating the utility of this click system as a technical tool for fluorescent labeling of biological systems and patterned immobilization of biomolecules on glass surface.

Example 2

Figure 16:
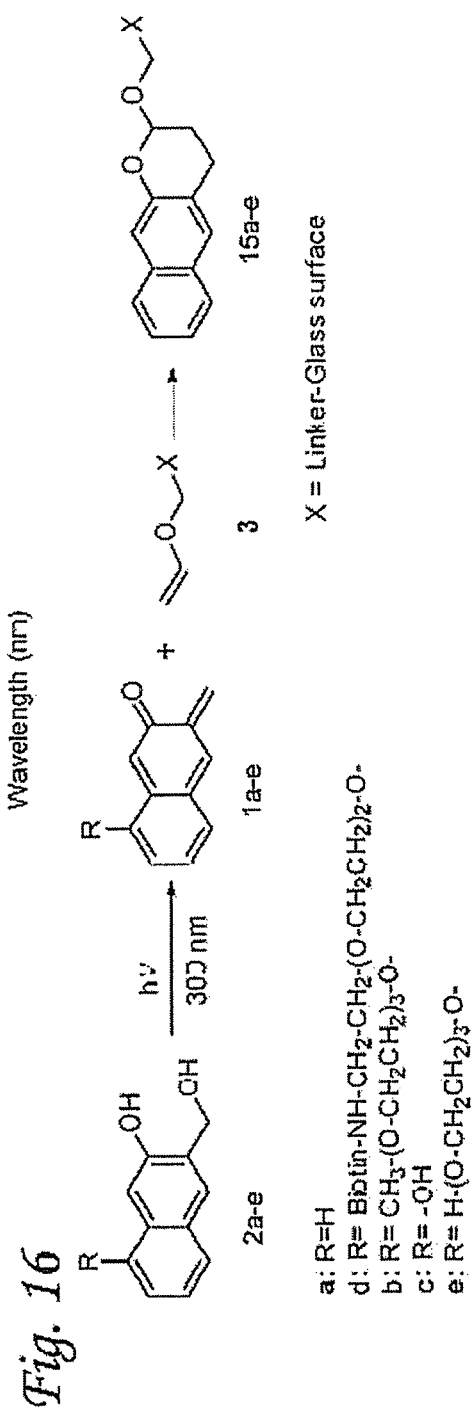
FIG. 16 is a schematic illustration of an embodiment of the generation of an o-naphthoquinone methide by irradiation of a precursor compound, followed by a hetero-Diels-Alder reaction with a polarized olefin to form a hetero-Diels-Alder adduct.

We envisaged that this photo-click reaction can be efficiently employed for the light-directed immobilization (patterning) of various substrates on the surface. For surface derivatization, one can adopt a conventional strategy that requires the oNQM precursor, 3-hydroxy-2-naphthalenemethanol derivative to be attached to the appropriate surface. Flood or patterned irradiation of such derivatized surface in the presence of a vinyl component carrying a payload substrate will result in immobilization of the latter. However, a more attractive from technological point of view immobilization/patterning method consists of the derivatization of the surface with vinyl ether moieties followed by the light directed attachment of substrates containing o-hydroxybenzyl alcohol or 3-hydroxy-2-naphthalenemethanol chromophore. (FIG. 16). Since the life-time of oNQM 1 in aqueous media is below 10 ms, diffusion of the photo-generated oNQM species from the site of irradiation is very limited. An example of the application of such technique is presented in this paper.

Figure 17:
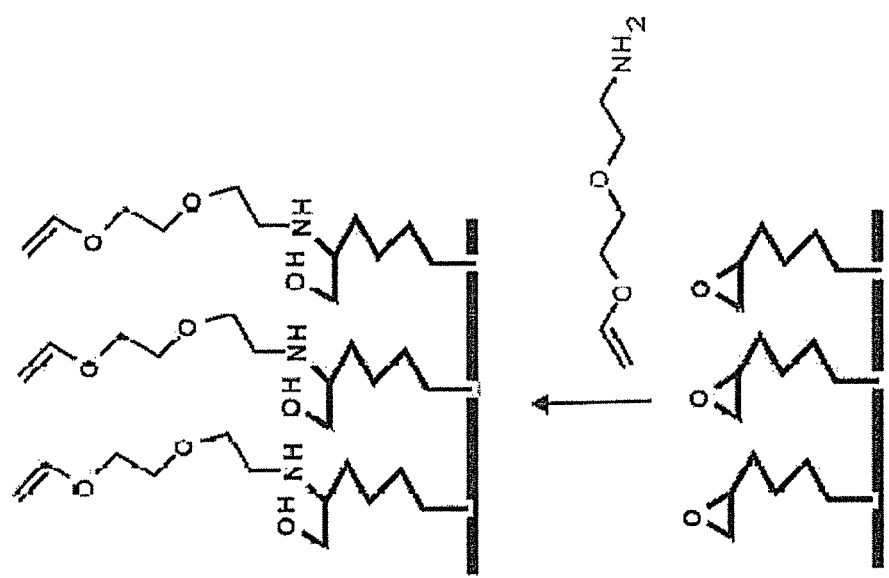
FIG. 17 is a schematic representation of an embodiment of the preparation of vinyl ether functionalized surface of a substrate (e.g., glass slides).

Commercial epoxide-functionalized glass slides were treated with 2-hydroxyethyl vinyl ether in the presence of catalytic amount of anhydrous p-toluenesulfonic acid or treated with 2-(2-(vinyloxy)ethoxy)ethanamine in dichloromethane at room temperature to yield vinyl ether functionalized glass surface. (FIG. 17). The resulting vinyl ether functionalized were covered with aqueous solution of containing biotin—3-hydroxy-2-naphthalenemethanol conjugate 2d ($1\times10^4$ M), and irradiated with fluorescent UV lamps. The glass slides clicked biotin in this fashion were stained with fluorescently labeled FITC-Avidin and washed thoroughly by sonicating the glass slide in phosphate buffer solution followed by overnight incubation in the fresh phosphate buffer solution. The aforementioned extensive washing was required to clean up non-specific binding of FITC-Avidin on the glass surface.

Figure 18:
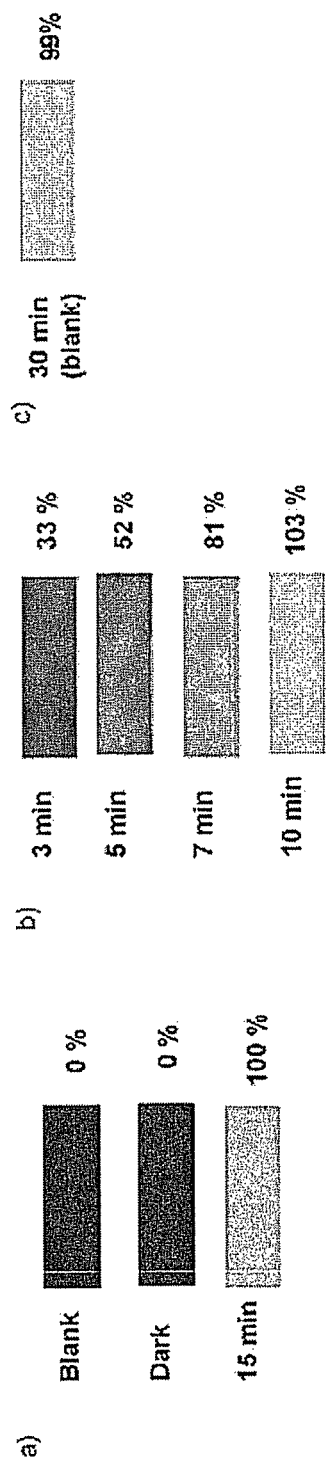
FIG. 18 illustrates embodiments showing FITC-Avidin stained biotinylated glass slides: (a) comparison of blank (vinyl ether slide) and dark reaction slide (vinyl ether slide incubated in aqueous biotin-conjugate solution in the dark) with flood irradiated slide (b) Biotinylated glass slides with different degree of functionalization (3-10 minutes photolysis) (c) Biotinylated slide (10 minutes sample) after 30 minutes exposure to 300 nm light in aqueous phosphate solution.

The degree of biotin functionalization as a function of irradiation time was monitored by following the fluorescence intensity of the resulting glass slides. The fluorescence intensity of the glass slide increases with the increase in irradiation time (using sixteen 8 W 300 nm lamps) up to 10 minutes and the intensity saturates upon further irradiation. The high intensity of fluorescence recorded from these slides after 10 minutes photolysis indicates high density of functionalization. The saturation of fluorescence upon further irradiation (e.g. 15 minutes) can be attributed to the complete functionalization of vinyl ether group and the photostabilty of the resulting hetero-Diels-Alder adduct. The photostabilty of the hetero-Diels-Alder adduct is further confirmed by the fact that the fluorescence intensity remains the same even after 30 minutes irradiation of 10 minutes biotinylated sample in plain aqueous phosphate solution. (FIG. 18).

Figure 19:
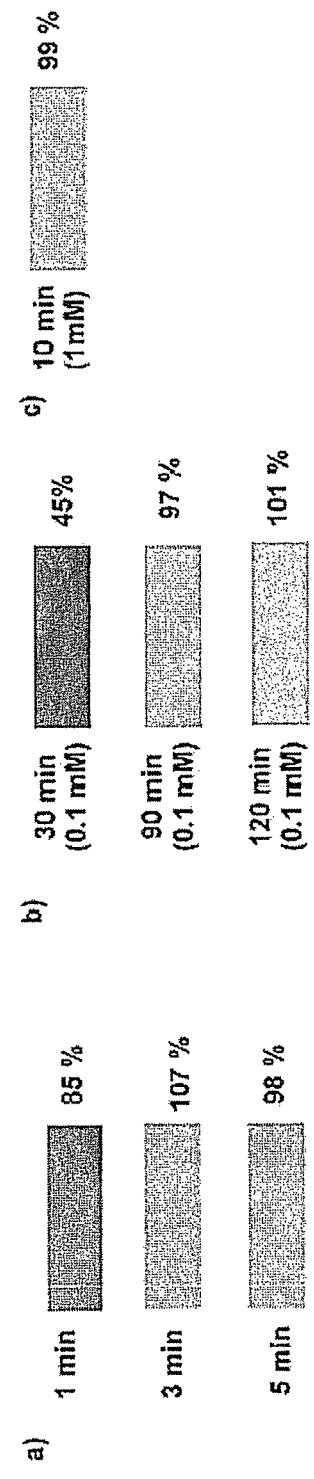
FIG. 19 illustrates embodiments showing FITC-Avidin stained biotinylated glass slides: (a) comparison of blank (vinyl ether slide) and dark reaction slide (vinyl ether slide incubated in aqueous biotin-conjugate solution in the dark) with flood irradiated slide (b) Biotinylated glass slides with different degree of functionalization (3-10 minutes photolysis) (c) Biotinylated slide (10 minutes sample) after 30 minutes exposure to 300 nm light in aqueous phosphate solution.

The irradiation time can be cut short in to 3 minutes by using medium pressure mercury lamp with 295 nm cut off glass filter. (FIG. 19). For practical applications, the utility of this reaction was also tested using 350 nm fluorescence lamps. Since the absorbance at 350 nm is low at experimental condition (0.1 mM, FIG. 15), either the substrate concentration should be increased to 1 mM or the irradiation should be increased to 90 minutes to get complete functionalization.

Figure 20:
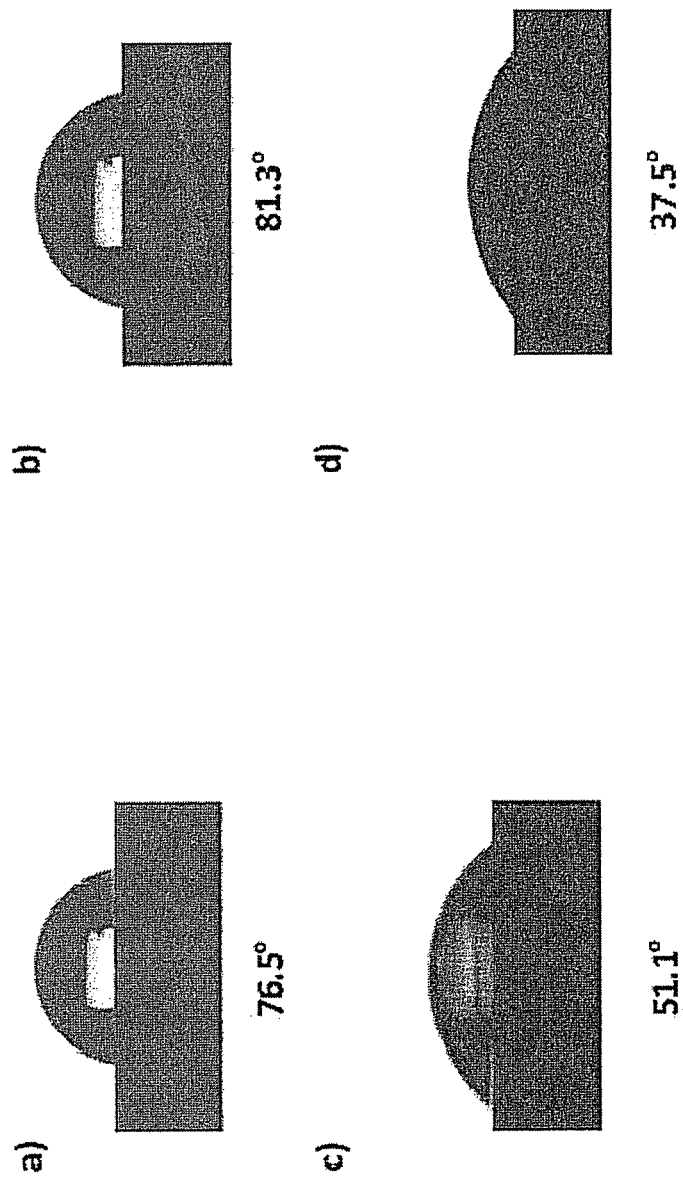
FIG. 20 illustrates embodiments showing water contact angles of functionalized: (a) vinyl ether glass slide; (b) vinyl ether glass slide after photo-click reaction 2a; (c) vinyl ether glass slide after photo-click reaction 2b; and (d) vinyl ether glass slide after photo-click reaction 2d.

The surface derivatization of vinyl ether functionalized glass surface with various oNQM precursors was also studied as a function of its wetability. The water contact angle measurements were made with vinyl ether functionalized glass surface and the same after photo click reaction with oNQM precursor 2a, 2b, and 2d. FIG. 20 clearly demonstrates that the wettabilty change is minimal after derivatization with 2a and shows appreciable change in the case of 2b and 2d. This change in wettabilty after photo-click with 2d and 2b can be attributed to increased hydrophillicity of the surface due to the derivatization of glass surface with triethylene glycol appended biotin and triethylene glycol monomethyl ether respectively. Table 6 presents the comparison of water contact angles of commercially available epoxide slides (VWR #66025-582) with the derivatized ones.

TABLE 6

Water contact angle measurements of glass slides with various functional groups.

| Functional groups | Water contact angle |
|---|---|
| Commercially available epoxide (VWR) | 91.0 ± 2.5 |
| Vinyl ether + hydroxy group from opened epoxide | 77.0 ± 2.2 |

TABLE 6-continued

Water contact angle measurements of glass slides with various functional groups.

| Functional groups | Water contact angle |
|---|---|
| 2a-vinyl ether adduct | 82.7 ± 1.9 |
| 2d-vinyl ether adduct | 38.0 ± 1.4 |
| 2b-vinyl ether adduct | 52.2 ± 1.5 |

Figure 21:
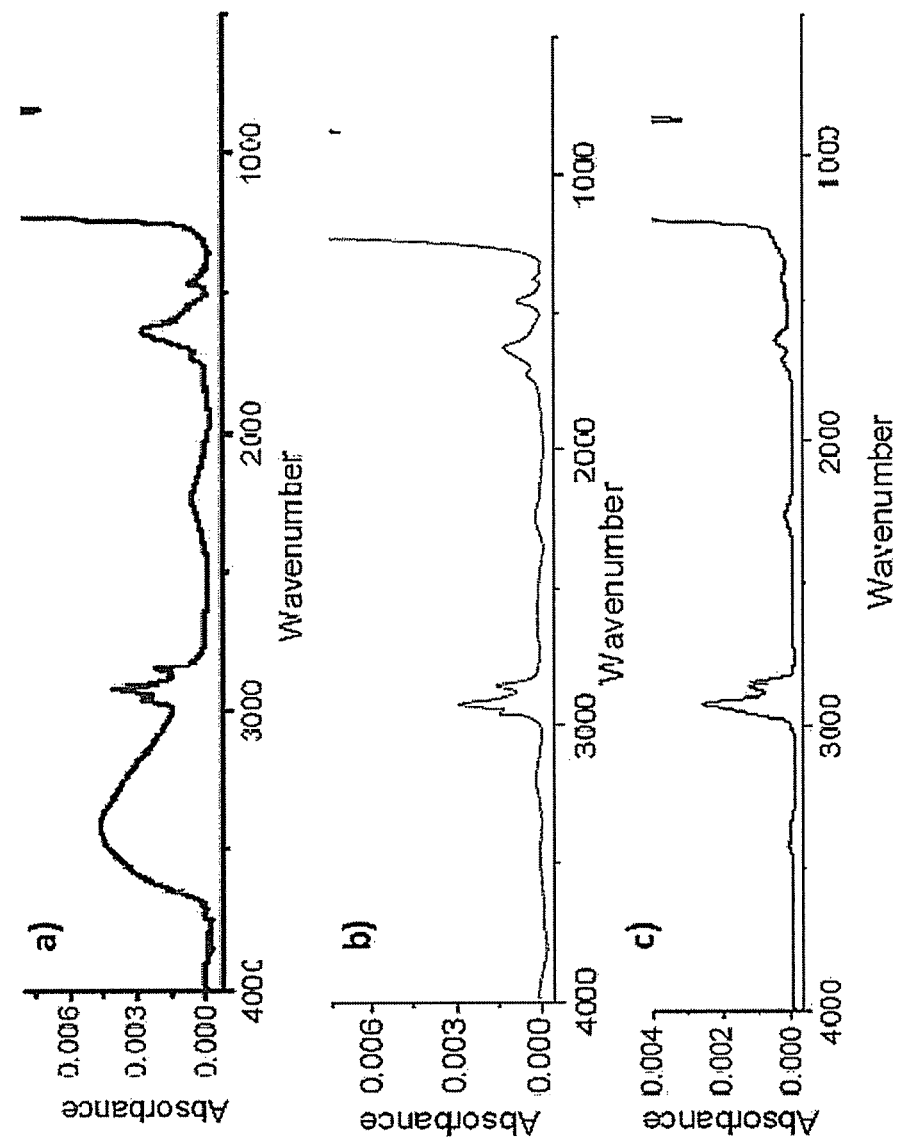
FIG. 21 illustrates Fourier transform infrared (FTIR) spectra for embodiments of functionalized glass surfaces: (a) vinyl ether glass slide after photo-click reaction 2c (b) vinyl ether glass slide after photo-click reaction 2a (c) vinyl ether glass slide.

Attempts were also made to follow the surface derivatization with FTIR spectroscopy. (FIG. 21). The region below the wavenumber 1300 cm$^{-1}$ is completely masked by high intensity signals corresponds to silicon oxide bond. In the case of vinyl ether deravatized glass surface, only the signal corresponds to C—H stretching was clearly observed. The other peaks were too low to identify any other functional groups. However after photo-click reaction with oNQM precursor 2c, a strong broad signal centered at 3440 corresponds to non-hydrogen bonded phenolic OH was observed. As expected, the broad signal at 3440 was not observed after photo-click with 2a. These experiments stands as an additional supporting evidence for the efficient derivatization of glass surface using oNQM based photo click reaction.

Figure 22:
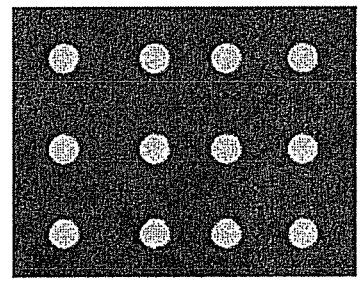
FIG. 22 illustrates embodiments showing patterned surface derivatization: (a) by prepositioning 2 µL drops of photoactive click reagents on the vinyl ether glass slide (b1) by placing the vinyl ether glass slide and irradiating through "UGA" mask (original scan) (b2) enlarged version of the original scan b1.
Figure 22:
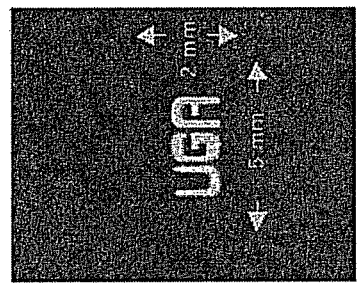
Figure 22:
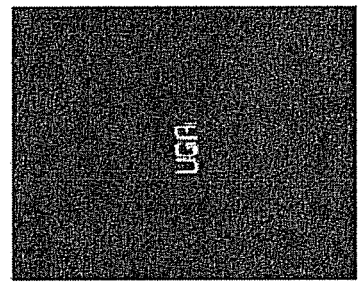

We have also tested two procedures for patterned functionalization of the slides. In the Method A, ca. 2 µL drops of the biotin-3-hydroxy-2-naphthalenemethanol conjugate 2d were placed on the vinyl ether-derivatized glass plate and irradiated with fluorescent UV lamp. The fluorescent image obtained after staining of the slide with fluorescently labeled FITC-Avidin, and washing is shown in FIG. 22a. In the Method B, the vinyl ether derivatized glass slide was placed into the solution, containing biotin—3-hydroxy-2-naphthalenemethanol conjugate 2d and irradiated through a "UGA" mask. The fluorescent image obtained after staining of the slide with fluorescently labeled FITC-Avidin, and washing is shown in FIG. 22b1.

As in the case of flood irradiated samples, the FITC-Avidin stained photo-clicked surfaces should be washed by sonicating the glass slides in phosphate buffer saline solution for 30 minutes followed by overnight incubation in fresh phosphate solution to avoid any non-specific binding of FITC-Avidin to glass surface. From technical point of view, a shorter washing procedure will enhance the efficacy of this photo-click system. This can be achieved by PEGlating the patterned biotin deravatized glass slides. For this purpose, the commercially available epoxide slide was treated with 2-(2-(vinyloxy)ethoxy)ethanamine (PEG 2 amine) to yield vinyl ether glass slide with PEG 2 functionality. This vinyl ether slide was taken for patterned surface derivataztion following the procedure described in Method A. The patterned photo-clicked glass slides thus obtained was flood irradiated in an aqueous solution oNQM precursor 2e containing PEG3-OH functionality and then stained with labeled FITC-Avidin. The patterned surface deravatized glass slide with labeled FITC-Avidin was incubated in phosphate saline solution for 1 hour and then scanned in variable mode Typhoon imager.

Figure 23:
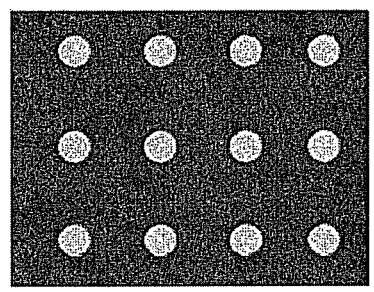
FIG. 23 illustrates embodiments showing patterned surface derivatization: by prepositioning 2 µL drops of the photoactive click reagent on the vinyl ether glass slide (a) washed for 1 hour without PEGlation before FITC-Avidin staining (b) washed for 6 hours without PEGlation before FITC-Avidin staining (c) washed for 16 hours without PEGlation before FITC-Avidin staining (d) washed for 1 hour with PEGlation before FITC-Avidin staining.
Figure 23:
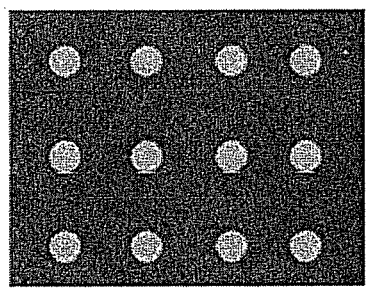
Figure 23:
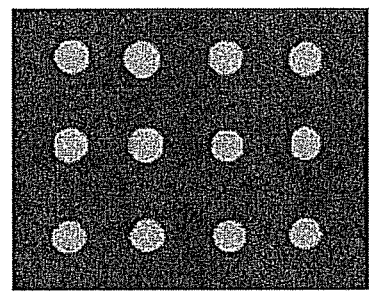
Figure 23:
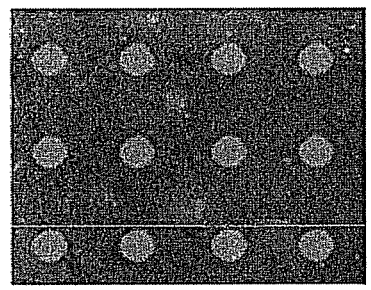

For comparative purposes, three more patterned biotin deravatized glass slides were prepared and stained with FITC-Avidin without PEGlation. (FIG. 23). The obtained FITC-Avidin labeled glass slides 1, 2 and 3 were incubated in phosphate buffer saline solution for 1 hour, 6 hours, and 16 hours respectively. FIG. 23d clearly demonstrates that PEGlation of patterned derivatized glass slides prevents non specific binding of FITC-Avidin and therefore a shorter washing procedure is enough for obtaining a clear pattern. Whereas longer washing duration (16 hours) was required to obtain similar pattern if the patterned derivatized surfaces are not PEGlated. FIGS. 23a and 23b demonstrates the non-specific binding of FITC-Avidin when non-PEGlated patterned derivatized surfaces are washed for shorter duration (1 hour and 6 hours.)

Figure 5:
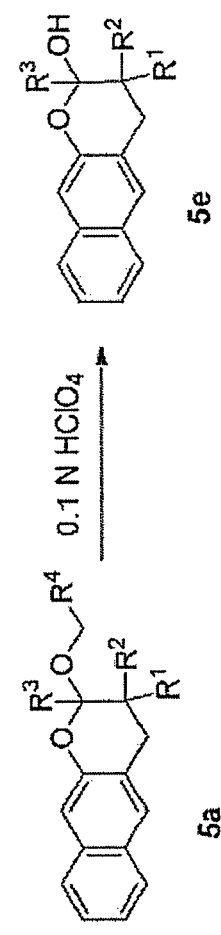
FIG. 5 is a schematic illustration of the hydrolysis of an exemplary hetero-Diels-Alder adduct under acidic conditions.
Figure 24:
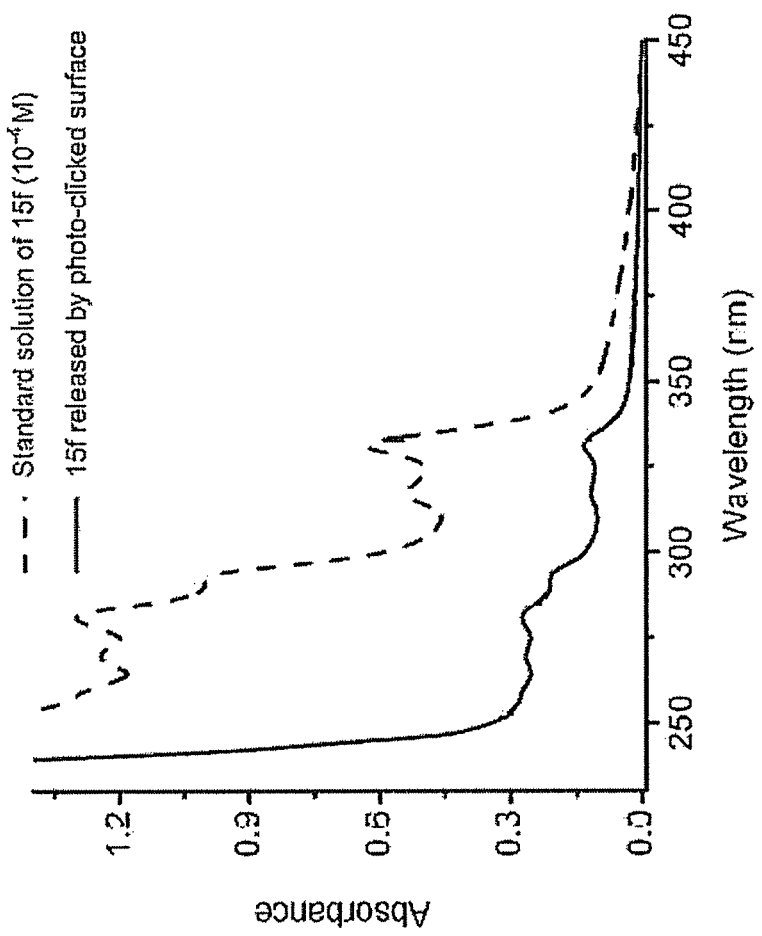
FIG. 24 is an illustration of UV-spectra of approximately $10^{-4}$ M solutions of 2-hydroxynaphthochroman (15f, dash line) and the solution 15f released by the photo-clicked surface upon dilute acid (0.1M) treatment (solid line) in (1:1) acetonitrile-water mixture.

In all aforementioned experiments, the vinyl ether functionality was appended to the glass surface through the oxygen atom. As shown in FIG. 5, the hetero-Diels-Alder adduct formed after photo-click reaction is acid labile and can be hydrolyzed at pH 1. This permits complete detachment of the molecules that are previously immobilized on the glass surface upon dilute acid treatment and thereby allows to measure the concentration of fluorophore that can be immobilized by this photo-click system. For this purpose a commercially available epoxide glass slide of known molecular density (VWR #16001-030, density=2×10$^{13}$ molecules per mm$^2$, surface area=1875 mm$^2$) was converted into vinyl ether functionalized glass slide and subsequently photo-clicked with oNQM 1a. The resulted photo-clicked surface that contains napthochroman 15a was then treated with 0.1N perchloric acid to trigger the release of 2-hydroxynaphthochroman 15f. The concentration of the released payload 15f was determined from its extinction coefficient at 281 nm by UV-Vis Spectroscopy (FIG. 24). It was calculated from three independent trials that about 70±4% of epoxide functionality were converted into payloads.

Figure 25:
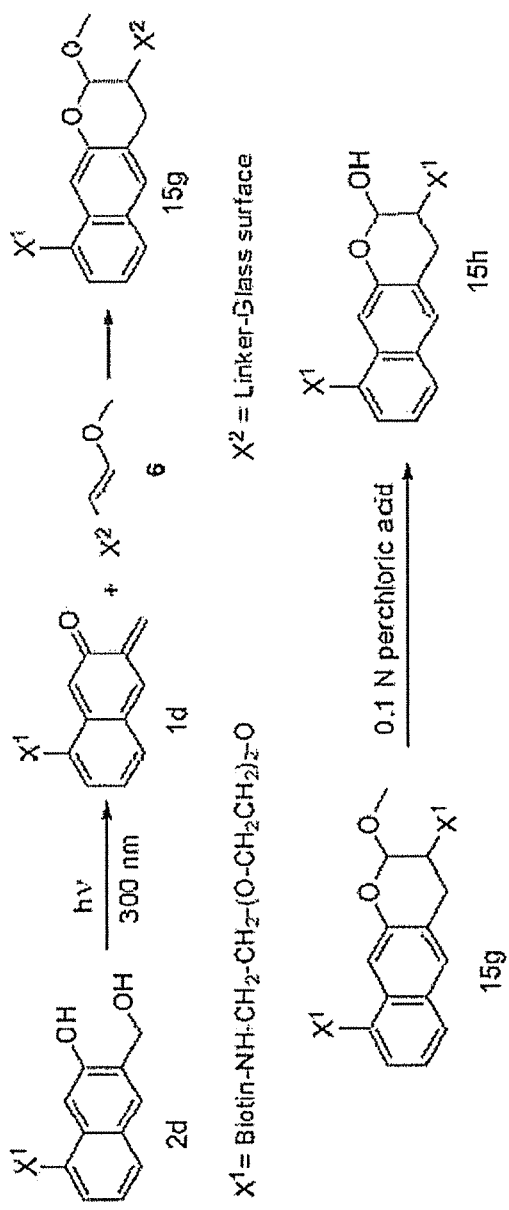
FIG. 25 is a schematic illustration of embodiments of the generation of an o-naphthoquinone methide by irradiation of a precursor compound, followed by a hetero-Diels-Alder reaction with a polarized olefin to form a hetero-Diels-Alder adduct; and hydrolysis of the exemplary hetero-Diels-Alder adduct under acidic conditions.
Figure 26:
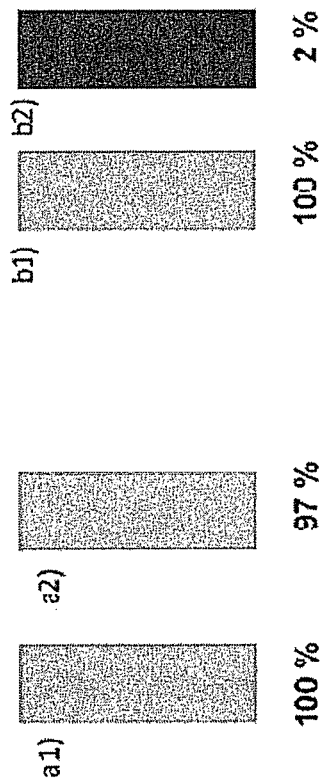
FIG. 26 illustrates embodiments showing FITC-Avidin stained biotinylated glass slides: (a1) unhydrolyzed glass slide functionalized through β-carbon atom of vinyl ether (a2) hydrolyzed glass slide functionalized through β-carbon atom of vinyl ether (b1) unhydrolyzed glass slide functionalized through oxygen atom of vinyl ether (b2) hydrolyzed glass slide functionalized through oxygen atom of vinyl ether.
Figure 27:
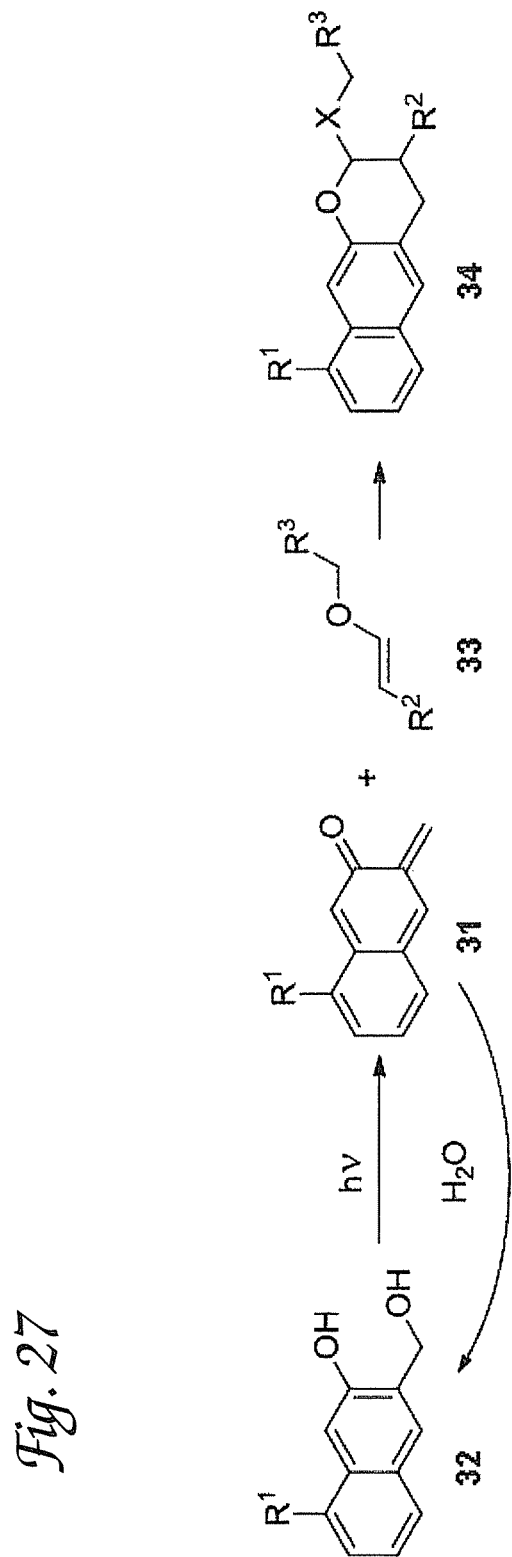
FIG. 27 is a schematic illustration of an embodiment of the generation of a 2-napthoquinone-3-methide, followed by a hetero-Diels-Alder cycloaddition with a vinyl ether to yield a photostable benzo[g]chroman.

For the application that requires permanent ligation, the vinyl ether should be immobilized on the glass surface through its β-carbon (FIG. 25). This can be achieved by treating the commercially available epoxide glass slides with 6-methoxyhex-5-en-1-ol in the presence of catalytic amount of anhydrous p-toluenesulfonic acid. In this case, the payload remained immobilized on the glass surface even after the dilute acid hydrolysis. For illustrative purpose, two vinyl ether glass slides prepared from 6-methoxyhex-5-en-1-ol and were flood irradiated in an aqueous solution of 2d to yield biotinylated glass slides. One of the biotinylated glass slides was then incubated in 0.1N perchloric acid solution overnight. The hydrolyzed glass slides and unhydrolyzed glass slides were then stained with labeled FITC-Avidin, washed with phosphate buffer solution overnight and scanned in Typhoon imager. As presented in FIG. 26, the acid hydrolysis did not detach any biotin molecules and therefore the resulting fluorescence intensities of both the slides (a1 and a2) are very much the same.

Control experiments with the vinyl ether slides (immobilized via oxygen atom) prepared from 2-(2-(vinyloxy)ethoxy)ethanamine were performed. As clearly seen from the FIG. 26 (slide b1 and b2), the acid hydrolysis almost quantitatively detach all the biotin molecules and therefore the difference in fluorescence intensities between the hydrolyzed glass slide and unhydrolyzed glass slide is close to 100%

In summary, we have demonstrated a very facile and highly efficient photo-click reaction for light triggered surface derivatization. The reaction dynamics of the click reaction is very rapid to allow patterned surface derivatization despite the fact that the photoactive click pair is taken in solution. From the technical point of view, this is more advantageous than functionalize the glass surface with the photoactive component. Functionalization of glass surface with photoactive component involves complication such as filter effect, secondary photochemistry on the surface. Besides, taking photoactive component in the solution provides more control in tuning its absorption at any given wavelength. Hence one can tailor the irradiation time at any particular wavelength and thereby number of molecules need to be attached on the surface. Due to robustness of the click reaction, light can be used as on/off switch for the immobilization of the molecules. The wide scope of this click reaction permits us to immobilize the vinyl ether functionality either through the oxygen atom or β-carbon of the vinyl ether. Immobilization through oxygen atom allows us to detach the payload when needed. Whereas permanent ligation can be achieved by immobilizing the vinyl ether through the β-carbon.

Example 3

General

All organic solvents were dried and freshly distilled before use. Flash chromatography was performed using 40-63 μm silica gel. Solutions for photochemical reaction were prepared using HPLC grade water and acetonitrile. Photoproducts were isolated from preparative scale reaction and were characterized by NMR, GC-MS and HRMS. The isolated pure photoproducts were then used as calibration standards for analytical scale reactions. Both preparative and analytical reactions were carried out using mini-Rayonet photochemical reactor equipped with 8 fluorescent UV lamps (4 W, 254, 300, or 350 nm). Reaction mixtures after photolysis were analyzed by HPLC and chemical yields were determined from the calibration plot constructed using known standards of the pure product. Rate measurements were conducted using LKS.60 kinetic spectrometer (Applied Photophysics) equipped with Brilliant B Nd: YAG laser (pulse width=4 ns) fitted with $2^{nd}$ and $4^{th}$ harmonic generators. Substrate concentration for kinetics experiments was kept at ca $1 \times 10^{-4}$ M for $2a$ and 0.04-0.05M for various olefins. Quantum efficiencies of photochemical reactions were measured by ferrioxalate actinometry. Buffer solutions for kinetic experiments were prepared using literature pKa values of the buffer acids and activity co-efficient recommended by Bates. (Bates, R. G. *Determination of pH Theory and Practice*; Wiley: New York, 1973; p 49). Quantum efficiencies of photochemical reactions were measured by ferrioxalate actinometry. (Murov et al., in: Handbook of Photochemistry, Marcel Dekker: New York, 1993, p. 299).

Materials:

Ethyl vinyl ether, olefins 8-11, 2-hydroxyethyl vinyl ether (3b), isopropenyl methyl ether (3c) and triethyleneglycol monomethyl ether were purchased from VWR and used as received. Synthesis of ethyl(3-hydroxy-2-naphthalenyl)methyl ether (Arumugam et al., *J. Am. Chem. Soc.* 2009, 131, 11892), 3-hydroxy-2-naphthalenemethanol (2a) (Arumugam et al., *J. Am. Chem. Soc.* 2009, 131, 11892), phenyl vinyl ether 12, (Grobelny et al., *J Organomet. Chem.* 2004, 689, 1580) enamine 13 (Klima et al., *J. Org. Chem.* 2007, 72, 6372) and 1-ethoxy-1-heptene (3d) (Ghribi et al. *Tetrahedron Lett.* 1984, 25, 3079) were previously reported in the literature.

Photolysis Procedure:

For the control experiments with olefins 3a and 8-12, solution of 2a (0.0029 mmol) and olefins 3a and 8-12 (0.29 mmol) in acetonitrile-water (1:1, 3 mL) was irradiated using mini-Rayonet photochemical reactor equipped with 16 fluorescent UV lamps)(RPR-3000A°) for 3 minutes (15% conversion) and 20 minutes (>99% conversion). The same photolysis procedures were followed for the preparative and analytical scale ligation of oNQM precursor 2a and 2d with vinyl ethers 3a-f and enamine 13. The representative procedure for the ligation of 2a with vinyl with 3b is described below.

Preparative Scale:

Solution of 2a (0.3 mmol) and vinyl ether 3a (43 μL, 0.45 mmol) in acetonitrile-water (1:1, 300 mL) was irradiated using mini-Rayonet photochemical reactor equipped with 16 fluorescent UV lamps)(RPR-2537A°) for 20 minutes. Photolysate was extracted with ethyl acetate, dried over sodium sulfate; and solvents were removed in vacuum.

DA Adduct 5a:

The adduct was separated by chromatography (20% EtOAc in hexane) to give 60 mg (87%) of 5a as colorless oil. $^1$H NMR (400 MHz, CDCl$_3$): δ 7.86 (d, 7.6 Hz, 1H), 7.78 (d, 7.6 Hz, 1H), 7.66 (d, 8.8 Hz, 1H), 7.48-7.52 (m, 1H), 7.34-7.38 (m, 1H), 7.08 (d, 8.8 Hz, 1H), 5.38 (t, 2.8 Hz, 1H), 3.90-3.94 (m, 1H), 3.67-3.71 (m, 1H), 3.08-3.15 (m, 2H), 2.20-2.26 (m, 1H), 2.11-0.15 (m, 1H), 1.20 (t, 7. Hz, 3H); $^{13}$C NMR (100 MHz): 15.38, 17.69, 26.63, 64.02, 97.06, 114.45, 119.31, 122.22, 123.54, 126.47, 127.93, 128.60, 129.15, 133.70, 149.85; EI-MS m/z: 229 (M$^+$+1), 228 (M+), 183, 182 (base peak), 181, 154, 153, 152, 128, 115, 102, 85, 72, 57, 55, 44; FW calc. (C$_{15}$H$_{16}$O$_2$): 228.1150, EI-HRMS. found 228.1142.

DA Adduct 5b:

The adduct was separated by chromatography (10% EtOAc in hexane) to give 64 mg (87%) of 5b as colorless oil. $^1$H NMR (400 MHz, CD$_3$CN): 7.70-7.78 (m, 2H), 7.62 (s, 1H), 7.37-7.41 (m, 1H), 7.31-7.34 (m, 1H), 7.24 (s, 1H), 5.42 (t, 2.8 Hz, 1H), 3.84-3.89 (m, 1H), 3.70-3.75 (m, 1H), 3.53-3.66 (m, 2H), 3.11 3.20 (m, 1H), 2.87-2.93 (m, 1H), 2.74 (t, J=6 Hz, 1H) 2.02-2.16 (m, 2H); $^{13}$C NMR (100 MHz, CD$_3$CN): 20.85, 26.65, 61.25, 70.11, 98.08, 111.66, 123.92, 125.37, 125.80, 126.44, 127.26, 127.87, 129.25, 133.76, 151.31; EI-MS m/z: 245 (10), 244 (80), 183 (40), 182 (70), 181 (100), 171 (10), 105 (10), 158 (70), 141 (75), 128 (80), 115 (20), 100 (20), 87 (75), 72 (25), 63 (15), 51 (10), 45 (30). FW calc. (C$_{15}$H$_{16}$O$_3$): 244.1099, EI-HRMS: 244.1102.

DA Adduct 5c:

The adduct was separated by chromatography (10% EtOAc in hexane) to give 58 mg (85%) of 5c as colorless oil. $^1$H NMR (400 MHz, CD$_3$CN): 7.69 (m, 2H), 7.55 (s, 1H), 7.69 (d, 8.3 Hz, 1H), 7.36 (m, 1H), 7.29 (m, 1H), 7.23 (s, 1H), 3.28 (m, 3H), 3.16-3.25 (m, 1H), 2.82-2.88 (m, 1H), 2.12-2.12 (m, 1H), 1.91-1.97 (m, 1H), 1.59 (t, 3H); $^{13}$C NMR (100 MHz, CD$_3$CN): 21.79, 21.75, 31.90, 48.66, 99.03, 111.68, 117.60, 123.87, 125.10, 125.71, 126.43, 127.23, 127.81, 129.26, 133.69, 151.82; EI-MS m/z: 229 (M$^+$+1), 229(5), 228 (27), 213 (6), 197 (25), 196 (48), 195 (40), 181 (100), 168 (10), 157 (250, 150 (20), 141 (15), 128 (55), 115 (15), 102 (10), 90 (12), 76 (12), 63 (12), 51 (12), 43 (50). FW calc. (C$_{15}$H$_{16}$O$_2$): 228.1150, EI-HRMS: 228.1146.

DA Adduct 5d:

The adduct was separated by chromatography (10% EtOAc in hexane) to give 80 mg (88%) of 5d as colorless oil. $^1$H NMR (400 MHz, CD$_3$CN): Diastereomer 1 (Major); 7.70-7.75 (m, 2H), 7.59 (s, 1H), 7.36-7.40 (m, 1H), 7.30-7.33 (m, 1H), 7.22 (s, 1H), 5.11 (d, J=3.2 Hz, 1H), 3.82-3.94 (m, 1H), 3.66-3.76 (m, 1H), 3.18-3.23 (m, 1H), 2.68-2.72 (m, 1H) 2.00-2.03 (m, 1H); 1.21-1.48 (m, 8H), 1.16 (t, J=6.8 Hz, 3H), 0.88 (t, J=6.8 Hz, 3H). Diastereomer 2 (Minor); 7.70-7.75 (m, 2H), 7.59 (s, 1H), 7.36-7.40 (m, 1H), 7.30-7.33 (m, 1H), 7.22 (s, 1H), 5.22 (d, J=3.2 Hz, 1H), 3.82-3.94 (m, 1H), 3.66-3.76 (m, 1H), 2.87-2.93 (m, 1H), 2.74-2.83 (m, 2H) 2.00-2.03 (m, 1H); 1.21-1.48 (m, 8H), 1.13 (t, J=6.8 Hz, 3H), 0.94 (t, J=6.8 Hz, 3H). $^{13}$C NMR (100 MHz, CD$_3$CN): Diastereomer 1 (Major); 13.62, 14.92, 22.59, 26.53, 26.65, 30.43, 32.96, 36.10, 63.97, 101.38, 111.39, 123.87, 124.68, 125.79, 126.49, 127.28, 128.36, 129.47, 133.88, 151.28 Diastereomer 2 (Minor); 13.62, 14.92, 22.59, 26.53, 26.65, 30.43, 32.96, 36.10, 63.97, 101.38, 111.39, 123.86, 125.53, 125.78, 126.44, 127.32, 127.90, 129.29, 133.87, 151.27 EI-MS m/z: Diastereomer 1 (Major); 299 (20), 298 (100), 254 (10), 239 (80), 209 (10), 195 (40), 181 (75), 169 (15), 157 (30), 141

(20), 128 (35), 115 (10), 95 (15), 57 (10), 41 (17). Diastereomer 2 (Minor); 299 (20), 298 (100), 240 (15), 239 (75), 195 (30), 181 (70), 157 (25), 141 (20), 128 (35), 95 (10), 55 (10), 43 (12). FW calc. ($C_{20}H_{26}O_2$): 298.1933, EI-HRMS:

DA Adduct 5f:

The adduct was separated by chromatography (10% EtOAc in hexane) to give 58 mg (85%) of 5f as colorless oil. $^1$H NMR (400 MHz, CDCl$_3$): 7.67-7.71 (m, 2H), 7.54 (s, 1H), 7.35-7.38 (m, 1H), 7.29-7.34 (m, 1H), 7.23 (s, 1H), 5.17 (d. J=4 Hz, 1H), 3.06 3.10 (m, 1H), 2.95 (d, J=4 Hz, 1H), 2.61-2.65 (m, 1H), 1.14 (s, 1H) 1.03 (s, 3H); $^{13}$C NMR (100 MHz, CDCl$_3$): 23.98, 24.39, 32.84, 35.57, 98.97, 111.62, 123.79, 123.85, 125.72, 126.61, 127.21, 128.35, 129.42, 133.74, 149.98; EI-MS m/z: 229 ($M^+$+1), 228(50), 195 (10), 183 (10), 158 (25), 157 (100), 128 (35), 115 (10), 71 (10), 43 (12). FW calc. ($C_{15}H_{16}O_2$): 228.1150, EI-HRMS: 228.1145

DA Adduct 5g:

The adduct was separated by chromatography (30% EtOAc in hexane) to give 136 mg (87%) of 5g as colorless oil. $^1$H NMR (400 MHz, CD$_3$CN): 7.72 (d, 8 Hz, 1H), 7.69 (d, 8 Hz, 1H), 7.59 (m, 1H), 7.37 (t, 6 Hz, 1H), 7.29 (t, 6 Hz, 1H), 7.21 (s, 1H), 7.17 (d, 7.2 Hz, 2H), 6.73 (d, 7.2 Hz, 2H), 5.44 (t, 2.4 Hz, 1H), 4.26-4.32 (m, 1H), 4.03-4.11 (m, 3H), 3.95-4.00 (m, 1H) 3.05-3.12 (m, 1H), 2.96-3.00 (m, 1H), 2.78-2.90 (m, 1H), 2.01-2.11 (m, 2H), 1.34 (s, 9H); $^{13}$C NMR (100 MHz, CD$_3$CN): 20.67, 26.49, 27.66, 36.57, 51.82, 55.25, 66.78, 67.56, 97.85, 111.67, EI-MS m/z: 521 (M+, 7), 466 (3), 447 (24), 421 (5), 404 (8), 362 (3), 333 (70), 227 (82), 183 (100), 155 (15), 153 (12), 128 (12), 107 (37), 91 (7), 78 (5). FW calc. ($C_{30}H_{35}NO_7$): 521.2414, EI-HRMS: 521.2408.

DA Adduct 5h:

The adduct was separated by chromatography (30% EtOAc in hexane) to give 100 mg (86%) of 5h as colorless oil. $^1$H NMR (400 MHz, CD$_3$CN): 7.56 (s, 1H), 7.52 (s, 1H), 7.32 (d, J=8 Hz, 1H), 7.20 (t, J=8 Hz, 1H), 6.8 (d, J=7.2 Hz, 1H), 5.38 (t, 2.8 Hz, 1H), 4.25 (m, 2H), 3.83-3.92 (m, 3H), 3.65-3.71 (m, 3H), 3.57-3.63 (m, 4H), 3.45-3.48 (m, 2H), 3.29 (s, 3H) 3.05-3.15 (m, 1H), 2.82-2.92 (m, 1H), 2.05 (m, 2H), 1.16 (t, 7.2 Hz, 3H); $^{13}$C NMR (100 MHz, CD$_3$CN): 14.84, 20.87, 26.76, 58.17, 63.74, 64, 69.68, 70.35, 70.49, 70.81, 71.91, 97.58, 104.82, 106.36, 119.78, 123.89, 125.63, 125.86, 127.71, 129.15, 130.21, 151.17, 153.71; EI-MS m/z: 391 (15), 390 (50), 345 (20), 344 (100), 314 (5), 285 (10), 244 (20), 198 (35), 197 (32), 169 (15), 147 (17), 115 (13), 103 (15). FW calc. ($C_{22}H_{30}O_6$): 390.2042, EI-HRMS: 390.2048.

DA Adduct 5i:

The adduct was separated by chromatography (30% EtOAc in hexane) to give 150 mg (89%) of 5i as colorless oil. $^1$H NMR (400 MHz, CDCl$_3$): Diastereomer 1 (major); 7.67-7.70 (m, 2H), 7.53 (s, 1H), 7.35 (t, J=7.6 Hz, 1H), 7.29 (t, J=7.6 Hz, 1H), 7.25 (d, J=4.8 Hz, 1H), 6.96 (d, J=8 Hz, 2H), 6.73 (d, J=8 Hz, 2H), 5.00-5.02 (m, 1H), 4.97 (d, J=2.4 Hz, 1H), 4.51-4.56 (m, 1H), 3.71 (s, 3H), 3.62-3.65 (t, J=6.4 Hz, 2H), 3.52 (s, 3H), 3.24-3.29 (m, 1H), 2.93-3.05 (m, 2H), 2.64-2.69 (m, 1H), 2.03-2.16 (m, 1H), 1.42 (s, 9H), 1.25-1.63 (m, 6H). Diastereomer 2 (Minor); 7.67-7.70 (m, 2H), 7.52 (s, 1H), 7.35 (t, J=7.6 Hz, 1H), 7.29 (t, J=7.6 Hz, 1H), 7.25 (d, J=4.8 Hz, 1H), 6.96 (d, J=8 Hz, 2H), 6.73 (d, J=8 Hz, 2H), 5.05 (d, J=2.4 Hz, 1H), 5.00-5.02 (m, 1H), 4.51-4.56 (m, 1H), 3.71 (s, 3H), 3.68-3.72, (t, J=6.4 Hz, 2H), 3.48 (s, 3H), 2.93-3.05 (m, 2H), 2.86-2.94 (m, 1H), 2.68-2.72 (m, 1H) 2.86-2.88 (m, 1H); 2.64-2.69 (m, 1H), 2.03-2.16 (m, 1H), 1.42 (s, 9H), 1.25-1.63 (m, 6H). $^{13}$C NMR (100 MHz, CDCl$_3$): Diastereomer 1 (major); 172.81, 155.47, 155.29, 150.52, 133.7, 130.61, 129.42, 128.47, 127.90, 127.20, 126.59, 125.70, 123.87, 123.77, 115.71, 111.85, 102.11, 80.34, 62.98, 55.95, 54.83, 52.46, 37.78, 35.89, 32.92, 30.35, 28.53, 26.59, 23.46. Diastereomer 2 (Minor); 172.81, 155.47, 155.29, 150.58, 133.7, 130.61, 129.26, 128.47, 127.83, 127.29, 126.54, 125.67, 124.74, 123.84, 115.71, 111.91, 100.83, 80.34, 63.04, 56.09, 54.83, 52.46, 37.78, 36.59, 33.03, 31.35, 28.53, 27.40, 23.29. FW calc. ($C_{33}H_{41}NO_7$): 563.2883, ESI-HRMS: 563.2898.

Analytical Scale:

Solution of 2a (0.003 mmol) and vinyl ether 3a (43 μL, 0.0045 mmol) in acetonitrile-water (1:1, 3 mL) was irradiated using mini-Rayonet photochemical reactor equipped with 16 fluorescent UV lamps)(RPR-2537A°) for 20 minutes. An aliquot sample was drawn from the photolysate and analyzed in HPLC. Chemical yields were determined from the calibration plot constructed from the standard known isolated from preparative scale reactions.

Fluorescent Measurements:

Fluorescent spectra of 2a were recorded at $\lambda_{ex}$=305 nm in doubly deionized water with the substrate concentration ca. $1 \times 10^{-5}$ M using Varian steady state fluorimeter. The excitation source slits and the detector slits were set to 2 nm and 5 nm respectively. The fluorescence quantum yield were determined using 2-naphthol as the standard reference. (Wang et al., J. Org. Chem. 2002, 67, pp 2429; Berlman, I. B. Handbook of Fluorescence Spectra of Aromatic Molecules. Academic Press, New York, 1971, 473 p). The fluorescent life time of the excited state of 2a were measured LKS.60 Applied Photophysics spectrometer using the fourth harmonic (266 nm) from the Brilliant B Nd:YAG laser as an excitation source with a pulse width of 7 ns.

Kinetic Experiments:

All kinetic rate measurements were made using LKS.60 Applied Photophysics spectrometer. Flash photolysis were initiated using the fourth harmonic (266 nm) from the Brilliant B Nd:YAG laser as an excitation source with a pulse width of 7 ns. Spectral changes were monitored at 310 nm using 100 W xenon arc lamp, monochromotor and photomultiplier tube. Data were recorded on a digital oscilloscope and transferred to the computer for subsequent analysis. For a typical experiment samples of oNQM ($1 \times 10^{-4}$ M) were prepared in a static quartz cell and purged with nitrogen for a period of 15 minutes prior to flash photolysis. The temperature of the sample solution during flash photolysis was maintained at 25±0.05° C. First order rate constant were obtained by least-square fitting of the observed exponential function for the QM formation and decay. Second order rate constant with NQM trapping reagents were determine from the plot of the concentration of the trapping reagents Vs the observed first order rate constants.

Figure 12:
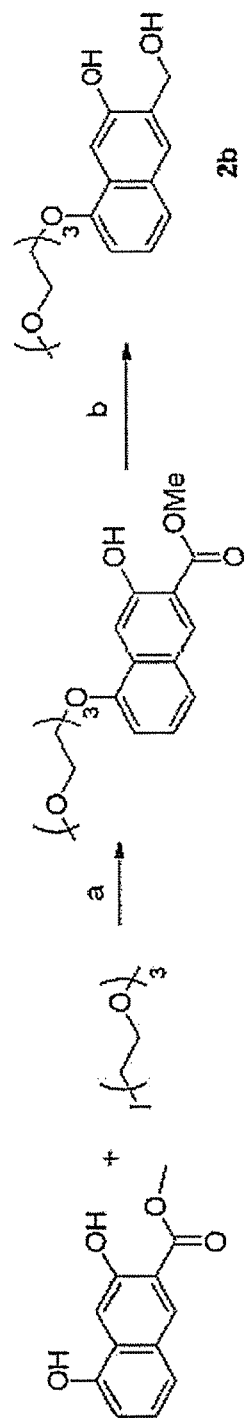
FIG. 12 is a schematic illustration for an exemplary method for preparing an embodiment of a precursor compound. Reagents and conditions: (a) $K_2CO_3$, acetone, reflux, 70%; (b) $LiAlH_4$, tetrahydrofuran (THF), 92%.

Synthesis of triethylene glycol-modified precursors 2b is outlined in FIG. 12. Preparation of triethylene glycol mono methyl ether and it's coupling to 3-hydroxy-2-naphthalenemethanol were achieved using literature procedures. All products were characterized by NMR, GC-MS and HRMS.

Synthesis of Tyrosine Appended Vinyl Ether 3e.

Figure 13:
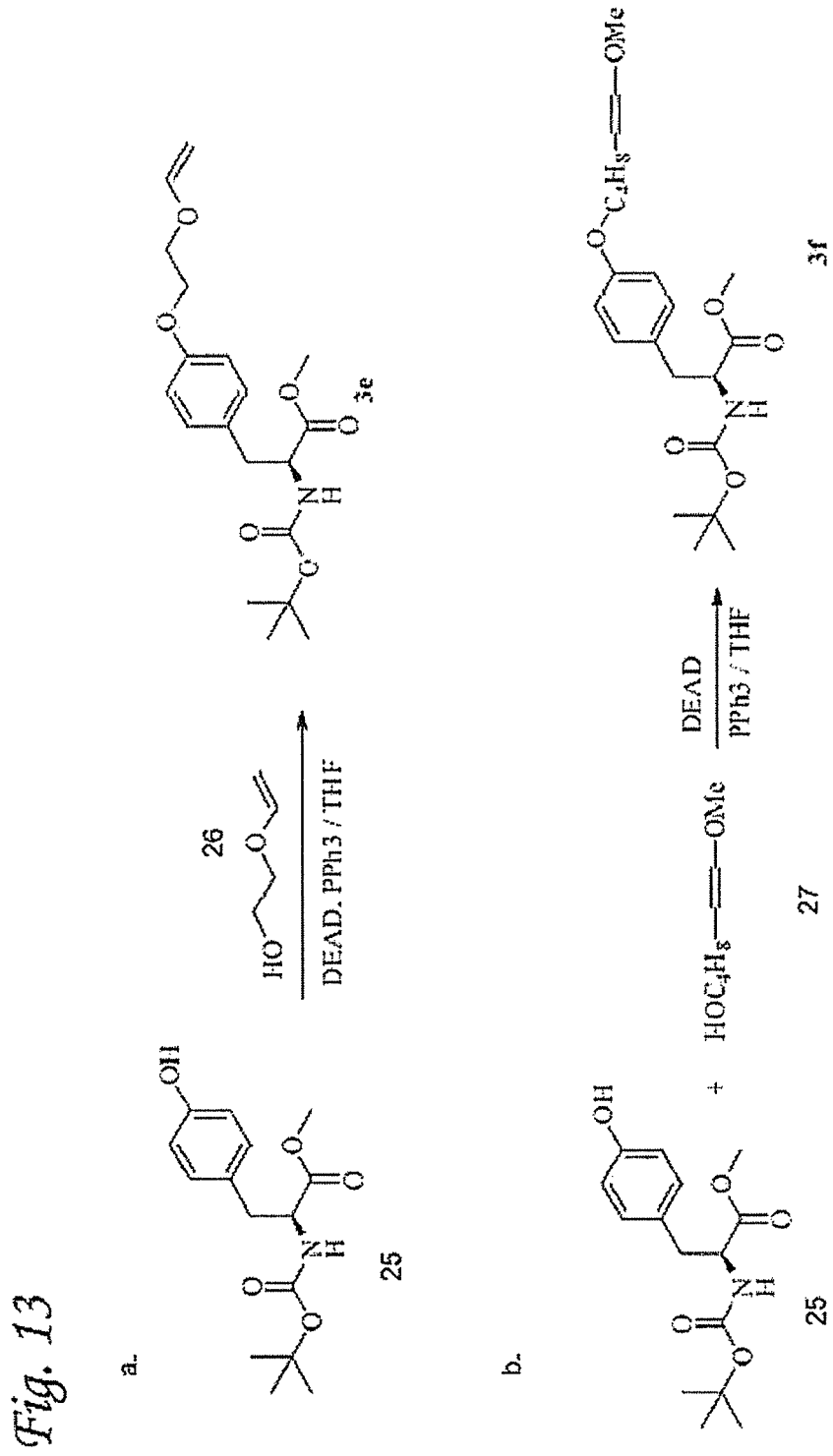
FIGS. 13(a) and (b) are schematic illustrations for an exemplary method for preparing embodiment of polarized olefins.

The synthesis is illustrated schematically in FIG. 13a. About 1 g (3.4 mmol) of 25 was taken in dry THF and to it 1.2 equivalent of PPh$_3$ (1.1 g, 4.1 mmol) were added at 0° C. To the reaction mixture, 1.2 equivalents of DEAD (710 mg, 4.1 mmol) was added and stirred for another 4 hours at room temperature. After the reaction is complete, it was quenched with water and the product was extracted in ethyl ether. The ether solution was washed with brine, dried over anhydrous magnesium sulfate and the solvent was removed under reduced pressure. The product was further purified column chromatography eluting with 5% ethyl acetate in chloroform to yield 1.1 g of 3e (87%). $^1$H NMR (400 MHz, CDCl$_3$): 7.02 (d, J=4.8 Hz, 2H), 6.84 (d, J=4.8 Hz, 2H), 6.50-6.55 (m, 1H), 4.98-4.50 (m, 1H), 4.50-4.55 (m, 1H), 4.21-4.25 (m, 1H), 4.17-4.18 (m, 2H), 4.00-4.10 (m, 3H), 3.69 (s, 3H), 2.96-3.07 (m, 2H), 1.41 (s, 9H). $^{13}$C NMR (100 MHz, CDCl$_3$): 28.49, 37.71, 52.29, 54.78, 66.65, 80.04, 87.26, 114.98, 128.72, 130.46, 151.83, 155.29, 157.93, 172.56. EI-MS m/z: 365 (0.1), 309 (1), 292 (2), 248 (45), 232 (1), 206 (6), 177 (100), 162 (1), 151 (1), 135 (6), 117 (3), 107 (90), 88 (10), 73 (40), 71 (35). FW calc. (C$_{19}$H$_{27}$NO$_6$): 365.1838, EI-FIRMS: 365.1827.

Synthesis of Tyrosine Appended Vinyl Ether 3e.

The synthesis is illustrated schematically in FIG. 13b. About 750 mg (5.8 mmol) of 27 was taken in dry THF and to it 1.1 equivalent of 25 (1.88 g, 6.4 mmol), 1.2 equivalent of PPh$_3$ (1.81 g, 6.9 mmol) was added at 0° C. To the reaction mixture, 1.2 equivalents of DEAD (1.2 mg, 1.1 mL, 6.9 mmol) was added and stirred for another 4 hours at room temperature. After the reaction is complete, it was quenched with water and the product was extracted in ethyl ether. The ether solution was washed with brine, dried over anhydrous magnesium sulfate and the solvent was removed under reduced pressure. The product was further purified by column chromatography using 5% ether in dichloromethane to yield 1.65 g of the vinyl ether 3f (70%). $^1$H NMR (400 MHz, CDCl$_3$) trans isomer: 7.02 (d, J=8.8 Hz, 2H), 6.82 (d, J=8.8 Hz, 2H), 6.32 (d, J=12.8 Hz, 1H), 4.96 (d, J=8 Hz, 1H), 4.71-4.77 (m, 1H), 4.52-4.57 (m, 1H), 3.93 (t, J=6 Hz, 2H), 3.72 (s, 3H), 3.51 (s, 3H), 2.97-3.08 (m, 2H), 1.98-2.03 (m, 2H), 2.75-1.82 (m, 2H), 1.48-1.55 (m, 2H) 1.43 (s, 9H); $^{13}$C NMR (100 MHz, CDCl$_3$) trans isomer: 27.37, 27.63, 28.53, 28.82, 37.68, 52.39, 54.76, 56.13, 68.00, 80.10, 102.82, 114.77, 127.95, 130.47, 147.54, 155.32, 158.41, 172.68. EI-MS m/z: 407 FW calc. (C$_{22}$H$_{33}$NO$_6$): 407.2308, EI-HRMS: 407.2298.

Synthesis of biotin—3-hydroxy-2-naphthalenemethanol conjugate 2d is outlined in FIG. 14.

Synthesis of 18:

About 0.75 g (3.4 mmol) of 17 was taken in acetone (10 mL) and to it 1.2 equivalent of potassium carbonate (1.13 g, 8.17 mmol) was added. To the reaction mixture, 1.4 g (3.75 mmol) of 16 was added drop wise and refluxed for 4 hours. After the reaction is complete, the excess solvent was removed under reduced pressure and the residue was taken in ethyl ether. The ether solution was washed with brine, dried over anhydrous magnesium sulfate and the solvent was removed under reduced pressure. The product was further purified by column chromatography using 50% ethyl acetate in hexane to yield 1.03 g of 18 (65%). $^1$H NMR (400 MHz, CDCl$_3$): 10.35 (s, 1H), 8.38 (s, 1H), 7.69 (s, 1H), 7.32 (d, 8 Hz, 1H), 7.15 (t, 7.6 Hz, 1H), 6.77 (d, 8 Hz 1H), 4.21-4.23 (m, 2H), 3.93-3.97 (m, 2H), 3.70-3.73 (m, 4H), 3.65-3.67 (m, 2H), 3.51-3.53 (m, 2H), 0.83 (s, 9H), 0.00 (s, 6H). $^{13}$C NMR (100 MHz, CDCl$_3$): −5.21, 18.41, 25.97, 52.58, 62.77, 68.06, 69.81, 70.89, 71.16, 72.78, 107.09, 107.31, 121.46, 123.80, 128.024, 130.61, 131.85, 153.33, 156.19, 170.36. EI-MS m/z: 464 (M+, 1), 449 (1), 417 (3), 409 (6), 407 (20), 376 (27), 375 (100), 331 (4), 287 (5), 259 (8), 257 (10), 243 (12), 213 (25), 185 (14), 169 (3), 157 (5), 129 (6), 101 (7), 88 (4), 73 (31). FW calc. (C$_{24}$H$_{36}$O$_7$Si): 464.2230, EI-HRMS: 464.2240.

Synthesis of 2e:

About 1.2 equivalent of LiAlH$_4$ (0.100 g, 2.58 mmol) was taken in dry THF and to it 1 g (2.15 mmol) of 18 was added at 0° C. The reaction mixture is warmed to room temperature and stirred for another 4 hours. After the reaction is complete, it was quenched with 5% HCl and the product was extracted in ethyl ether. The ether solution was washed with brine, dried over anhydrous MgSO$_4$ and the solvent was removed under reduced pressure. The crude mixture was taken in 10 mL of acetonitrile and stirred with 2.5 equivalents of aqueous HF. After complete deprotection of TBDMS group, the reaction mixture was taken in 100 mL of ethyl acetate and the organic extract was washed with saturated NaHCO$_3$, washed with brine, dried over anhydrous magnesium sulfate and the solvent was removed under reduced pressure. The product was further purified by column chromatography using 100% ethyl acetate to yield 0.59 g of 2e (85% yield). $^1$H NMR (400 MHz, DMSO-d8): 9.80 (s, 1H), 7.73 (s, 1H), 7.41 (s, 1H), 7.32 (d, 8 Hz, 1H), 7.12 (t, 7.6 Hz, 1H), 6.80 (d, 8 Hz, 1H), 5.13 (t, J=5.6 Hz, 1H), 4.59-4.60 (m, 3H), 4.19-4.21 (m, 2H), 3.84-3.86 (m, 2H), 3.63-3.66 (m, 4H), 3.54-3.57 (m, 2H), 3.40-3.47 (m, 4H). $^{13}$C NMR (100 MHz, DMSO-d8): 58.60, 60.32, 67.55, 69.23, 69.95, 70.22, 72.46, 102.79, 104.77, 119.89, 122.60, 125.17, 125.24, 128.72, 132.05, 152.75. EI-MS m/z: 322 (M+, 90), 304 (25), 259 (5), 242 (5), 216 (12), 198 (25), 172 (7), 144 (50), 115 (70), 89 (100), 85 (60), 71 (5). FW calc. (C$_{17}$H$_{22}$O$_6$): 322.1416, EI-FIRMS: 322.1413.

Synthesis of 19:

About 0.5 g (1.55 mmol) of 2e was taken in acetone (15 mL) and to it 3 equivalents of 2,2-dimethoxypropane (0.480 g, 4.65 mmol) and catalytic amount of TsOH were added. The reaction mixture was stirred at room temperature overnight. The excess solvent was removed under reduced pressure and the residue was taken in dichloromethane. The dichloromethane solution was washed with brine, dried over anhydrous magnesium sulfate and the solvent was removed under reduced pressure. The product was further purified by column chromatography using 55% ethyl acetate in hexane to yield 0.465 g of 19 (90%). $^1$H NMR (400 MHz, CDCl$_3$): 7.65 (s, 1H), 7.41 (s, 1H), 7.29 (d, 8 Hz, 1H), 7.18 (t, 7.6 Hz, 1H), 6.71 (d, 8 Hz 1H), 5.05 (s, 2H), 4.24-4.27 (m, 2H), 3.95-3.97 (m, 2H), 3.78-3.80 (m, 2H), 3.70-3.74 (m, 4H), 3.61-3.63 (m, 2H), 1.59 (s, 6H). $^{13}$C NMR (100 MHz, CDCl$_3$): 25.16, 61.38, 62.03, 68,04470.51, 70.70, 71.24, 72.75, 100.03, 104.91, 107.27, 120.14, 121.74, 123.29, 123.88, 126.44, 129.72, 149.65, 153.83. DIP-EI-MS m/z: 362 (M+, 30), 304 (100), 273 (7), 259 (5), 216 (20), 198 (30), 174 (35), 172 (40), 144 (25), 115 (45), 85 (40), 87 (52), 73 (12). FW calc. (C$_{20}$H$_{26}$O$_6$): 362.1729, EI-HRMS: 362.1729.

Synthesis of 20:

About 0.362 g (1 mmol) of 19 was taken in dichloromethane (7 mL) and to it 2 equivalents of triethylamine (0.2 g, 28 μL, 2 mmol) and 1.2 equivalents of p-tosyl chloride (228 mg, 1.2 mmol) were added. The reaction mixture was stirred at room temperature overnight. The excess solvent was removed under reduced pressure and the residue was taken in dichloromethane. The dichloromethane solution was washed with brine, dried over anhydrous MgSO$_4$ and the solvent was removed under reduced pressure. The product was further purified by column chromatography using 75% ethyl acetate in hexane to yield 0.423 mg of 20 (82%). $^1$H NMR (400 MHz, CD$_3$CN): 7.77 (d, 8 Hz, 2H), 7.53 (s, 1H), 7.49 (s, 1H), 7.34-7.39 (m, 3H), 7.24 (t, 7.6 Hz, 1H), 6.82 (d, 8 Hz, 1H), 5.05 (s, 2H), 4.21-4.24 (m, 2H), 4.11-4.12 (m, 2H), 3.88-3.90 (m, 2H), 3.63-3.64 (m, 4H), 3.53-3.55 (m, 2H), 2.39 (s, 3H), 1.55 (s, 6H). $^{13}$C NMR (100 MHz, CD$_3$CN): 20.95, 24.64, 61.07, 68.35, 68.62, 69.76, 70.30, 70.59, 70.75, 100.24, 105.37, 106.45, 120.13, 122.39, 123.85, 124.21, 126.32, 128.07, 129.87, 130.31, 133.33, 145.63, 149.99, 153.82. EI-MS m/z: 515 (M+, 3), 458 (15), 424 (12), 422 (12), 368 (40), 366 (42), 323 (7), 287 (10), 259 (50), 242 (32), 199 (50), 198 (40), 171 (25), 144 (15), 115 (60), 109 (90), 107 (100), 91 (25). FW calc. (C$_{27}$H$_{32}$O$_8$S): 516.1818, EI-HRMS: 516.1812.

Synthesis of 21:

About 0.4 g (0.78 mmol) of 20 was taken in N,N-dimethylformamide (5 mL) and to it 2 equivalents of sodium azide (0.06 g, 0.94 mmol) was added. The reaction mixture was stirred at 60° C. overnight. The excess solvent was removed under reduced pressure and the residue was taken in ether. The ether solution was washed with brine, dried over anhydrous magnesium sulfate and the solvent was removed under reduced pressure. The product was further purified by column chromatography using 40% ethyl acetate in hexane to yield 0.240 mg of 21 (80%). $^1$H NMR (400 MHz, CD$_3$CN): 7.58 (m, 2H), 7.35 (d, 8 Hz, 1H), 7.24 (t, 7.6 Hz, 1H), 6.83 (d, 8 Hz 1H), 5.06 (s, 2H), 4.24-4.26 (m, 2H), 3.93-3.95 (m, 2H), 3.73-3.76 (m, 2H), 3.66-3.67 (m, 4H), 3.66-3.69 (m, 2H), 1.57 (s, 6H). $^{13}$C NMR (100 MHz, CD$_3$CN): 24.64, 50.93, 61.09, 68.36, 69.78, 69.94, 70.58, 70.90, 100.24, 105.36, 106.47, 120.13, 122.41, 123.86, 124.22128.01, 129.88, 150.02, 153.85. EI-MS m/z: 387 (M$^+$, 30), 359 (40), 318 (7), 301 (100), 260 (15), 212 (50), 199 (50), 185 (35), 170 (35), 144 (38), 129 (36), 115 (77), 73 (92). FW calc. (C$_{20}$H$_{25}$N$_3$O$_5$): 387.1794, EI-HRMS: 387.1787.

Synthesis of 22:

About 2 equivalent of LiAlH$_4$ (0.038 g, 1 mmol) was taken in dry ethyl ether and to it 0.2 g (0.52 mmol) of 21 was added at 0° C. The reaction mixture is warmed to room temperature and stirred for another 4 hours. After the reaction is complete, it was quenched with 5% HCl and the product was extracted in ethyl ether. The ether solution was washed with brine, dried over anhydrous magnesium sulfate and the solvent was removed under reduced pressure to yield 152 mg (81%) of the amine 22 and was taken to next step without any purification. $^1$H NMR (400 MHz, CD$_3$CN): 7.51 (s, 1H), 7.49 (m, 2H), 7.33 (d, 8 Hz, 1H), 7.23 (t, 7.6 Hz, 1H), 6.80 (d, 8 Hz 1H), 5.03 (s, 2H), 4.20-4.22 (m, 2H), 3.88-3.90 (m, 2H), 3.68-3.70 (m, 2H), 3.59-3.60 (m, 2H), 3.41-3.43 (m, 2H), 2.73 (br s, 2H), 2.10 (br s, 2H), 1.55 (s, 6H). $^{13}$C NMR (100 MHz, CD$_3$CN): 26.08, 41.61, 62.49, 69.76, 71.75, 72.21, 72.27, 101.66, 106.77, 107.90, 121.57, 123.79, 125.27, 125.64, 127.74, 131.28, 151.41, 156.24. EI-MS m/z: 361 (M$^+$, 100), 343 (7), 326 (5), 303 (75), 286 (18), 260 (7), 244 (12), 228 (15), 201 (37), 186 (60), 172 (37), 144 (26), 128 (26), 115 (70), 103 (6), 88 (12), 70 (35). FW calc. (C$_{20}$H$_{27}$NO$_5$): 361.1889, EI-HRMS: 361.1889.

Synthesis of 24:

About 56 mg of d-biotin (0.23 mmol) was taken in 5 mL dry N,N-dimethyl formamide and to it added 1.2 equivalents of EDC.HCl and catalytic amount of DMAP were added. To this solution, 90 mg (0.25 mmol) of the amine 22 in 2 mL, of N,N-dimethyl formamide was added drop wise and the mixture was stirred for 12 hours at room temperature. After the reaction is complete, N,N-dimethyl formamide was removed in vacuum. The residue is taken dichloromethane, washed with NaHCO$_3$ solution, brine dried over anhydrous magnesium sulfate and the solvent was removed under reduced pressure. The product was further purified by column chromatography using 10% methanol in dichloromethane to yield 0.12 mg of 24 (83%). $^1$H NMR (400 MHz, CD$_3$CN): 7.62 (s, 1H), 7.42 (s, 1H), 7.28 (t, 8 Hz, 1H), 7.19 (t, 8 Hz, 1H), 6.92 (t, 8 Hz, 1H), 6.77 (s, 1H), 6.72 (d, 8 Hz 1H), 5.87 (s, 1H), 5.04 (s, 2H), 4.36-4.39 (m, 1H), 4.24-4.25 (m, 2H), 4.08-4.11 (m, 1H), 3.93-3.94 (m, 2H), 3.65-3.67 (m, 2H), 3.56-3.59 (m, 2H), 3.41-3.43 (m, 2H), 2.91-2.93 (m, 1H), 2.74-2.78 (m, 1H), 2.63-2.66 (m, 2H), 2.15 (t, 7.8 Hz, 2H), 1.55 (s, 6H), 1.53-1.63 (m, 4H), 1.27-1.30 (m, 2H). $^{13}$C NMR (100 MHz, CD$_3$CN): 25.21, 25.75, 28.26, 36.1839.40, 40.70, 60.39, 61.38, 61.91, 68.11, 70.03, 70.24, 70.43, 70.93, 100.10, 104.98, 107.14, 120.27, 121.85, 123.42, 123.97, 126.36, 129.72, 149.72, 153.76, 164.35, 173.53. FW calc. (C$_{30}$H$_{41}$N$_3$O$_7$S): 587.2665, EI-HRMS: 587.2676.

Synthesis of 2d:

About 100 mg (0.17 mmol) of 24 was taken 5 mL of methanol and to it 60 mg of Amberlyst was added and stirred for 2 hours at room temperature. The amberlyst resin was filtered through cotton plug and the methanol solution was passed through short silica gel to yield 93 mg analytically pure biotinylated 3-hydroxymethylnaphthalene-2-ol chromophore (2d) in 95% yield. $^1$H NMR (400 MHz, d4-Methanol): 7.90 (t, 8 Hz, 1H), 7.73 (s, 1H), 7.52 (s, 1H), 7.32 (d, 8 Hz, 1H), 7.14 (t, 8 Hz, 1H), 6.75 (d, 8 Hz 1H), 4.87 (s, 2H), 4.30-4.33 (m, 1H), 4.20-4.22 (m, 2H), 4.09-4.07 (m, 1H), 3.92-3.93 (m, 1H), 3.73-3.74 (m, 2H), 3.62-3.64 (m, 2H), 3.52-3.55 (m, 2H), 3.32-3.36 (m, 2H), 2.96-2.99 (m, 1H), 2.74-2.79 (m, 1H), 2.60-2.63 (m, 2H), 2.12 (t, 7.8 Hz, 2H), 1.42-1.62 (m, 4H), 1.23-1.32 (m, 2H). $^{13}$C NMR (100 MHz, d4-Methanol): 25.60, 28.23, 28.49, 35.58, 39.23, 39.88, 55.72, 60.21, 62.10, 67.89, 69.48, 69.89, 70.14, 70.82, 96.13, 103.55, 105.06, 120.30, 122.84, 126.27, 126.43, 129.68, 130.74, 153.23, 153.40, 164.82, 174.97. FW calc. (C$_{27}$H$_{37}$N$_3$O$_7$S): 547.2352, EI-HRMS: 547.2349.

Example 4

The utility of photochemically induced hetero-Diels-Alder reaction for light-directed surface derivatization and patterning was demonstrated. Glass slides functionalized with vinyl ether moieties were covered with aqueous solutions of substrates conjugated to 3-(hydroxymethyl)-2-naphthol (NQMP). Subsequent irradiation via shadow mask resulted in an efficient conversion of the latter functionality into reactive 2-napthoquinone-3-methide (oNQM) in the exposed areas. oNQM underwent vary facile ($k_{D-A}$~4×10$^4$ M$^{-1}$s$^{-1}$) hetero Diels-Alder addition to immobilized vinyl ether molecules resulting in a photochemically stable covalent link between a substrate and a surface. Unreacted oNQM groups were rapidly hydrated to regenerate NQMP. The click chemistry based on the addition of photochemically generated oNQM to vinyl ether worked well in aqueous solution, proceeded at high rate under ambient conditions, and did not require catalyst or additional reagents. This photo-click strategy represents an unusual paradigm in photo-patterning: the surface itself is photochemically inert, while photoreactive component is present in the solution. The short lifetime (τ~7 milliseconds in H$_2$O) of the active form of a photo-click reagent in aqueous solution prevents its migration from the site of irradiation, thus allowing for the spatial control of surface derivatization. Both o-napthoquinone methide precursors and vinyl ethers are stable in dark and the reaction is orthogonal to other derivatization techniques, such as acetylene-azide click reaction.

To illustrate the utility of photo chemically-induced hetero-Diels-Alder cycloaddition for light-directed surface derivatization, we have patterned fluorescently labeled Avidin onto vinyl ether-derivatized glass slides.

Preparation of Materials.

Figure 28:
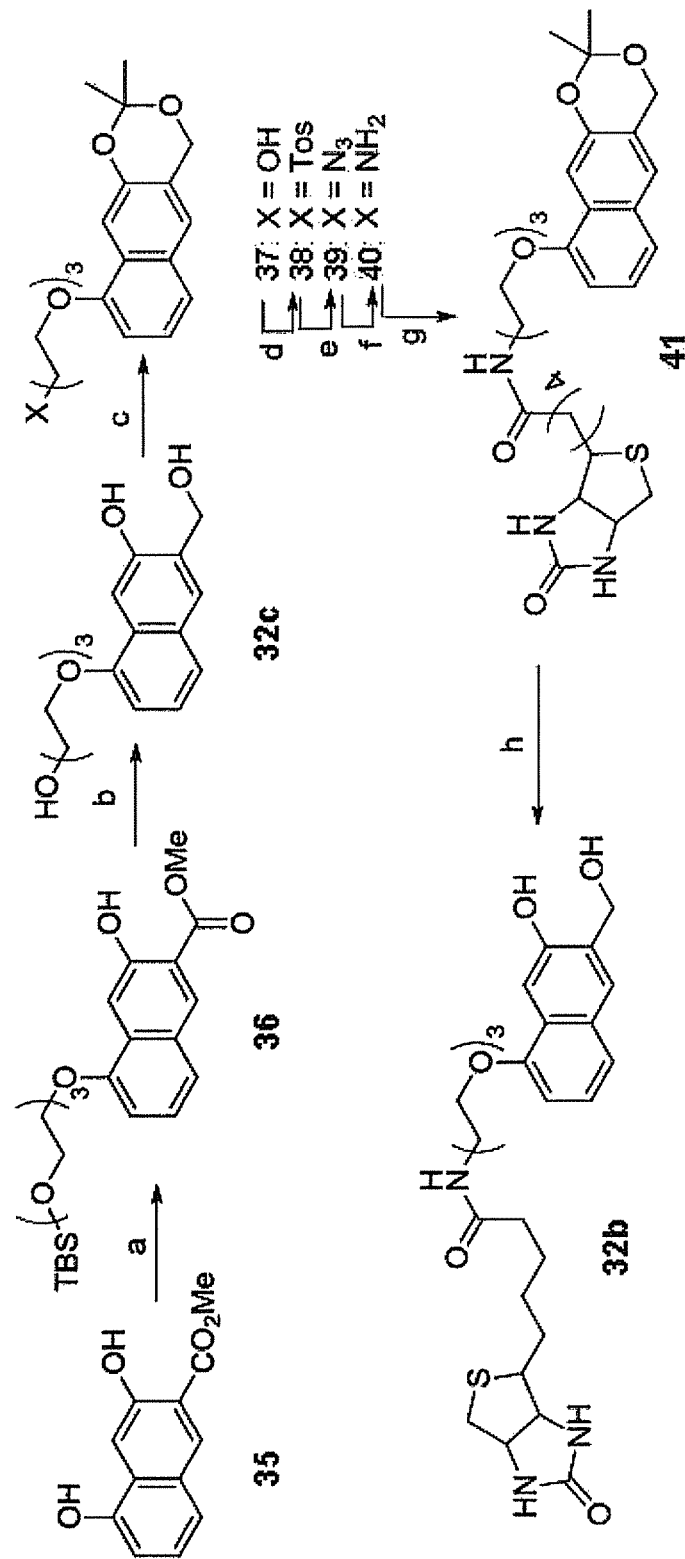
FIG. 28 is a schematic illustration of the synthesis of 6-(hydroxymethyl)naphthalene-1,7-diol-PEG3-biotin conjugate. Reagents and conditions: (a) TBDMS $(OCH_2CH_2)_3I$, $K_2CO_3$, acetone, reflux, 65%; (b) i) $LiAlH_4$, THF; $HF/CH_3CN$ aq., 85% over 2 steps; (c) TsOH, 2,2-dimethoxypropane, acetone, 90%; (d) TsCl, pyridine, DCM, 82%; (e) $NaN_3$, DMF, 60° C., 80%; (f) $LiAlH_4$, $Et_2O$, 85%; (g) d-biotin, EDC, DMAP, DMF, 83%; (h) Amberlyst-15, methanol, room temperature, 95%.

Synthesis of 6-(hydroxymethyl)naphthalene-1,7-diol-tri(ethylene glycol)-biotin conjugate (NQMP-TEG-biotin, 32b) is outlined in FIG. 28. Methyl 3,5-dihydroxy-2-naphthoate (35) was prepared according to previously reported literature (Kim and Hangauer, 2000 *Bull. Korean Chem. Soc.* 21:757) and was etherified to iodo-TEG-TBDMS, followed by lithium aluminum hydride reduction and deprotection to give NQMP-TEG (32c). The glycol moiety was then protected as acetone ketal and the TEG terminal hydroxy group was tosylated. Nucleophilic substitution of tosyl ester with azide ion produced 39, which was further reduced to an amino derivative 40. EDC-promoted coupling of the latter with d-biotin, followed by ketal hydrolysis produced target NQMP-TEG-biotin (32b, FIG. 29).

The synthetic intermediates shown in the FIG. 28 can serve as entry points for the conjugation of NQMP with various "payload" substrates. Thus, molecules inert to hydride reduction can be coupled directly 35. NQMP-TEG (32c) or its protected analog 37 possess primary alcohol moiety, which is suitable for Mitsunobu coupling or esterification; acetylene click reaction can be employed to modify azide derivative 39; molecules containing carboxylic acid or NHS-ester groups can be readily coupled with protected NQMP-TEG-NH$_2$ (40).

Light-Directed Surface Derivatization.

Vinyl ether derivatization of commercial epoxide-functionalized glass slides was achieved by treating the slides with 2-hydroxyethyl vinyl ether or 6-methoxyhex-5-en-1-ol in the presence of catalytic amount of anhydrous p-toluenesulfonic acid. Alternatively, incubation of epoxy slides in 2-(2-(vinyloxy)ethoxy)ethanamine dichloromethane solution yields vinyl ether functionalized glass slides without the need for a catalyst.

Figure 29:
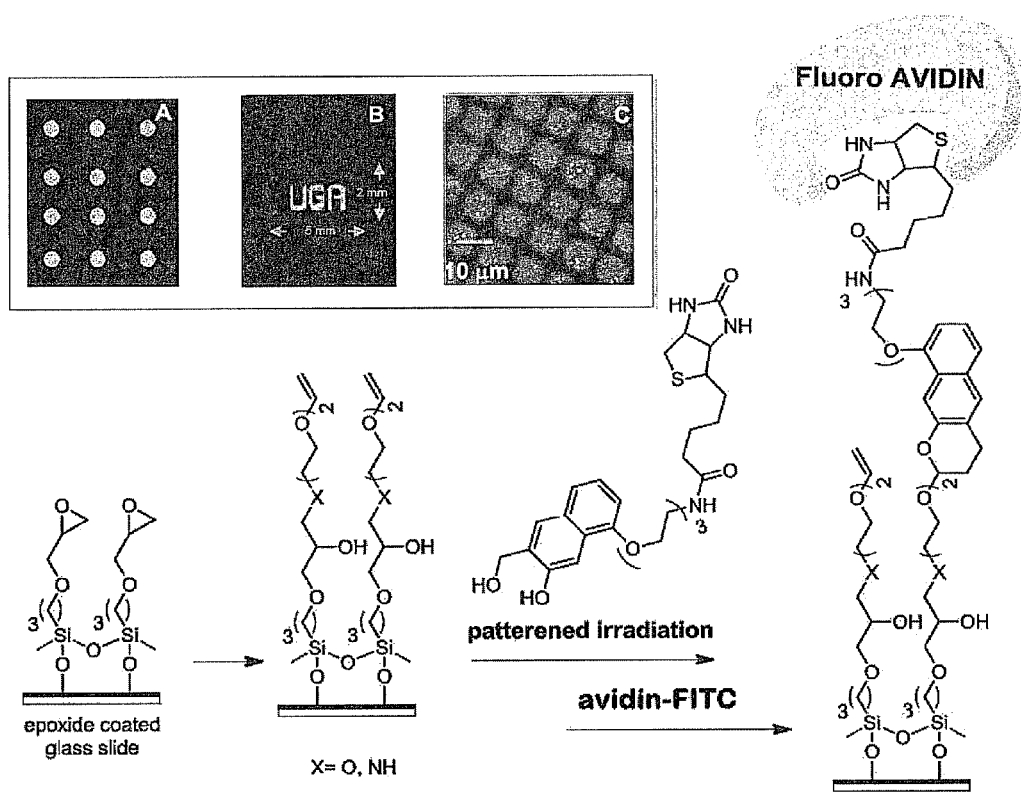
FIG. 29 is a schematic illustration of preparation and light-directed biotinylation of vinyl ether-coated slides followed by immobilization of FITC-avidin. The insert shows fluorescent images of vinyl ether-coated slides spotted with 2 µL drops of $10^{-4}$ M NQMP-TEG-biotin aqueous solution and flood irradiated (A); or covered with $10^{-4}$ M NQMP-TEG-biotin aqueous solution and irradiated via "UGA" mask (B) or 12.5 μm pitch copper grid (both enlarged).

The resulting vinyl ether-derivatized slides were covered with aqueous solution of NQMP-TEG-biotin 32b ($1\times10^{-4}$ M), and irradiated using 300 or 350 nm fluorescent lamps. Photochemical dehydration of 3-(hydroxymethyl)-2-naphthol moiety in 32b produces derivative of oNQM, which undergo very facile Diels-Alder cycloaddition to vinyl ether groups on the surface resulting in covalent immobilization of biotin molecules. Unreacted oNQM species rapidly react with water to regenerate 32b. Biotinylated glass slides were then developed with FITC-avidin in PBS solution for 15 minutes at 2° C. and thoroughly washed (FIG. 29). Surface derivatization was followed by FTIR and contact angle measurements.

Two procedures were employed to achieve patterned immobilization of FITC-avidin on vinyl ether-derivatized slides. In the first method, 2 µL droplets of 0.1 mM NQMP-TEG-biotin (32b) aqueous solution were placed on the slides, which were then flood irradiated for 10 minutes with fluorescent UV lamp, washed and stained with FITC-avidin (FIG. 29, Insert A). The actual photo-patterning has been achieved by the irradiation of the slides covered with solution of 32b via a shadow mask. The "latent" image was also developed using FITC-avidin (FIG. 29, inserts B and C). We used two different masks for irradiation: the first one had UGA cut in still plate in approximately 1.5 mm high letters. For the second, we used 12.5 µm pitch copper grid. Insert C in FIG. 29 illustrates this avidin photo-patterning method readily reproduce features as small as 1 µm. This is a remarkable result, since the photoreactive compound is not immobilized on the surface but rather present in low viscosity solution. High resolution photo-patterning in this case relies on a short lifetime (τ~7 milliseconds) of oNQM in aqueous solution, which prevents its migration from the site of irradiation.

Figure 30:
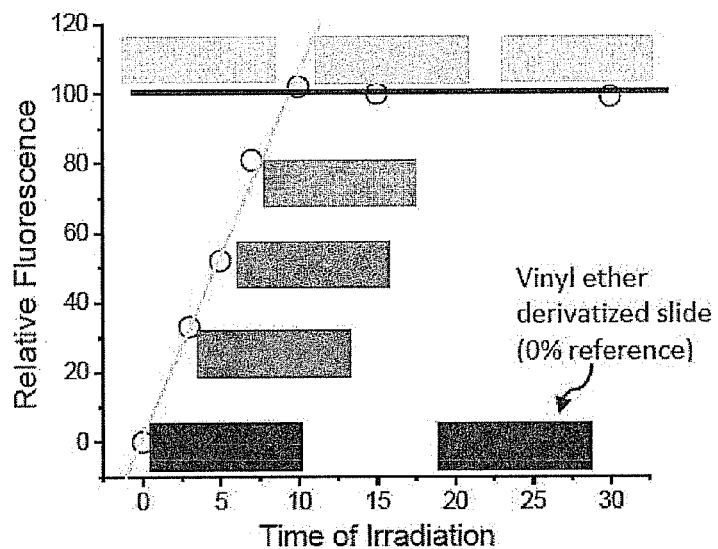
FIG. 30 illustrates the relative fluorescent intensity of FITC-avidin-stained vinyl ether-derivatized glass slides after various time of irradiation in 0.1 mM NQMP-TEG-biotin (32b) solution.

To evaluate the efficiency of photochemical surface derivatization, vinyl ether-coated slides were covered with 0.1 mM aqueous solution of NQMP-TEG-biotin (32b) and irradiated for various periods of time. Slides were then washed, treated with FITC-avidin, and fluorescence intensity was recorded. The relative fluorescence intensity of photo-derivatized slides increased with the exposure time reaching saturation at approximately 10 minutes. Longer irradiation times have no effect on the fluorescence of the slides (FIG. 30).

To test the photo-stability of photochemically-induced linkage, two slides were biotinylated using 10 minute irradiation in 0.1 M 32b solution and washed. One of the slides was further irradiated in aqueous PBS solution for 30 minutes. Both slides were then developed with FITC-avidin solution. The fluorescent intensity of the irradiated slide was 99% of the control one. This experiment confirms that the formation of Diels-Alder adduct on the surface is photochemically irreversible. Since concentration of the NQMP-TEG-biotin (32b) in the solution remains virtually unchanged after photolysis, saturation of fluorescence after 10 minutes of irradiation indicates that all accessible vinyl ether groups on the surface have reacted with oNQMs. Growth of fluorescence intensity follows zeroth-order kinetics (FIG. 30), indicating that the formation and diffusion of oNQM to the surface, rather than cycloaddition to immobilized vinyl ether groups, is a rate-limiting step in the derivatization process.

Figure 31:
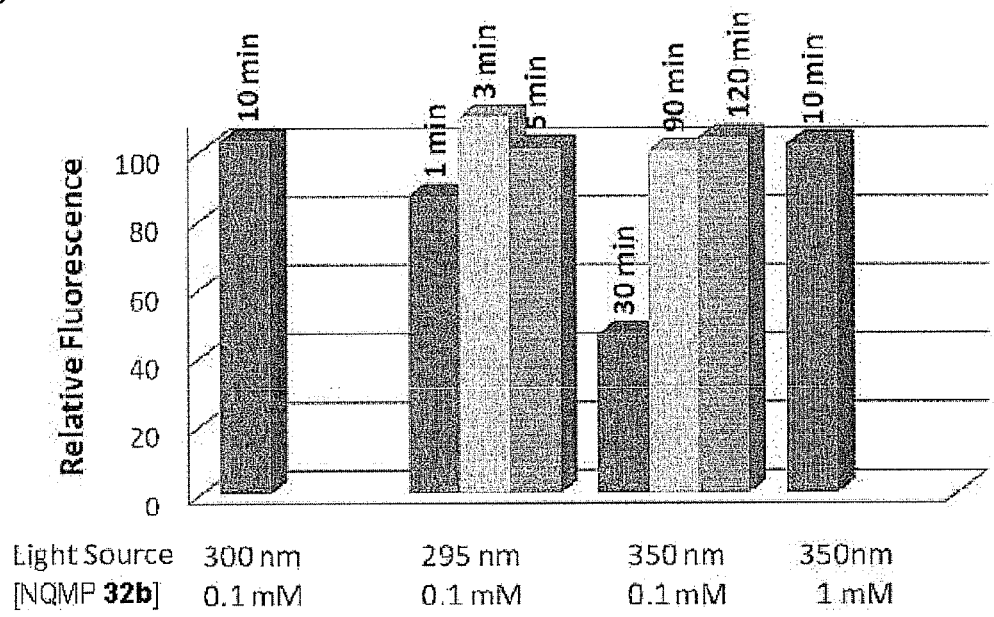
FIG. 31 illustrates the relative fluorescent intensity of FTIC-Avidin-stained glass slides biotinilated under different conditions.
Figure 32:
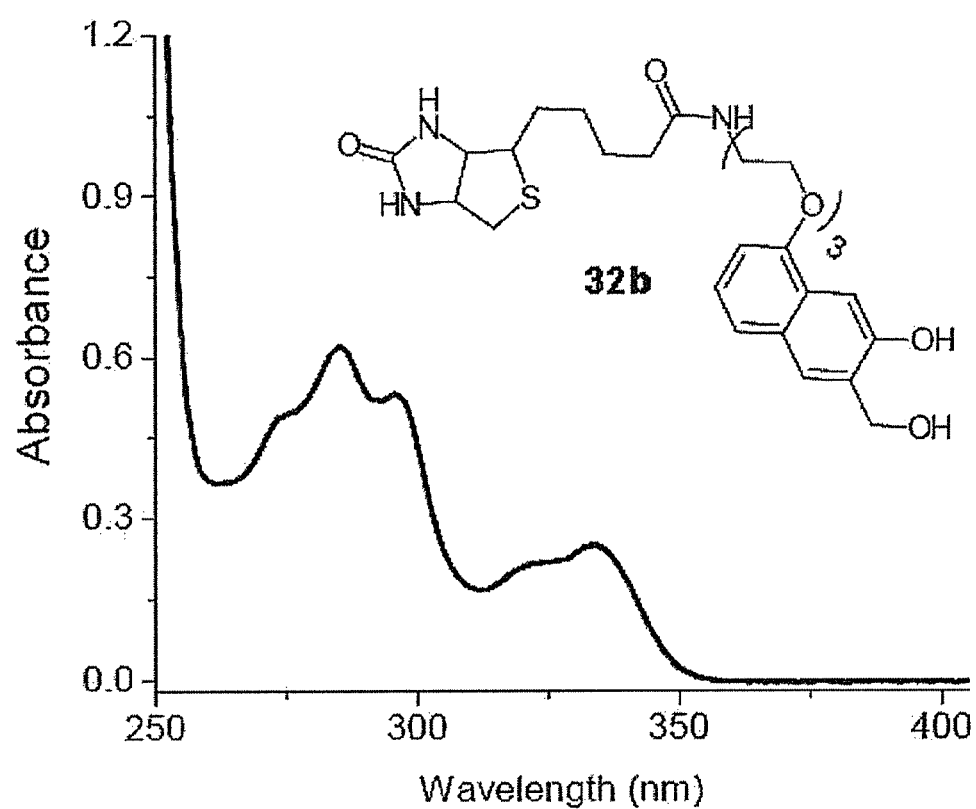
FIG. 32 illustrates the UV-spectrum of 0.1 mM aqueous solution of NQMP-TEG-biotin (32b).

The irradiation time can be adjusted using different light sources or concentrations of NQMP. Medium pressure mercury lamp equipped with 295 nm cut off glass filter allows us to cut exposure time to 3 minutes at 0.1 mM NQMP 32b (FIG. 31). On the other hand, if longer wavelength irradiation is required, 350 nm light can be employed for patterning. This process, however, is less efficient. Using 350 nm lamps with intensity similar to 300 nm fluorescent tubes discussed above, complete functionalization is achieved at approximately 100 minutes of irradiation. Reduced rate of surface derivatization is, apparently, due to the lower extinction coefficient of NQMP 32b at 350 nm (FIG. 32). In fact, at 10-fold higher concentration of 32b (1 mM), complete conversion at this wavelength is achieved in 10 minutes (FIG. 31).

Protein patterning procedures often require extensive washing to remove substrate non-specifically absorbed on the surface. In our experiments, the FTIC-Avidin-stained surfaces (e.g., A and B, FIG. 29) were washed by sonicating the glass slides in PBS solution for 30 minutes followed by overnight incubation in fresh phosphate buffer. From a practical point of view, a shorter washing procedure could enhance the efficiency of photo-click protein patterning. In order to reduce non-specific protein binding, we have developed a photochemical PEGylation procedure. After the initial patterning of the substrate on the vinyl ether-derivatized surfaces, slides are subjected to flood irradiation in the aqueous solution of NQMP-TEG (32c, FIG. 33). This procedure makes previously unexposed areas highly hydrophilic and significantly reduces protein binding. Longer PEG units attached to NQMP 32 can further increase this effect.

Figure 33:
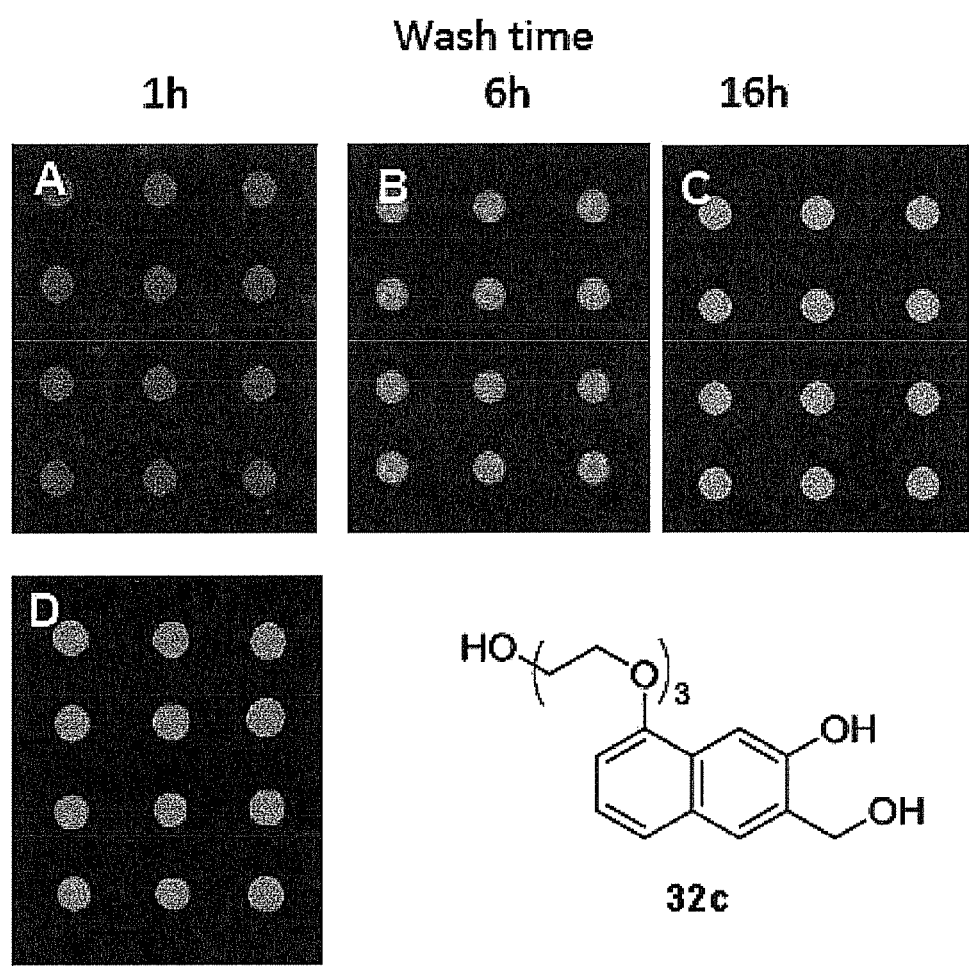
FIG. 33 illustrates vinyl ether-derivatized slides. A-D were spotted with NQMP 32b solution and irradiated with 300 nm light. Slide "D" was further irradiated in NQMP 32c solution. Slides were stained with FTIC-Avidin and washed in PBS solution for 1 hour (A and D), 6 hours (B), and 16 hours (C).

To test the efficiency of the photo-PEGylation procedure, four commercial epoxy-coated glass slides were treated with 2-(2-(vinyloxy)ethoxy)ethanamine under same conditions (FIG. 29). The resulting vinyloxy-derivatized slides were spotted with 2 µL droplets of 0.1 mM aqueous solution of NQMP-TEG-biotin (32b) and irradiated for 3 minutes with 300 nm fluorescent UV lamps. One of these slides was then immersed in 0.1 mM aqueous solution of NQMP-TEG (32c) and irradiated for additional 3 minutes. After FITC-avidin labeling, the slide was rinsed with water and incubated in PBS solution for 1 hour. The resulting fluorescent image of this slide shows high contrast between biotinilated and biotin-free areas (FIG. 33 D). Three other slides were treated with FITC-Avidin, rinsed, and incubated in PBS solution for 1 hour, 6 hours and 16 hours respectively (FIG. 33 A-C). 1 hour and 6 hour long washing are clearly insufficient to remove non-specifically absorbed avidin from the slide. Only 16 hour washing procedure produces contrast approaching that of photo-PEGylated slide. These experiments show that flood irradiation of biotin-patterned vinyloxy-slide does not decrease the amount of immobilized biotin molecules but drastically reduces non-specific binding of avidin to the slide.

Derivatization procedures discussed above produce glass slides with vinyl ether moieties attached to the surface via the vinylic oxygen atom (L1, FIG. 34). 2-Alkoxy substituent (O-L1) in benzo[g]chroman 34, which is formed in the photo-click reaction, is acid labile and can be hydrolyzed off at pH 1 (FIG. 34) (Arumugam and Popik, 2011 *J. Am. Chem. Soc.* 133:5573).

Figure 34:
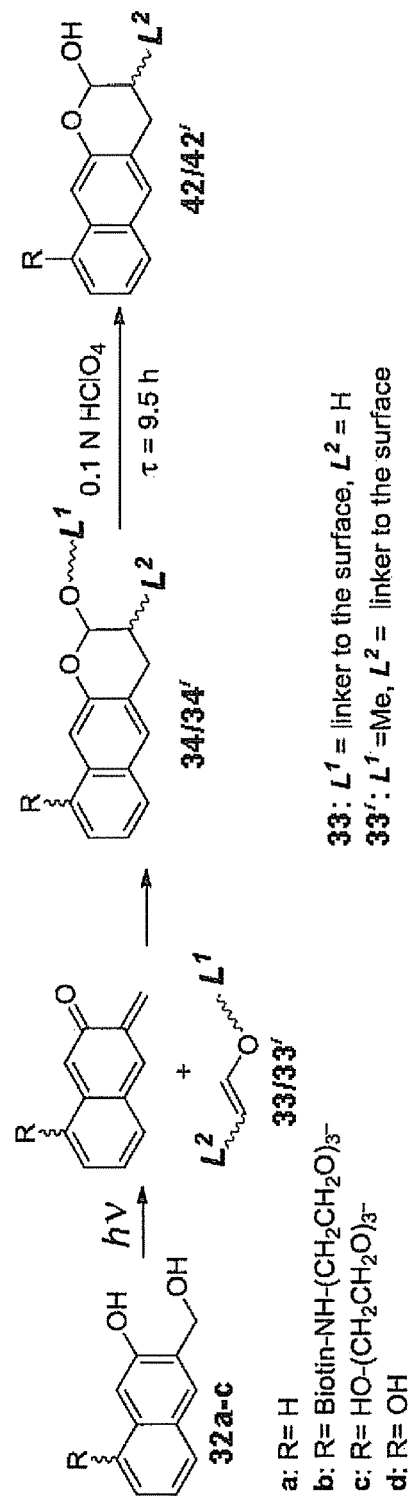
FIG. 34 is a schematic illustration of a derivatization procedure used to generate glass slides with vinyl ether moieties attached to the surface via the vinylic oxygen atom.

This hydrolytic liability of the linker 34 permits complete removal of the previously immobilized molecules from the glass surface. We have employed acid cleavage procedure to evaluate the efficiency of the photo-click immobilization. For this purpose slides of known epoxide group density (VWR #16001-030, density=$2\times10^{13}$ molecules per $mm^2$, surface area=1875 $mm^2$) were functionalized with vinyl ether groups and subsequently irradiated with 300 nm lamps for 10 minutes in 0.1 mM aqueous solution of NQMP 32a. The resulting slides that contained benzochroman 34a on the surface were incubated in 0.1N perchloric acid solution overnight to induce the release of 2-hydroxybenzochroman 42a (FIG. 34). The concentration of 42a in the supernatant solution was determined from its absorbance at 281 nm. The surface density was calculated from triplicate measurements to be $(1.40\pm0.06)\times10^{13}$ of 34a molecules per $mm^2$. In other words, all three steps of the process, i.e., vinyl ether functionalization of epoxy slides, photo-click derivatization, and acid-catalyzed release of the substrate, are very efficient proceeding with at least 70% overall yield.

Figure 35:
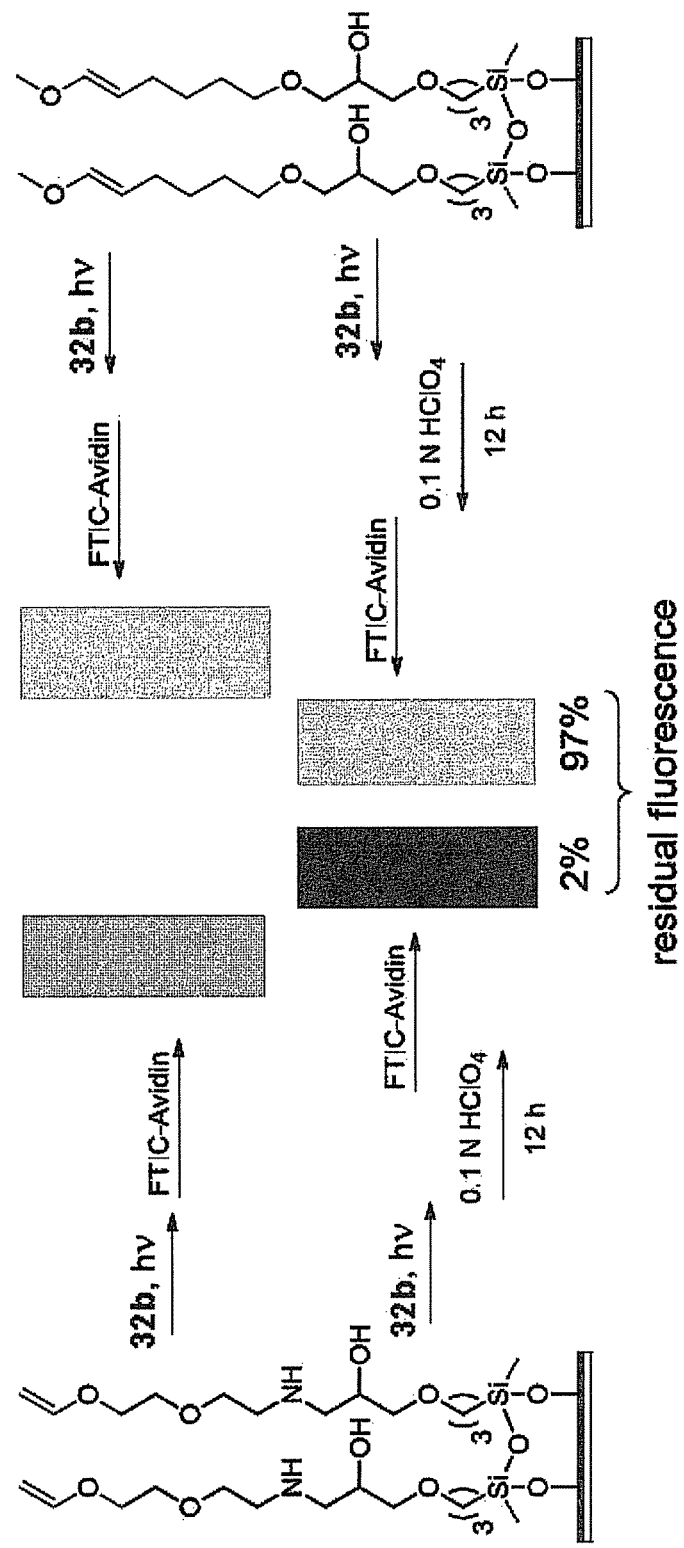
FIG. 35 illustrates hydrolytic stability of photochemically biotinylated slides.

To evaluate the yield of the acid-induced detachment procedure, two vinyl ether-derivatized slides were photo-biotinilated by irradiation in NQMP 32b solution. One of the resulting slides was then incubated overnight in 0.1 M perchloric acid. The acid-treated and the control slides were stained with FITC-avidin, washed in PBS solution overnight, and scanned using Typhoon imager (FIG. 35). The fluorescent intensity of the acid-treated slide was less than 2% of the second one, indicating almost quantitative loss of biotin molecules from the surface.

Photo-Diels-Alder click reaction can also be employed in applications that require hydrolytically stable linker between a surface and immobilized substrate. In this case, vinyl ether groups should be attached to the surface via β-carbon atom (e.g., 33', FIG. 34). We have prepared such vinyl ether-derivatized surface by treating the epoxide glass slides with 6-methoxyhex-5-en-1-ol in methylene chloride in the presence of catalytic amount of anhydrous p-toluenesulfonic acid. These slides were irradiated in an aqueous solution of NQMP 32b to yield biotinylated slides. One of these slides was incubated in 0.1 M perchloric acid solution overnight before FITC-avidin staining. As clearly seen from the FIG. 35, incubation in acidic solution did not significantly affect the fluorescent intensity of the slide, indicating that density of biotin groups on the surface remained the same. This observation underscores the stability of linker 34b' to acid-catalyzed hydrolysis.

The photo-click immobilization strategy described in this report is based on the fast and efficient hetero-Diels-Alder cycloaddition of photochemically generated o-naphthoquinone methides (oNQMs) to immobilized vinyl ether moieties. Since vinyloxy-derivatization of the surface is achieved via a simple and efficient process and a wide variety of substrates can be attached to naphthoquinone methide precursors, 3-(hydroxymethyl)-2-naphthols (NQMP), this method offers a new platform for light-directed surface functionalization. Photo-Diels-Alder patterning approach can be orthogonal to other derivatization techniques and can be used in conjunction with well-developed acetylene-azide click chemistry. The high rate of oNQMs cycloaddition to vinyl ether moieties makes this photochemical derivatization strategy very efficient. The unreacted oNQMs are quenched with water to regenerate NQMP. The competition between hydration and cycloaddition makes oNQMs very selective: vinyl ethers are reactive enough to outcompete addition of water to the substrate. We also describe a new photo-patterning paradigm, in which photochemically inert surface is selectively irradiated in a solution of a photoactive component. The short lifetime of photo-generated reactive species (oNQM) limits their migration from the site of irradiation and permits high special resolution of the patterning process. The photo-click immobilization technique comprising of o-napthoquinone methide precursor and vinyl ether can be tailored to produce permanent or a hydrolytically labile linkage.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claim.

What is claimed is:

1. A method for selectively labeling a substrate, the method comprising:

providing a precursor compound having one of the formulas:

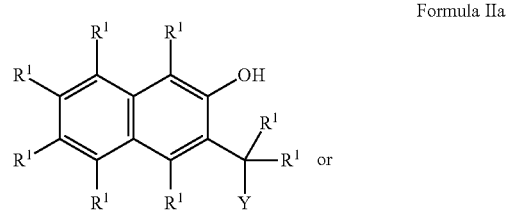

Formula IIa

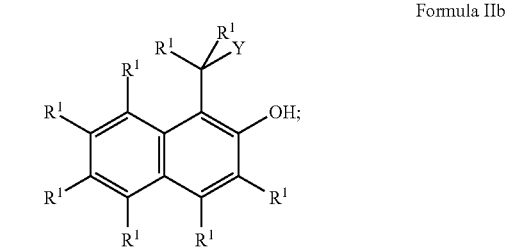

Formula IIb irradiating the precursor compound at a wavelength of 300 to 350 nm under conditions effective to form an o-naphthoquinone methide having one of the formulas:

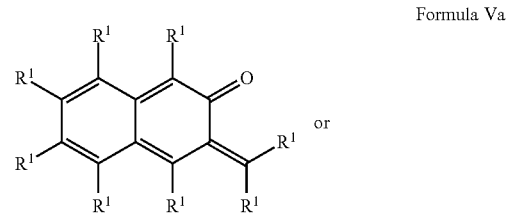

Formula Va

-continued

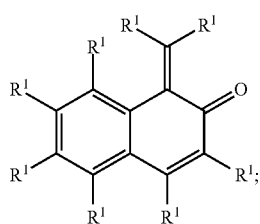
Formula Vb and
contacting the o-naphthoquinone methide with a polarized olefin attached to a surface of a substrate and having the formula:

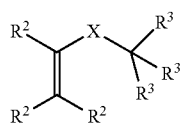
Formula III under conditions effective to form a hetero-Diels-Alder adduct,
wherein:
  each $R^1$ is independently H, halogen, or an organic group, with the proviso that at least one $R^1$ comprises a detectable label;
  each $R^2$ is independently H or an organic group;
  each $R^3$ is independently H, halogen, or an organic group;
  X is O or $NR^4$;
  Y is $OR^5$ or $NR^5_3{}^+(Z_{1/q})^-$ wherein Z is an anion having a negative charge of q;
  each $R^5$ is independently H or an organic group;
  optionally, two or more $R^1$ groups may be combined to form one or more rings;
  optionally, two or more $R^2$ groups may be combined to form one or more rings;
  optionally, two or more $R^3$ and/or $R^4$ groups may be combined to form one or more rings;
  optionally, two or more $R^5$ groups may be combined to form one or more rings; and
  with the proviso that at least one $R^2$, $R^3$, or $R^4$ comprises a linker group attached to the surface of the substrate.

2. The method of claim 1 wherein the precursor compound is irradiated in the presence of the polarized olefin.

3. The method of claim 2 wherein irradiating the precursor compound comprises pattern-wise irradiating the substrate to provide a pattern-wise labeled surface of the substrate.

4. The method of claim 1 wherein conditions effective to form the o-quinone methide comprise irradiation of an aqueous solution, suspension, or dispersion of the precursor compound.

5. The method of claim 1 wherein the substrate is selected from the group consisting of glass, quartz, silica, a metal, a semi-conductor, a polymer, a membrane, a liposome, a micelle, a macromolecule, a biomaterial, and combinations thereof.

6. The method of claim 1 wherein the label is detectable by a method selected from the group consisting of fluorescence, phosphorescence, radiation detection, optical and electrochemical methods, surface plasmon resonance imaging (SPRi), and combinations thereof.

7. The method of claim 1 wherein the detectable label comprises a probe.

8. The method of claim 7 wherein the probe comprises DNA, a peptide, a polypeptide, a protein, or a combination thereof.

9. The method of claim 1 further comprising removing the detectable label from the surface of the substrate by hydrolyzing the C—X bond.

10. A method for selectively labeling a substrate, the method comprising:
providing a precursor compound having one of the formulas:

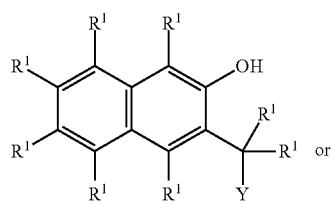
Formula IIa

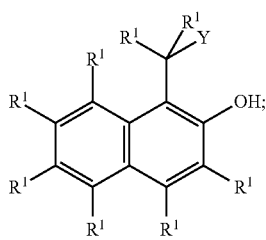
Formula IIb irradiating the precursor compound at a wavelength of 300 to 350 nm under conditions effective to form an o-naphthoquinone methide having one of the formulas:

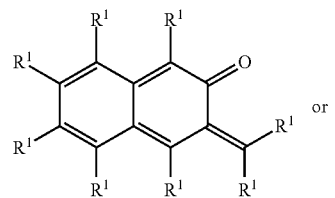
Formula Va

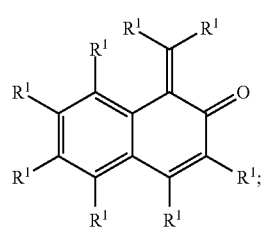
Formula Vb and
contacting the o-naphthoquinone methide with a polarized olefin attached to a surface of a substrate and having the formula:

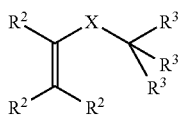

Formula III under conditions effective to form a hetero-Diels-Alder adduct,
wherein:
  each $R^1$ is independently H, halogen, or an organic group, with the proviso that at least one $R^1$ comprises a detectable label;
  each $R^2$ is independently H or an organic group;
  each $R^3$ is independently H, halogen, or an organic group;
  X is O or $NR^4$;
  Y is $OR^5$ or $NR^5_3{}^+(Z_{1/q})^-$ wherein Z is an anion having a negative charge of q;
  each $R^5$ is independently H or an organic group;
  optionally, two or more $R^1$ groups may be combined to form one or more rings;
  optionally, two or more $R^2$ groups may be combined to form one or more rings;
  optionally, two or more $R^3$ and/or $R^4$ groups may be combined to form one or more rings;
  optionally, two or more $R^5$ groups may be combined to form one or more rings;
  with the proviso that at least one $R^2$, $R^3$, or $R^4$ comprises a linker group attached to the surface of the substrate, and wherein the substrate comprises a planar surface or a bead.

11. The method of claim 5 wherein the biomaterial is selected from the group consisting of a virus, a small multicellular organism, DNA, RNA, a peptide, a polypeptide, a protein, a carbohydrate, a lipid, tissue, and combinations thereof.

* * * * *